US008759632B2

(12) United States Patent
Ro et al.

(10) Patent No.: US 8,759,632 B2
(45) Date of Patent: Jun. 24, 2014

(54) POLYNUCLEOTIDES ENCODING ISOPRENOID MODIFYING ENZYMES AND METHODS OF USE THEREOF

(75) Inventors: Dae-Kyun Ro, Calgary (CA); Karyn Newman, Berkeley, CA (US); Eric M. Paradise, Oakland, CA (US); Jay D. Keasling, Berkeley, CA (US); Mario Ouellet, El Cerrito, CA (US); Rachel Eachus, San Francisco, CA (US); Kimberly Ho, Novato, CA (US); Timothy Ham, El Cerrito, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 13/426,387

(22) Filed: Mar. 21, 2012

(65) Prior Publication Data

US 2012/0288905 A1   Nov. 15, 2012

Related U.S. Application Data

(62) Division of application No. 11/917,875, filed as application No. PCT/US2006/025572 on Jun. 29, 2006, now Pat. No. 8,163,980.

(60) Provisional application No. 60/697,067, filed on Jul. 5, 2005.

(51) Int. Cl.
*C12N 15/29* (2006.01)
*C12N 15/52* (2006.01)
*C12N 15/82* (2006.01)

(52) U.S. Cl.
USPC ..... 800/317.3; 800/287; 800/298; 435/320.1; 435/419

(58) Field of Classification Search
None
See application file for complete search history.

(56) References Cited

U.S. PATENT DOCUMENTS

| 8,163,980 B2 * | 4/2012 | Ro et al. ................. 800/287 |
| 2003/0148479 A1 | 8/2003 | Keasling et al. |
| 2003/0166255 A1 | 9/2003 | Chappell et al. |
| 2004/0005678 A1 | 1/2004 | Keasling et al. |
| 2004/0162420 A1 | 8/2004 | Xu |
| 2005/0019882 A1 | 1/2005 | Bouwmeester et al. |

FOREIGN PATENT DOCUMENTS

| EP | 1123978 | 8/2001 |
| EP | 1354955 | 10/2003 |
| WO | WO 93-20206 | 10/1993 |
| WO | WO 93/21326 | 10/1993 |
| WO | WO 98/59042 | 12/1998 |
| WO | WO 02/072758 | 9/2002 |
| WO | WO 03/025193 | 3/2003 |
| WO | WO 2007/005604 | 1/2007 |
| WO | WO 2007-048235 | 5/2007 |

OTHER PUBLICATIONS

Nguyen, D. et al. Journal of Biological Chemistry, May 28, 2010, vol. 285, No. 22, pp. 16588-16598.*
Abdin, et al., "Artemisinin, a Novel Antimalarial Drug: Biochemical and Molecular Approaches for Enhanced Production", Planta Medica, 2003; vol. 69, No. 4, pp. 289-299.
Jennewein, et al., "Coexpression in Yeast of Taxus cytochrome P450 Reductase with Cytochrome P450 Oxygenases Involved in Taxol Biosynthesis", Biotechnology and Bioengineering, 2005, vol. 89, No. 5, pp. 588-598.
Parshikov, et al., "Hydroxylation of 10-Deoxoartemisinin to 15-hydroxy-10-deoxoartemisinin by *Aspergillus niger*", 2004, Biotechnology Letters, vol. 26, pp. 607-610.
Svensson et al., "Identification of the Human Cytochrome P450 Enzymes Involved in the in vitro Metabolism of Artemisinin", 1999, J Clin Pharmacol, vol. 48, No. 4, pp. 528-535.
Teoh, et al., "*Artemisia annua* L. (Asteraceae) Trichome-Specific c DNAs Reveal CYP71AV1, a Cytochrome P450 with a Key Role in the Biosynthesis of the Antimalarial Sesquiterpene Lactone Artemisinin", 2006, FEBS Letters, vol. 580, No. 5, pp. 1411-1416.
Bertea, et al., "Identification of Intermediates and Enzymes Involved in the Early Steps of Artemisinin Biosynthesis in *Artemisia annua*.", 2005, Planta Med, vol. 71, pp. 40-47.
Dekraker et al., Hydroxylation of Sesquiterpenes by Enzymes from Chicory (*Cichorium intybus* L.), vol. 59, pp. 409-418, Tetrahedron (2003).
Extended European Search Report & Supplementary European Search Report dated Oct. 30, 2009 for Application No. 06785959.5 filed on Jun. 29, 2006 entitled "Polynucleotides Encoding Isoprenoid Modifying Enzymes and Methods of Use Thereof".
Hutvagner, et al., Gene, 1997, vol. 188, pp. 247-252.
Lupien, at al., "Regiospecific Cytochrome P4500 Limonene Hydroxylases from Mint (Mentha) Species: cDNA Isolation, Characterization and Functional Expression of (−)-4S-limonene-3-hydroxylase and (−)-4S limonene-6-hydroxylase", Archives of Biochemistry and Biophysics, 1999, vol. 368, pp. 181-192.
Martin, et al., "Engineering a Mevalonate Pathway in *Escherichia coli* for Production of Terpenoids", Nat. Biotechnol., 2003, No. 21, pp. 796-802.
Mercke, et al., Molecular Cloning, Expression and Characterization of Amorpha-4, 11-diene Synthase, a Key Enzyme of Artemisinin Biosynthesis in *Artemisia annua* L., Archives of Biochemistry and Biophysics, 2000, vol. 381, No. 2, pp. 173-180.
Nguyen, et al., Journal of Biological Chemistry, 2010, vol. 285, No. 22, pp. 16588-16598.

(Continued)

*Primary Examiner* — Russell Kallis
(74) *Attorney, Agent, or Firm* — Paula A. Borden; Bozicevic, Field & Francis LLP.

(57) ABSTRACT

The present invention provides isolated nucleic acids comprising nucleotide sequences encoding isoprenoid modifying enzymes, as well as recombinant vectors comprising the nucleic acids. The present invention further provides genetically modified host cells comprising a subject nucleic acid or recombinant vector. The present invention further provides a transgenic plant comprising a subject nucleic acid. The present invention further provides methods of producing an isoprenoid compound, the method generally involving culturing a subject genetically modified host cell under conditions that permit synthesis of an isoprenoid compound modifying enzyme encoded by a subject nucleic acid.

27 Claims, 15 Drawing Sheets

(56) References Cited

OTHER PUBLICATIONS

Picaud, et al., Expression, Purification and Characterization of Recombinant Amorpha-4, 11-diene Synthase from *Artemisia annua* L, Archives of Biochemistry of Biophysics, 2005, vol. 436, pp. 215-226.

Ro, et al., "Loblolly Pine Abietadienol/Abietadienal Oxidase PtAO (CYP720B1) is a Multifunctional, Multisubstrate Cytochrome P450 Monooxygenase", Proc Natl Acad Sci USA, 2005, vol. 102, No. 22, pp. 8060-8065.

Smit, et al., "Biosynthesis of Isoprenoids via Mevalonate in Archaea: the lost Pathway", Genome Res., 2008, vol. 10., No. 10, pp. 1468-1484.

* cited by examiner

FIG. 1

*CYP71D-A4* cDNA sequence.

```
CYP71D-A4 cDNA coding sequence
ATGAAGAGTATACTAAAAGCAATGGCACTCTCACTGACCACTTCCATT
GCTCTTGCAACGATCCTTTTGTTCGTTTACAAGTTCGCTACTCGTTCC
AAATCCACCAAAAAAAGCCTTCCTGAGCCATGGCGGCTTCCCATTATT
GGTCACATGCATCACTTGATTGGTACAACGCCACATCGTGGGGTTAGG
GATTTAGCCAGAAAGTATGGATCTTTGATGCATTTACAGCTTGGTGAA
GTTCCAACAATCGTGGTGTCATCTCCGAAATGGGCTAAAGAGATTTTG
ACAACGTACGACATTACCTTTGCTAACAGGCCCGAGACTTTAACTGGT
GAGATTGTTTTATATCACAATACGGATGTTGTTCTTGCACCTTATGGT
GAATACTGGAGGCAATTACGTAAAATTTGCACATTGGAGCTTTTGAGT
GTTAAGAAAGTAAAGTCATTTCAGTCACTTCGTGAAGAGGAGTGTTGG
AATTTGGTTCAAGAGATTAAAGCTTCAGGTTCAGGGAGACCGGTTAAC
CTTTCAGAGAATGTTTTCAAGTTGATTGCAACGATACTTAGTAGAGCC
GCATTTGGGAAAGGGATCAAGGACCAGAAAGAGTTAACGGAGATTGTG
AAAGAGATACTGAGGCAAACTGGTGGTTTTGATGTGGCAGATATCTTT
CCTTCAAAGAAATTTCTTCATCATCTTTCGGGCAAGAGAGCTCGGTTA
ACTAGCCTTCGCAAAAGATCGATAATTTAATCGATAACCTTGTAGCT
GAGCATACTGTTAACACCTCCAGTAAAACTAACGAGACACTCCTCGAT
GTTCTTTTAAGGCTCAAAGACAGTGCTGAATTCCCATTAACATCTGAT
AACATTAAAGCCATCATTTTGGATATGTTTGGAGCAGGCACAGACACT
TCCTCATCCACAATCGAATGGGCGATTTCGGAACTCATAAAGTGTCCG
AAAGCAATGGAGAAAGTACAAGCGGAATTGAGGAAAGCATTGAACGGA
AAAGAAAAGATCCATGAGGAAGACATTCAAGAACTAAGCTACTTGAAC
ATGGTAATCAAAGAAACATTGAGGTTGCACCCTCCACTACCCTTGGTT
CTGCCAAGAGAGTGCCGCCAACCAGTCAATTTGGCTGGATACAACATA
CCCAATAAGACCAAACTTATTGTCAACGTCTTTGCGATAAATAGGGAC
CCTGAATATTGGAAGACGCTGAAGCTTTCATCCCTGAACGATTTGAA
AATAGTTCTGCAACTGTCATGGGTGCAGAATACGAGTATCTTCCGTTT
GGAGCTGGGAGAAGGATGTGTCCTGGAGCCGCACTTGGTTTAGCTAAC
GTGCAGCTCCCGCTCGCTAATATACTATATCATTTCAACTGGAAACTC
CCCAATGGTGTGAGCTATGACCAGATCGACATGACCGAGAGCTCTGGA
GCCACGATGCAAAGAAAGACTGAGTTGTTACTCGTTCCAAGTTTCTAG
(SEQ ID NO:1)
```

FIG. 2

Amorphadiene 12-oxidase amino acid sequence
MKSILKAMALSLTTSIALATILLFVYKFATRSKSTKKSLPEPWRLPII
GHMHHLIGTTPHRGVRDLARKYGSLMHLQLGEVPTIVVSSPKWAKEIL
TTYDITFANRPETLTGEIVLYHNTDVVLAPYGEYWRQLRKICTLELLS
VKKVKSFQSLREEECWNLVQEIKASGSGRPVNLSENVFKLIATILSRA
AFGKGIKDQKELTEIVKEILRQTGGFDVADIFPSKKFLHHLSGKRARL
TSLRKKIDNLIDNLVAEHTVNTSSKTNETLLDVLLRLKDSAEFPLTSD
NIKAIILDMFGAGTDTSSSTIEWAISELIKCPKAMEKVQAELRKALNG
KEKIHEEDIQELSYLNMVIKETLRLHPPLPLVLPRECRQPVNLAGYNI
PNKTKLIVNVFAINRDPEYWKDAEAFIPERFENSSATVMGAEYEYLPF
GAGRRMCPGAALGLANVQLPLANILYHFNWKLPNGVSYDQIDMTESSG
ATMQRKTELLLVPSF (SEQ ID NO:2)

FIG. 3

*Artemisia annua* cytochrome P450 reductase DNA

AACPR cDNA coding sequence
ATGCAATCAACAACTTCCGTTAAGTTATCTCCCTTCGATCTAATGA
CGGCGTTACTTAACGGCAAGGTATCGTTCGACACATCAAACACATC
GGATACGAATATTCCGTTAGCGGTGTTTATGGAGAATCGTGAGCTT
TTGATGATTTTAACTACTTCGGTTGCGGTGTTGATCGGATGCGTTG
TGGTGCTTGTGTGGAGACGGTCGTCGTCGGCGGCGAAGAAAGCGGC
GGAGTCGCCGGTGATTGTTGTGCCGAAGAAAGTGACGGAGGATGAG
GTTGATGACGGACGGAAGAAAGTTACTGTGTTTTTTGGAACTCAGA
CTGGTACTGCTGAAGGTTTTGCTAAGGCGCTTGTTGAAGAAGCTAA
AGCGCGATATGAAAAGGCGGTGTTTAAAGTGATTGATTTGGATGAT
TATGCTGCTGAAGATGATGAGTATGAGGAGAAGTTAAAGAAAGAAT
CTCTTGCTTTTTTCTTTTTAGCTACGTATGGAGATGGTGAGCCGAC
AGATAATGCTGCTAGATTCTATAAATGGTTTACCGAGGGTGAAGAG
AAAGGTGAATGGCTTGACAAGCTTCAATACGCAGTGTTTGGACTTG
GTAACAGACAGTATGAGCATTTCAACAAGATTGCGAAGGTGGTCGA
TGAAAAACTTGTGGAGCAGGGTGCAAAGCGCCTTGTTCCTGTTGGC
ATGGGAGACGATGATCAATGTATCGAAGACGACTTCACTGCATGGA
AAGAGTTGGTGTGGCCTGAGTTGGATCAATTACTTCGTGATGAGGA
TGATACATCTGTTGCCACTCCATACACAGCTGCTGTTGGAGAATAC
CGTGTTGTGTTCCATGACAAACCAGAGACATATGATCAGGATCAAC
TGACAAATGGCCATGCTGTTCATGATGCTCAACATCCATGCAGATC
CAATGTCGCTGTCAAAAAGGAGCTCCATTCCCCTCTATCTGACCGG
TCTTGCACTCATTTGGAATTTGATATCTCTAATACTGGATTATCGT
ATGAAACTGGGGACCATGTTGGAGTCTACGTTGAGAATCTAAGTGA
AGTTGTGGACGAAGCTGAAAAATTAATAGGTTTACCGCCGCACACT
TATTTCTCAGTACATACTGATAACGAAGACGGGACACCACTTGGTG
GAGCCTCTTTGCCACCTCCTTTCCCTCCATGCACTTTAAGAAAAGC
ATTGGCTTCCTATGCCGATGTTTTGAGCTCTCCTAAAAAGTCAGCT
TTGCTTGCTTTAGCTGCTCATGCTACTGATTCTACTGAAGCTGATA
GACTGAAATTTTTTGCGTCTCCTGCTGGAAGGATGAATATGCTCA
GTGGATAGTTGCAAGCCACAGAAGTCTCCTTGAGGTCATGGAGGCC
TTCCCATCAGCTAAGCCTCCGCTTGGTGTTTTTTTTGCATCTGTCG
CCCCACGTTTGCAGCCGAGATACTATTCCATTTCTTCTTCCCCAAA
GTTTGCGCCAAATAGGATTCATGTAACTTGTGCATTAGTGTATGAG
CAAACACCATCAGGCCGCGTTCACAAGGGAGTCTGTTCAACATGGA
TGAAGAATGCCGTGCCTATGACAGAAAGCCAGGATTGCAGTTGGGC
CCCAATTTATGTTAGAACATCCAATTTCAGACTTCCTTCTGATCCT
AAGGTCCCAGTTATCATGATTGGCCCAGGCACTGGATTGGCTCCAT
TTAGAGGTTTCCTTCAGGAAAGGTTAGCTCAGAAGGAAGCTGGGAC
TGAGCTCGGAACAGCCATCTTATTCTTCGGATGCAGGAATCGCAAA
GTGGATTTCATATATGAGGACGAGCTTAATAATTTCGTGGAGACGG
GGGCTCTTTCCGAGCTTGTTACGGCCTTCTCTCGTGAAGGTGCCAC
TAAGGAGTACGTGCAACACAAGATGACTCAGAAGGCTTCGGATATC
TGGAATTTACTCTCTGAGGGAGCATATTTGTATGTTTGCGGTGATG
CCAAAGGCATGGCCAAAGATGTACATCGGACTCTGCACACTATTGT
GCAAGAACAGGGATCTCTAGACTCCTCAAAGGCGGAGCTCTACGTG
AAGAATCTACAAATGGCAGGAAGATATCTCCGTGATGTATGGGTCG
ACATGGAACAGAAGTTGATTTCCGAAGAAGACCTCGAGTAA (SEQ
ID NO:3)

FIG. 4

Artemisia annua cytochrome P450 reductase
amino acid sequence
MQSTTSVKLSPFDLMTALLNGKVSFDTSNTSDTNIPLAVFMENREL
LMILTTSVAVLIGCVVVLVWRRSSSAAKKAAESPVIVVPKKVTEDE
VDDGRKKVTVFFGTQTGTAEGFAKALVEEAKARYEKAVFKVIDLDD
YAAEDDEYEEKLKKESLAFFFLATYGDGEPTDNAARFYKWFTEGEE
KGEWLDKLQYAVFGLGNRQYEHFNKIAKVVDEKLVEQGAKRLVPVG
MGDDDQCIEDDFTAWKELVWPELDQLLRDEDDTSVATPYTAAVGEY
RVVFHDKPETYDQDQLTNGHAVHDAQHPCRSNVAVKKELHSPLSDR
SCTHLEFDISNTGLSYETGDHVGVYVENLSEVVDEAEKLIGLPPHT
YFSVHTDNEDGTPLGGASLPPPFPPCTLRKALASYADVLSSPKKSA
LLALAAHATDSTEADRLKFFASPAGKDEYAQWIVASHRSLLEVMEA
FPSAKPPLGVFFASVAPRLQPRYYSISSSPKFAPNRIHVTCALVYE
QTPSGRVHKGVCSTWMKNAVPMTESQDCSWAPIYVRTSNFRLPSDP
KVPVIMIGPGTGLAPFRGFLQERLAQKEAGTELGTAILFFGCRNRK
VDFIYEDELNNFVETGALSELVTAFSREGATKEYVQHKMTQKASDI
WNLLSEGAYLYVCGDAKGMAKDVHRTLHTIVQEQGSLDSSKAELYV
KNLQMAGRYLRDVWVDMEQKLISEEDLE (SEQ ID NO:4)

Rt=34.53, Sample, 99% MS match to the authentic standard

Rt=34.57, Authentic standard

FIG. 9

>71D-B1-nt
ATGGCACTTTCACTGACCACCTCCATTGCTCTTGCCACGATCCTTTTCTTCGTAATTTACAAGTTCGCTAC
TCGTTCCAAATCCACAAAAAACAGCCTTCCTGAGCCATGGCGACTTCCCATTATTGGTCACATGCATCACT
TGATTGGTACAATACCACATCGTGGGCTTATGGATTTAGCCAGAAAGTATGGATCTTTAATGCATTTACAG
CTTGGTGAAGTTTCAACAATCGTGGTGTCATCTCCGAAATGGGCTAAAGAGATTTTGACAACGTACGACAT
TGCCTTTGCTAACAGGCCCTGGACTTTGGCTGGTGAGATTGTTGTATATCGCAATACAAATATTGCTGCTG
CACCTTATGGTGAATACTGGAGGCGATTACGTAAACTTTGCACATCGGAGCTTATGAGTGTTAAGAAAGTA
AAGTCATATCAGTCGCTTCGTGAAGAGGAGTGTTGGAATTTGGTTCAAGAGATTAAAGCTTCAGGTTCAGG
GATACCGGTTAACCTTTCAGAGAACATTTTCAAGTTGATTGCAACGATACTTTGTAGAGCCGCGTTTGGAA
AAGGAGTCAAGGACCAGAAGGAGTGTACGGAGATTATGAAAGAGATGTTGAGGGAAGTTGGTGGTTTTGAT
GTGGCAGATATCTTTCCTTCGAAGAAATTTCTTCATCATCTTTCAGGCAAGAGAGCCAGGTTAACTAGCAT
TCATAAGAAGCTCGATAATTTTATCAATAACCTTGTTGCTGAGCATACTTTCAAAACTTCAAGTAAAACTG
AGGAGACACTTCTTGATGTTCTTCTAAGGCTCAAAGATAGCGCTGAATTCCCATTAACAGCTGACAATGTT
AAAGCCATCATTTTGGATATATTTGCAGCAGGGACAGACACTTCATCAACCACAATCGAATGGGCGATTTC
GGAACTCATAAAGTGTCCGAGAGCGATGGAGAAAGTACAAGCAGAACTGAGGAAAGCACTTAACGGAAAAG
AAAAGATCCATGAGGAAGATATTCAAGGACTAAGCTACTTAAACTTGGTAATCAAAGAAACATTAAGGTTG
CACCCTCCACTACCCTTGTTGCCAAGAGAGTGCCGTGAACCAGTCAATTTGGCTGGATACGACATACCCAA
TAAGACAAGACTTATTGTCAACGTCTTTGCGATAAATAGGGACCCAGAATACTGGAAAGACGCTGAAATTT
TCATCCCCGAACGATTTGAAAATAGTTCTACAACTCTCATGGGTGCAGAATATGAGTATCTTCCGTTTGGA
GCTGGGAGAAGGATGTGTCCTGGAGCCGCACTTGGTTTAGCCAACGTGCAGCTACCGCTCGCTAATATACT
ATATCATTTCAACTGGAAACTCCCCAACGGTGCGAGCTATGATCAGATCGACATGACCGAGAGGTTTGGAA
TCTCGGTTGAAAGAAAGACTCAGTTGTTACTCGTACCAAGTTTCTAG (SEQ ID NO:5)

FIG. 10

>71D-B1-aa
MALSLTTSIALATILFFVIYKFATRSKSTKNSLPEPWRLPIIGHMHHLIGTIPHRGLMDLARKYGSLMHLQ
LGEVSTIVVSSPKWAKEILTTYDIAFANRPWTLAGEIVVYRNTNIAAAPYGEYWRRLRKLCTSELMSVKKV
KSYQSLREEECWNLVQEIKASGSGIPVNLSENIFKLIATILCRAAFGKGVKDQKECTEIMKEMLREVGGFD
VADIFPSKKFLHHLSGKRARLTSIHKKLDNFINNLVAEHTFKTSSKTEETLLDVLLRLKDSAEFPLTADNV
KAIILDIFAAGTDTSSTTIEWAISELIKCPRAMEKVQAELRKALNGKEKIHEEDIQGLSYLNLVIKETLRL
HPPLPLLPRECREPVNLAGYDIPNKTRLIVNVFAINRDPEYWKDAEIFIPERFENSSTTLMGAEYEYLPFG
AGRRMCPGAALGLANVQLPLANILYHFNWKLPNGASYDQIDMTERFGISVERKTQLLLVPSF (SEQ ID
NO:6)

FIG. 12

```
>71D-C1-nt
GCCCTTCGAGCCGTATGGGGATTACTGGCGGCAATTACGTAAACTTTGCACATTGGAGCTTTTGAGTGCTA
AGAAAGTAGAGTCATATCAGTCGCTTCGTGAAGAGGAGTGTTGGAATTTAGTTCAAGAGATTAAAGCTTCA
GGTTCAGGGATACCGGTTAACCTTTCAGAGAATATTTACAAGTTGGTTGCAATGATACTTAGTAGAGCTGC
GTTTGGGAAAAGAATCAAGGACCATAAGGAGTTTACGGAGCTTGTGGAACAGATGTTGAGGGAACTTGGTG
GTTTTGATGTGGCAGATATCTTTCCTTCGCAGAAATTTCTACATCATATTTCGGGCAAGAGATCTAGGTTA
ACTAGCATTCACAAAAAGCTCGATAATTTAATCAATAACCTTGTTGCTGAGCATATTGTTGAAGCCTCAAG
TAAAACTAAGGAGACGCTCCTTGATGTTCTTCTAAGGCACAAAGATAGCCTTGAATTCCCATTGACAGCTG
ATAACGTTAAAGCCATCATTTTGGTATGAATTAATCCAATATATTTTTTTTTCAAAAGGCCATAATAGTG
TTAAACAAGCTTGAAATTTTTTATAACTAAGTACATGCACTAACTTTAGTACTCGTGAAAATATAATGAGT
CATCATAGGGGTTCCATGAAATATACAGGACATGTTTACAGCAGGCACAGACACTTCGTCAACCACAATCG
AATGGGTGATTTCGGAACTCATAAAGTGTCCGAGAGCTATGGAGAAAATACAAGCGGAACTGAGGAAAGCA
CTTAACGGAAAAGAAAAGATCCACGAGGAAGACATCCAAGAACTAAGCTACTTAAACTTGGTAATCAAAGA
AACATTAAGGTTGCACCCTCCACTACCCTTGGTTTTGCCACGAGAGTGCCGTCAACCAGTCAATTTGGCTG
GATATGACATACCCAATAAGACCAAACTTATTGTCAACGTCTTTGCGATAAATAGGGACCCTGAATACTGG
AAAGACGCTGAATCTTTCATCCCAGAGCGCTTCTTAACTCTGGT (SEQ ID NO:7)
```

Isoprenoid metabolic pathways

Mevalonate pathway

DXP pathway

POLYNUCLEOTIDES ENCODING ISOPRENOID MODIFYING ENZYMES AND METHODS OF USE THEREOF

CROSS-REFERENCE

This application claims the benefit of U.S. Provisional Patent Application No. 60/697,067, filed Jul. 5, 2005, which application is incorporated herein by reference in its entirety.

FIELD OF THE INVENTION

The present invention is in the field of production of isoprenoid compounds, and in particular enzymes that modify isoprenoid compounds.

BACKGROUND OF THE INVENTION

Isoprenoids constitute an extremely large and diverse group of natural products that have a common biosynthetic origin, i.e., a single metabolic precursor, isopentenyl diphosphate (IPP). At least 20,000 isoprenoids have been described. By definition, isoprenoids are made up of so-called isoprene (C5) units. The number of C-atoms present in the isoprenoids is typically divisible by five (C5, C10, C15, C20, C25, C30 and C40), although irregular isoprenoids and polyterpenes have been reported. Isoprenoid compounds are also referred to as "terpenes" or "terpenoids." Important members of the isoprenoids include the carotenoids, sesquiterpenoids, diterpenoids, and hemiterpenes. Carotenoids include, e.g., lycopene, β-carotene, and the like, many of which function as antioxidants. Sesquiterpenoids include, e.g., artemisinin, a compound having anti-malarial activity. Diterpenoids include, e.g., taxol, a cancer chemotherapeutic agent.

Isoprenoids comprise the most numerous and structurally diverse family of natural products. In this family, terpenoids isolated from plants and other natural sources are used as commercial flavor and fragrance compounds as well as pharmaceutical compounds such as anti-malarial, anti-viral, and anti-cancer drugs. A majority of the terpenoid compounds in use today are natural products or their derivatives. The source organisms (e.g., trees, marine invertebrates) of many of these natural products are neither amenable to the large-scale cultivation necessary to produce commercially viable quantities nor to genetic manipulation for increased production or derivatization of these compounds. Therefore, the natural products must be produced semi-synthetically from analogs or synthetically using conventional chemical syntheses. Furthermore, many natural products have complex structures, and, as a result, are currently uneconomical or impossible to synthesize. Such natural products must be either extracted from their native sources, such as trees, sponges, corals and marine microbes; or produced synthetically or semi-synthetically from more abundant precursors. Extraction of a natural product from a native source is limited by the availability of the native source; and synthetic or semi-synthetic production of natural products can suffer from low yield and/or high cost. Such production problems and limited availability of the natural source can restrict the commercial and clinical development of such products.

An example of an important sesquiterpene compound is artemisinin. Artemisinin is a highly effective anti-malarial drug that is currently extracted from plants (*Artemisia annua*) and is used to make combination therapy medications. Plant-derived artemisinin is expensive and its availability is subject to weather and political conditions in the countries that grow the plants. Artemisinic acid is a key intermediate in the biosynthesis of artemisinin. Conversion of amorpha-4,11-diene to artemisinic alcohol, an important step in making artemisinin, by traditional chemistry is a difficult and costly process.

There is a need in the art for methods of generating isoprenoid compounds that avoid some of the above-mentioned drawbacks. The present invention addresses this need by providing polynucleotides that encode enzymes that modify isoprenoid compounds, and host cells that are genetically modified to produce such enzymes.

LITERATURE

Bertea et al. (2005) *Planta Med.* 71:40-47; deKraker et al. (2003) *Tetradedron* 59:409-418; Martin et al. (2003) *Nat. Biotechnol.* 21:796-802; WO 03/025193; U.S. Patent Publication No. 20050019882; U.S. Patent Publication No. 20030148479; U.S. Patent Publication No. 20040005678; U.S. Patent Publication No. 20030166255.

SUMMARY OF THE INVENTION

The present invention provides isolated nucleic acids comprising nucleotide sequences encoding isoprenoid modifying enzymes, as well as recombinant vectors comprising the nucleic acids. The present invention further provides genetically modified host cells comprising a subject nucleic acid or recombinant vector. The present invention further provides a transgenic plant comprising a subject nucleic acid. The present invention further provides methods of producing an isoprenoid compound, the method generally involving culturing a subject genetically modified host cell under conditions that permit synthesis of an enzyme encoded by a subject nucleic acid, which enzyme modifies an isoprenoid compound.

BRIEF DESCRIPTION OF THE DRAWINGS

FIG. 1 depicts the nucleotide sequence of a CYP71D-A4 cDNA coding sequence (SEQ ID NO:1).

FIG. 2 depicts an amorphadiene 12-oxidase amino acid sequence (SEQ ID NO:2).

FIG. 3 depicts the nucleotide sequence of the coding region of an *Artemisia annua* cytochrome P450 reductase cDNA (SEQ ID NO:3).

FIG. 4 depicts an *Artemisia annua* cytochrome P450 reductase amino acid sequence (SEQ ID NO:4).

FIG. 9 depicts the nucleotide sequence of a cDNA (clone 71D-B1) encoding an isoprenoid-modifying enzyme (SEQ ID NO:5).

FIG. 10 depicts an amino acid sequence of an isoprenoid-modifying enzyme (71D-B1; SEQ ID NO:6).

FIG. 12 depicts the nucleotide sequence of a genomic DNA encoding an isoprenoid-modifying enzyme (SEQ ID NO:7).

DEFINITIONS

The terms "isoprenoid," "isoprenoid compound," "terpene," "terpene compound," "terpenoid," and "terpenoid compound" are used interchangeably herein. Isoprenoid compounds are made up various numbers of so-called isoprene (C5) units. The number of C-atoms present in the isoprenoids is typically evenly divisible by five (e.g., C5, C10, C15, C20, C25, C30 and C40). Irregular isoprenoids and polyterpenes have been reported, and are also included in the definition of "isoprenoid." Isoprenoid compounds include, but are not limited to, monoterpenes, sesquiterpenes, triterpenes, polyterpenes, and diterpenes.

As used herein, the term "prenyl diphosphate" is used interchangeably with "prenyl pyrophosphate," and includes monoprenyl diphosphates having a single prenyl group (e.g., IPP and DMAPP), as well as polyprenyl diphosphates that include 2 or more prenyl groups. Monoprenyl diphosphates include isopentenyl pyrophosphate (IPP) and its isomer dimethylallyl pyrophosphate (DMAPP).

As used herein, the term "terpene synthase" refers to any enzyme that enzymatically modifies IPP, DMAPP, or a polyprenyl pyrophosphate, such that a terpenoid compound is produced. The term "terpene synthase" includes enzymes that catalyze the conversion of a prenyl diphosphate into an isoprenoid.

The word "pyrophosphate" is used interchangeably herein with "diphosphate." Thus, e.g., the terms "prenyl diphosphate" and "prenyl pyrophosphate" are interchangeable; the terms "isopentenyl pyrophosphate" and "isopentenyl diphosphate" are interchangeable; the terms farnesyl diphosphate" and farnesyl pyrophosphate" are interchangeable; etc.

The term "mevalonate pathway" or "MEV pathway" is used herein to refer to the biosynthetic pathway that converts acetyl-CoA to IPP. The mevalonate pathway comprises enzymes that catalyze the following steps: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway is illustrated schematically in FIG. 14. The "top half" of the mevalonate pathway refers to the enzymes responsible for the conversion of acetyl-CoA to mevalonate through a MEV pathway intermediate.

Figure 15:
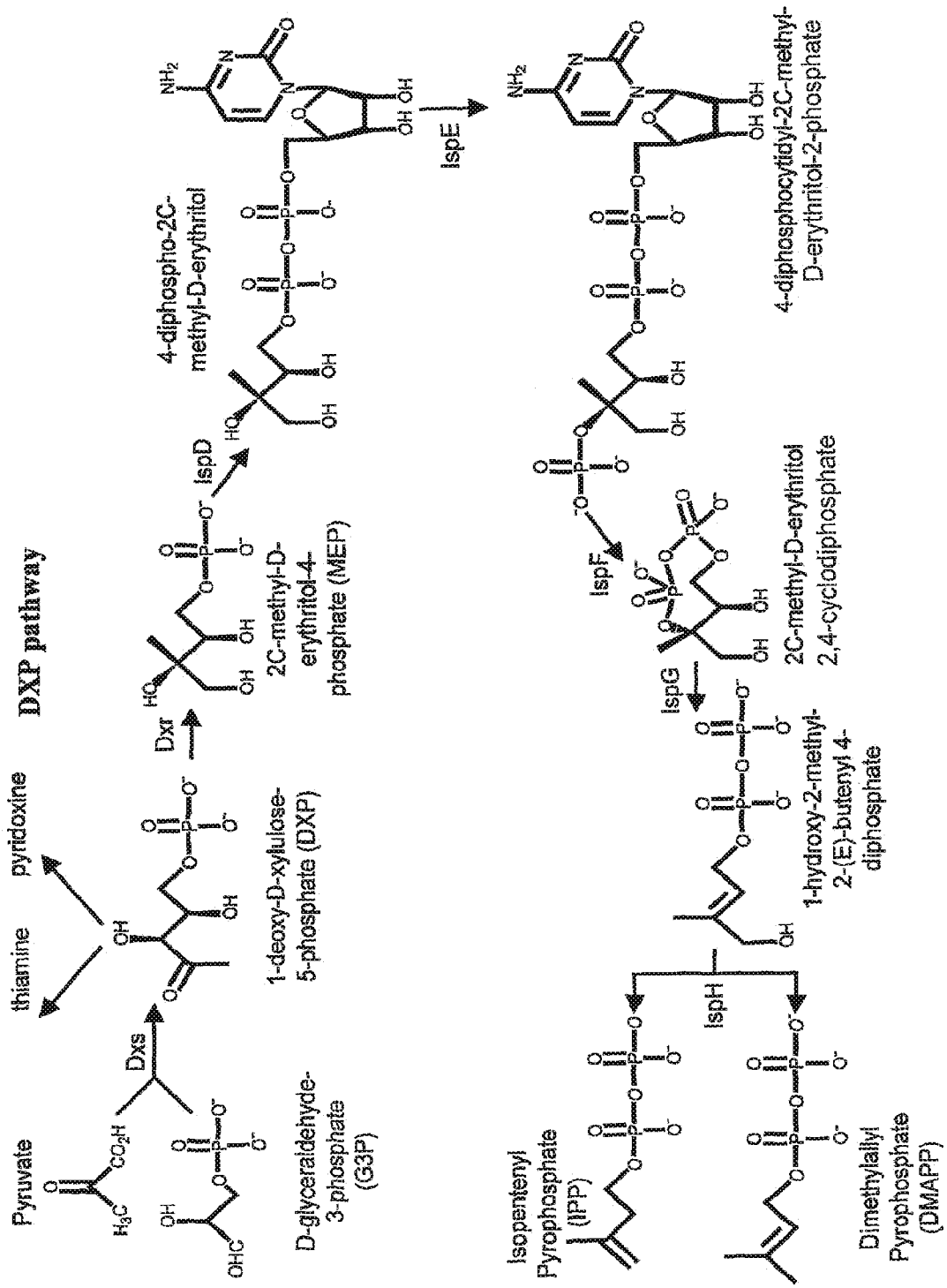
FIG. 15 is a schematic representation of the DXP pathway for the production of IPP and dimethylallyl pyrophosphate (DMAPP).

The term "1-deoxy-D-xylulose 5-diphosphate pathway" or "DXP pathway" is used herein to refer to the pathway that converts glyceraldehyde-3-phosphate and pyruvate to IPP and DMAPP through a DXP pathway intermediate, where DXP pathway comprises enzymes that catalyze the reactions depicted schematically in FIG. 15.

As used herein, the term "prenyl transferase" is used interchangeably with the terms "isoprenyl diphosphate synthase" and "polyprenyl synthase" (e.g., "GPP synthase," "FPP synthase," "OPP synthase," etc.) to refer to an enzyme that catalyzes the consecutive 1'-4 condensation of isopentenyl diphosphate with allylic primer substrates, resulting in the formation of prenyl diphosphates of various chain lengths.

The terms "polynucleotide" and "nucleic acid," used interchangeably herein, refer to a polymeric form of nucleotides of any length, either ribonucleotides or deoxynucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "peptide," "polypeptide," and "protein" are used interchangeably herein, and refer to a polymeric form of amino acids of any length, which can include coded and non-coded amino acids, chemically or biochemically modified or derivatized amino acids, and polypeptides having modified peptide backbones.

The term "naturally-occurring" as used herein as applied to a nucleic acid, a cell, or an organism, refers to a nucleic acid, cell, or organism that is found in nature. For example, a polypeptide or polynucleotide sequence that is present in an organism (including viruses) that can be isolated from a source in nature and which has not been intentionally modified by a human in the laboratory is naturally occurring.

As used herein the term "isolated" is meant to describe a polynucleotide, a polypeptide, or a cell that is in an environment different from that in which the polynucleotide, the polypeptide, or the cell naturally occurs. An isolated genetically modified host cell may be present in a mixed population of genetically modified host cells.

As used herein, the term "exogenous nucleic acid" refers to a nucleic acid that is not normally or naturally found in and/or produced by a given bacterium, organism, or cell in nature. As used herein, the term "endogenous nucleic acid" refers to a nucleic acid that is normally found in and/or produced by a given bacterium, organism, or cell in nature. An "endogenous nucleic acid" is also referred to as a "native nucleic acid" or a nucleic acid that is "native" to a given bacterium, organism, or cell. For example, the nucleic acids encoding HMGS, mevalonate kinase, and phosphomevalonate kinase in represent exogenous nucleic acids to *E. coli*. These mevalonate pathway nucleic acids can be cloned from *Saccharomyces cerevisiae*. In *S. cerevisiae*, the gene sequences encoding HMGS, MK, and PMK on the chromosome would be "endogenous" nucleic acids.

The term "heterologous nucleic acid," as used herein, refers to a nucleic acid wherein at least one of the following is true: (a) the nucleic acid is foreign ("exogenous") to (i.e., not naturally found in) a given host microorganism or host cell; (b) the nucleic acid comprises a nucleotide sequence that is naturally found in (e.g., is "endogenous to") a given host microorganism or host cell (e.g., the nucleic acid comprises a nucleotide sequence that is endogenous to the host microorganism or host cell) but is either produced in an unnatural (e.g., greater than expected or greater than naturally found) amount in the cell, or differs in sequence from the endogenous nucleotide sequence such that the same encoded protein (having the same or substantially the same amino acid sequence) as found endogenously is produced in an unnatural (e.g., greater than expected or greater than naturally found) amount in the cell; (c) the nucleic acid comprises two or more nucleotide sequences or segments that are not found in the same relationship to each other in nature, e.g., the nucleic acid is recombinant.

"Recombinant," as used herein, means that a particular nucleic acid (DNA or RNA) is the product of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non-translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions, and may indeed act to modulate production of a desired product by various mechanisms (see "DNA regulatory sequences", below).

Thus, e.g., the term "recombinant" polynucleotide or nucleic acid refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. This artificial combination is often accomplished by either chemical synthesis means, or by the artificial manipulation of isolated segments of nucleic acids, e.g., by genetic engineering techniques.

By "construct" is meant a recombinant nucleic acid, generally recombinant DNA, which has been generated for the purpose of the expression of a specific nucleotide sequence(s), or is to be used in the construction of other recombinant nucleotide sequences.

As used herein, the terms "operon" and "single transcription unit" are used interchangeably to refer to two or more contiguous coding regions (nucleotide sequences that encode a gene product such as an RNA or a protein) that are coordinately regulated by one or more controlling elements (e.g., a promoter). As used herein, the term "gene product" refers to RNA encoded by DNA (or vice versa) or protein that is encoded by an RNA or DNA, where a gene will typically comprise one or more nucleotide sequences that encode a protein, and may also include introns and other non-coding nucleotide sequences.

The terms "DNA regulatory sequences," "control elements," and "regulatory elements," used interchangeably herein, refer to transcriptional and translational control sequences, such as promoters, enhancers, polyadenylation signals, terminators, protein degradation signals, and the like, that provide for and/or regulate expression of a coding sequence and/or production of an encoded polypeptide in a host cell.

The term "transformation" is used interchangeably herein with "genetic modification" and refers to a permanent or transient genetic change induced in a cell following introduction of new nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell. In prokaryotic cells, permanent changes can be introduced into the chromosome or via extrachromosomal elements such as plasmids and expression vectors, which may contain one or more selectable markers to aid in their maintenance in the recombinant host cell. Suitable methods of genetic modification include viral infection, transfection, conjugation, protoplast fusion, electroporation, particle gun technology, calcium phosphate precipitation, direct microinjection, and the like. The choice of method is generally dependent on the type of cell being transformed and the circumstances under which the transformation is taking place (i.e. in vitro, ex vivo, or in vivo). A general discussion of these methods can be found in Ausubel, et al, Short Protocols in Molecular Biology, 3rd ed., Wiley & Sons, 1995.

"Operably linked" refers to a juxtaposition wherein the components so described are in a relationship permitting them to function in their intended manner. For instance, a promoter is operably linked to a coding sequence if the promoter affects its transcription or expression. As used herein, the terms "heterologous promoter" and "heterologous control regions" refer to promoters and other control regions that are not normally associated with a particular nucleic acid in nature. For example, a "transcriptional control region heterologous to a coding region" is a transcriptional control region that is not normally associated with the coding region in nature.

A "host cell," as used herein, denotes an in vivo or in vitro eukaryotic cell, a prokaryotic cell, or a cell from a multicellular organism (e.g., a cell line) cultured as a unicellular entity, which eukaryotic or prokaryotic cells can be, or have been, used as recipients for a nucleic acid (e.g., an expression vector that comprises a nucleotide sequence encoding one or more biosynthetic pathway gene products such as mevalonate pathway gene products), and include the progeny of the original cell which has been genetically modified by the nucleic acid. It is understood that the progeny of a single cell may not necessarily be completely identical in morphology or in genomic or total DNA complement as the original parent, due to natural, accidental, or deliberate mutation. A "recombinant host cell" (also referred to as a "genetically modified host cell") is a host cell into which has been introduced a heterologous nucleic acid, e.g., an expression vector. For example, a subject prokaryotic host cell is a genetically modified prokaryotic host cell (e.g., a bacterium), by virtue of introduction into a suitable prokaryotic host cell a heterologous nucleic acid, e.g., an exogenous nucleic acid that is foreign to (not normally found in nature in) the prokaryotic host cell, or a recombinant nucleic acid that is not normally found in the prokaryotic host cell; and a subject eukaryotic host cell is a genetically modified eukaryotic host cell, by virtue of introduction into a suitable eukaryotic host cell a heterologous nucleic acid, e.g., an exogenous nucleic acid that is foreign to the eukaryotic host cell, or a recombinant nucleic acid that is not normally found in the eukaryotic host cell.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength. Hybridization and washing conditions are well known and exemplified in Sambrook, J., Fritsch, E. F. and Maniatis, T. Molecular Cloning: A Laboratory Manual, Second Edition, Cold Spring Harbor Laboratory Press, Cold Spring Harbor (1989), particularly Chapter 11 and Table 11.1 therein; and Sambrook, J. and Russell, W., Molecular Cloning: A Laboratory Manual, Third Edition, Cold Spring Harbor Laboratory Press, Cold Spring Harbor (2001). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Hybridization conditions and post-hybridization washes are useful to obtain the desired determine stringency conditions of the hybridization. One set of illustrative post-hybridization washes is a series of washes starting with 6×SSC (where SSC is 0.15 M NaCl and 15 mM citrate buffer), 0.5% SDS at room temperature for 15 minutes, then repeated with 2×SSC, 0.5% SDS at 45° C. for 30 minutes, and then repeated twice with 0.2×SSC, 0.5% SDS at 50° C. for 30 minutes. Other stringent conditions are obtained by using higher temperatures in which the washes are identical to those above except for the temperature of the final two 30 minute washes in 0.2×SSC, 0.5% SDS, which is increased to 60° C. Another set of highly stringent conditions uses two final washes in 0.1×SSC, 0.1% SDS at 65° C. Another example of stringent hybridization conditions is hybridization at 50° C. or higher and 0.1×SSC (15 mM sodium chloride/1.5 mM sodium citrate). Another example of stringent hybridization conditions is overnight incubation at 42° C. in a solution: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1× SSC at about 65° C. Stringent hybridization conditions and post-hybridization wash conditions are hybridization conditions and post-hybridization wash conditions that are at least as stringent as the above representative conditions.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al., supra, 9.50-9.51). For hybridizations with shorter nucleic acids, i.e., oligonucleotides, the position of mismatches becomes more important, and the length of the oligonucleotide determines its specificity (see Sambrook et al., supra, 11.7-11.8). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

The term "conservative amino acid substitution" refers to the interchangeability in proteins of amino acid residues having similar side chains. For example, a group of amino acids having aliphatic side chains consists of glycine, alanine, valine, leucine, and isoleucine; a group of amino acids having aliphatic-hydroxyl side chains consists of serine and threonine; a group of amino acids having amide-containing side chains consists of asparagine and glutamine; a group of amino acids having aromatic side chains consists of phenylalanine, tyrosine, and tryptophan; a group of amino acids having basic side chains consists of lysine, arginine, and histidine; and a group of amino acids having sulfur-containing side chains consists of cysteine and methionine. Exemplary conservative amino acids substitution groups are: valine-leucine-isoleucine, phenylalanine-tyrosine, lysine-arginine, alanine-valine, and asparagine-glutamine.

"Synthetic nucleic acids" can be assembled from oligonucleotide building blocks that are chemically synthesized using procedures known to those skilled in the art. These building blocks are ligated and annealed to form gene segments which are then enzymatically assembled to construct the entire gene. "Chemically synthesized," as related to a sequence of DNA, means that the component nucleotides were assembled in vitro. Manual chemical synthesis of DNA may be accomplished using well-established procedures, or automated chemical synthesis can be performed using one of a number of commercially available machines. The nucleotide sequence of the nucleic acids can be modified for optimal expression based on optimization of nucleotide sequence to reflect the codon bias of the host cell. The skilled artisan appreciates the likelihood of successful expression if codon usage is biased towards those codons favored by the host. Determination of preferred codons can be based on a survey of genes derived from the host cell where sequence information is available.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including BLAST, available over the world wide web at ncbi.nlm.nih.gov/BLAST. See, e.g., Altschul et al. (1990), *J. Mol. Biol.* 215:403-10. Another alignment algorithm is FASTA, available in the Genetics Computing Group (GCG) package, from Madison, Wis., USA, a wholly owned subsidiary of Oxford Molecular Group, Inc. Other techniques for alignment are described in Methods in Enzymology, vol. 266: Computer Methods for Macromolecular Sequence Analysis (1996), ed. Doolittle, Academic Press, Inc., a division of Harcourt Brace & Co., San Diego, Calif., USA. Of particular interest are alignment programs that permit gaps in the sequence. The Smith-Waterman is one type of algorithm that permits gaps in sequence alignments. See *Meth. Mol. Biol.* 70: 173-187 (1997). Also, the GAP program using the Needleman and Wunsch alignment method can be utilized to align sequences. See *J. Mol. Biol.* 48: 443-453 (1970).

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "an isoprenoid modifying enzyme" includes a plurality of such enzymes and reference to "the cytochrome P450 reductase" includes reference to one or more cytochrome P450 reductases and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF THE INVENTION

The present invention provides isolated nucleic acids comprising nucleotide sequences encoding isoprenoid modifying enzymes, as well as recombinant vectors comprising the nucleic acids. The present invention further provides genetically modified host cells comprising a subject nucleic acid or recombinant vector. The present invention further provides a transgenic plant comprising a subject nucleic acid. The present invention further provides methods of producing an isoprenoid compound, the method generally involving culturing a subject genetically modified host cell under conditions that permit synthesis of an isoprenoid compound modifying enzyme encoded by a subject nucleic acid.

Nucleic Acids, Vectors, and Host Cells

The present invention provides an isolated nucleic acid comprising a nucleotide sequence encoding an enzyme that modifies an isoprenoid compound, where an enzyme that modifies an isoprenoid compound is referred to herein as "an isoprenoid modifying enzyme." A subject nucleic acid comprising a nucleotide sequence encoding an isoprenoid modifying enzyme is referred to as "an isoprenoid-modifying enzyme nucleic acid." In particular embodiments, a subject isolated isoprenoid-modifying enzyme nucleic acid comprises a nucleotide sequence encoding a cytochrome P450 monooxygenase. In particular embodiments, a subject isolated isoprenoid-modifying enzyme nucleic acid comprises a nucleotide sequence encoding an isoprenoid oxidase. In some embodiments, a subject isolated isoprenoid-modifying enzyme nucleic acid comprises a nucleotide sequence encoding a terpene hydroxylase. In some embodiments, a subject isolated isoprenoid-modifying enzyme nucleic acid comprises a nucleotide sequence encoding a terpene oxidase. In some embodiments, a subject isolated isoprenoid-modifying enzyme nucleic acid comprises a nucleotide sequence encoding a sesquiterpene oxidase. In some embodiments, a subject isolated isoprenoid-modifying enzyme nucleic acid comprises a nucleotide sequence encoding a sesquiterpene hydroxylase.

NADPH-cytochrome P450 oxidoreductase (CPR, EC 1.6.2.4) is the redox partner of many P450-monooxygenases. The present invention further provides an isolated nucleic acid comprising a nucleotide sequence encoding a cytochrome P450 reductase (CPR). A subject nucleic acid comprising a nucleotide sequence encoding a CPR is referred to as "a CPR nucleic acid." A CPR encoded by a subject CPR nucleic acid transfers electrons from NADPH to cytochrome P450. In general, a CPR encoded by a subject CPR nucleic acid transfers electrons from NADPH to an isoprenoid-modifying enzyme, e.g., a sesquiterpene oxidase, encoded by a subject isoprenoid-modifying enzyme-encoding nucleic acid.

Nucleic Acids Encoding Isoprenoid Modifying Enzymes

In some embodiments, a subject isolated nucleic acid comprises a nucleotide sequence encoding a polypeptide that exhibits isoprenoid hydroxylase and/or isoprenoid oxidase activity. In some embodiments, a subject isolated nucleic acid comprises a nucleotide sequence encoding a cytochrome P450 monooxygenase. In some embodiments, a subject isolated nucleic acid comprises a nucleotide sequence encoding an isoprenoid hydroxylase. In some embodiments, a subject isolated nucleic acid comprises a nucleotide sequence encoding an isoprenoid oxidase. In some embodiments, a subject isolated nucleic acid comprises a nucleotide sequence encoding a polypeptide that carries out successive hydroxylation and oxidation reactions, e.g., the polypeptide hydroxylates a terpene compound to generate a terpene alcohol, oxidizes the terpene alcohol to generate a terpene aldehyde, and oxidizes the terpene aldehyde to generate a terpene carboxylic acid. In some embodiments, a subject isolated nucleic acid comprises a nucleotide sequence encoding a polypeptide that catalyzes hydroxylation and/or oxidation of an isopropenyl group of a terpene, e.g., catalyzes hydroxylation of an isopropenyl group of a monoterpene, a diterpene, a triterpene, a sesquiterpene, or a polyterpene. In some embodiments, a subject isolated nucleic acid comprises a nucleotide sequence encoding a monoterpene oxidase. In some embodiments, a subject isolated nucleic acid comprises a nucleotide sequence encoding a monoterpene hydroxylase. In some embodiments, a subject isolated nucleic acid comprises a nucleotide sequence encoding a polyterpene hydroxylase. In some embodiments, a subject isolated nucleic acid comprises a nucleotide sequence encoding a polyterpene oxidase. In some embodiments, a subject isolated nucleic acid comprises a nucleotide sequence encoding a diterpene hydroxylase. In some embodiments, a subject isolated nucleic acid comprises a nucleotide sequence encoding a diterpene oxidase. In some embodiments, a subject isolated nucleic acid comprises a nucleotide sequence encoding a triterpene hydroxylase. In some embodiments, a subject isolated nucleic acid comprises a nucleotide sequence encoding a triterpene oxidase. In some embodiments, a subject isolated nucleic acid comprises a nucleotide sequence encoding a sesquiterpene hydroxylase. In some embodiments, a subject isolated nucleic acid comprises a nucleotide sequence encoding a sesquiterpene oxidase. In some embodiments, a subject isolated nucleic acid comprises a nucleotide sequence encoding a sesquiterpene C12-hydroxylase. In some embodiments, a subject isolated nucleic acid comprises a nucleotide sequence encoding a polypeptide that carries out the C12 oxidation of a sesquiterpene. In some embodiments, a subject isolated nucleic acid comprises a nucleotide sequence encoding an amorphadiene 12-oxidase.

The product of action of a terpene cyclase (also referred to as a "terpene synthase") reaction is the so-called "terpene skeleton." In some embodiments, a subject isolated nucleic acid comprises a nucleotide sequence encoding an isoprenoid-modifying enzyme that catalyzes the hydroxylation and/or oxidation of a terpene skeleton, or a downstream product thereof. In general, a substrate of an isoprenoid-modifying enzyme encoded by a subject nucleic acid comprises a terpene skeleton or a modified terpene skeleton. In many embodiments, a substrate of an isoprenoid-modifying enzyme encoded by a subject nucleic acid comprises an isopropenyl group.

Monoterpene substrates of an isoprenoid-modifying enzyme encoded by a subject nucleic acid include, but are not limited to, any monoterpene substrate that yields an oxidation product that is a monoterpene compound or is an intermediate in a biosynthetic pathway that gives rise to a monoterpene compound. Exemplary monoterpene substrates include, but are not limited to, monoterpene substrates that fall into any of the following families: Acyclic monoterpenes, Dimethyloctanes, Menthanes, Irregular Monoterpenoids, Cineols, Camphanes, Isocamphanes, Monocyclic monoterpenes, Pinanes, Fenchanes, Thujanes, Caranes, Ionones, Iridanes, and Cannabanoids. Exemplary monoterpene substrates, intermediates, and products include, but are not limited to, limonene, citranellol, geraniol, menthol, perillyl alcohol, linalool, and thujone.

Diterpene substrates of an isoprenoid-modifying enzyme encoded by a subject nucleic acid include, but are not limited to, any diterpene substrate that yields an oxidation product that is a diterpene compound or is an intermediate in a biosynthetic pathway that gives rise to a diterpene compound. Exemplary diterpene substrates include, but are not limited to, diterpene substrates that fall into any of the following families: Acyclic Diterpenoids, Bicyclic Diterpenoids, Monocyclic Diterpenoids, Labdanes, Clerodanes, Taxanes, Tricyclic Diterpenoids, Tetracyclic Diterpenoids, Kaurenes, Beyerenes, Atiserenes, Aphidicolins, Grayanotoxins, Gibberellins, Macrocyclic Diterpenes, and Elizabethatrianes. Exemplary diterpene substrates, intermediates, and products include, but are not limited to, casbene, eleutherobin, paclitaxel, prostratin, and pseudopterosin.

Triterpene substrates of an isoprenoid-modifying enzyme encoded by a subject nucleic acid include, but are not limited to, any triterpene substrate that yields an oxidation product that is a triterpene compound or is an intermediate in a biosynthetic pathway that gives rise to a triterpene compound. Exemplary triterpene substrates, intermediates, and products include, but are not limited to, arbrusideE, bruceantin, testosterone, progesterone, cortisone, and digitoxin.

Sesquiterpene substrates of an isoprenoid-modifying enzyme encoded by a subject nucleic acid include, but are not limited to, any sesquiterpene substrate that yields an oxidation product that is a sesquiterpene compound or is an intermediate in a biosynthetic pathway that gives rise to a sesquiterpene compound. Exemplary sesquiterpene substrates include, but are not limited to, sesquiterpene substrates that fall into any of the following families: Farnesanes, Monocyclofarnesanes, Monocyclic sesquiterpenes, Bicyclic sesquiterpenes, Bicyclofarnesanes, Bisbolanes, Santalanes, Cuprames, Herbertanes, Gymnomitranes, Trichothecanes, Chamigranes, Carotanes, Acoranes, Antisatins, Cadinanes, Oplopananes, Copaanes, Picrotoxanes, Himachalanes, Longipinanes, Longicyclanes, Caryophyllanes, Modhephanes, Siphiperfolanes, Humulanes, Intergrifolianes, Lippifolianes, Protoilludanes, Illudanes, Hirsutanes, Lactaranes, Sterpuranes, Fomannosanes, Marasmanes, Germacranes, Elemanes, Eudesmanes, Bakkanes, Chilosyphanes, Guaianes, Pseudoguaianes, Tricyclic sesquiterpenes, Patchoulanes, Trixanes, Aromadendranes, Gorgonanes, Nardosinanes, Brasilanes, Pinguisanes, Sesquipinanes, Sesquicamphanes, Thujopsanes, Bicylcohumulanes, Alliacanes, Sterpuranes, Lactaranes, Africanes, Integrifolianes, Protoilludanes, Aristolanes, and Neolemnanes. Exemplary sesquiterpene substrates include, but are not limited to, amorphadiene, alloisolongifolene, (−)-α-trans-bergamotene, (−)-β-elemene, (+)-germacrene A, germacrene B, (+)-γ-gurjunene, (+)-ledene, neointermedeol, (+)-β-selinene, and (+)-valencene.

Whether a subject nucleic acid encodes a terpene oxidase, or a terpene hydroxylase, can be readily ascertained using standard assays for these enzymatic activities, using the appropriate substrate. Products of the enzymatic modification are generally analyzed by gas chromatography-mass spectrometry. Whether a subject nucleic acid encodes a sesquiterpene oxidase, or a sesquiterpene hydroxylase, can be readily ascertained using standard assays for these enzymatic activities. See, e.g., U.S. Patent Publication No. 20050019882, the disclosure of which is incorporated by reference herein.

In some embodiments, a subject nucleic acid comprises the nucleotide sequence depicted in FIG. 1 and set forth in SEQ ID NO:1. In some embodiments, a subject nucleic acid comprises a nucleotide sequence having at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% nucleotide sequence identity to the nucleotide sequence set forth in SEQ ID NO:1. In some embodiments, a subject nucleic acid comprises a nucleotide sequence having one, two, three, four, five, six, seven, eight, nine, ten, from about 10 to about 15, from about 15 to about 20, from about 20 to about 25, or from about 25 to about 50 nucleotide substitutions compared to the nucleotide sequence set forth in SEQ ID NO:1.

In some embodiments, a subject nucleic acid comprises a nucleotide sequence having at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% nucleotide sequence identity to the nucleotide sequence set forth in SEQ ID NO:1, wherein the nucleic acid encodes a polypeptide that exhibits terpene hydroxylase and/or terpene oxidase activity (e.g., sesquiterpene oxidase activity, sesquiterpene hydroxylase activity, etc.).

In some embodiments, a subject nucleic acid comprises a nucleotide sequence having at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% nucleotide sequence identity to a stretch of at least about 500, at least about 600, at least about 700, at least about 800, at least about 900, at least about 1000, at least about 1100, at least about 1200, at least about 1300, at least about 1400, or at least about 1450 contiguous nucleotides of the nucleotide sequence set forth in SEQ ID NO:1.

In some embodiments, a subject nucleic acid comprises at least about 500, at least about 600, at least about 700, at least about 800, at least about 900, at least about 1000, at least about 1100, at least about 1200, at least about 1300, at least about 1400, or at least about 1450 contiguous nucleotides of the nucleotide sequence set forth in SEQ ID NO:1. In some embodiments, a subject nucleic acid comprises at least about 500, at least about 600, at least about 700, at least about 800, at least about 900, at least about 1000, at least about 1100, at least about 1200, at least about 1300, at least about 1400, or at least about 1450 contiguous nucleotides of the nucleotide sequence set forth in SEQ ID NO:1, and encodes a polypeptide that exhibits terpene hydroxylase and/or terpene oxidase activity, e.g., sesquiterpene hydroxylase and/or oxidase activity.

In some embodiments, a subject nucleic acid comprises a nucleotide sequence that hybridizes under stringent hybridization conditions to a nucleic acid comprising the nucleotide sequence set forth in SEQ ID NO:1, or a complement thereof.

In some embodiments, a subject nucleic acid comprises a nucleotide sequence encoding a polypeptide comprising an amino acid sequence as depicted in FIG. 2 and as set forth in SEQ ID NO:2. In some embodiments, a subject nucleic acid comprises a nucleotide sequence encoding a polypeptide comprising an amino acid sequence having at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% amino acid sequence identity to the amino acid sequence set forth in SEQ ID NO:2. In some embodiments, a subject nucleic acid comprises a nucleotide sequence encoding a polypeptide comprising an amino acid sequence having at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% amino acid sequence identity to a stretch of at least about 50, at least about 75, at least about 100, at least about 150, at least about 200, at least about 250, at least about 300, at least about 350, at least about 400, at least about 450, or at least about 490 contiguous amino acids of the amino acid sequence set forth in SEQ ID NO:2. In some embodiments, a subject nucleic acid comprises a nucleotide sequence encoding a polypeptide comprising an amino acid sequence having one, two, three, four, five, six, seven, eight, nine, ten, from about 10 to about 15, from about 15 to about 20, or from about 20 to about 25 conservative amino acid substitutions compared to the amino acid sequence set forth in SEQ ID NO:2. In some embodiments, the encoded polypeptide exhibits terpene hydroxylase and/or terpene oxidase activity. In some embodiments, the encoded polypeptide exhibits sesquiterpene oxidase activity. In some embodiments, the encoded polypeptide catalyzes the C12 oxidation of a sesquiterpene substrate. In other embodiments, the encoded polypeptide exhibits sesquiterpene hydroxylase activity.

In some embodiments, a subject nucleic acid comprises a nucleotide sequence encoding a polypeptide comprising at least about 50, at least about 75, at least about 100, at least about 150, at least about 200, at least about 250, at least about 300, at least about 350, at least about 400, at least about 450, or at least about 490 contiguous amino acids of an amino acid sequence having at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:2. In some embodiments, the encoded polypeptide exhibits terpene hydroxylase and/or terpene oxidase activity. In some embodiments, the encoded polypeptide exhibits sesquiterpene oxidase activity. In some embodiments, the encoded polypeptide catalyzes the C12 oxidation of a sesquiterpene substrate. In other embodiments, the encoded polypeptide exhibits sesquiterpene hydroxylase activity.

In some embodiments, a subject nucleic acid comprises the nucleotide sequence depicted in FIG. 9 and set forth in SEQ ID NO:5. In some embodiments, a subject nucleic acid comprises a nucleotide sequence having at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% nucleotide sequence identity to the nucleotide sequence set forth in SEQ ID NO:5. In some embodiments, a subject nucleic acid comprises a nucleotide sequence having one, two, three, four, five, six, seven, eight, nine, ten, from about 10 to about 15, from about 15 to about 20, from about 20 to about 25, or from about 25 to about 50 nucleotide substitutions compared to the nucleotide sequence set forth in SEQ ID NO:5.

In some embodiments, a subject nucleic acid comprises a nucleotide sequence having at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% nucleotide sequence identity to the nucleotide sequence set forth in SEQ ID NO:5, wherein the nucleic acid encodes a polypeptide that exhibits terpene hydroxylase and/or terpene oxidase activity (e.g., sesquiterpene oxidase activity, sesquiterpene hydroxylase activity, etc.).

In some embodiments, a subject nucleic acid comprises a nucleotide sequence having at least about 45%, at least about 50%, at least about 55%, at least about 57%, at least about 60%, at least about 65%, at least about 70%, at least about 75%, at least about 80%, at least about 85%, at least about 90%, at least about 95%, at least about 98%, or at least about 99% nucleotide sequence identity to a stretch of at least about 500, at least about 600, at least about 700, at least about 800, at least about 900, at least about 1000, at least about 1100, at least about 1200, at least about 1300, at least about 1400, or at least about 1450 contiguous nucleotides of the nucleotide sequence set forth in SEQ ID NO:5.

In some embodiments, a subject nucleic acid comprises a nucleotide sequence encoding a polypeptide comprising at least about 50, at least about 75, at least about 100, at least about 150, at least about 200, at least about 250, at least about 300, at least about 350, at least about 400, at least about 450, or at least about 480 contiguous amino acids of an amino acid sequence having at least about 50%, at least about 55%, at least about 60%, at least about 65%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:6. In many embodiments, the encoded polypeptide exhibits terpene hydroxylase and/or terpene oxidase activity. In many embodiments, the encoded polypeptide exhibits sesquiterpene oxidase, or sesquiterpene hydroxylase activity. In many embodiments, the encoded polypeptide catalyzes the hydroxylation of a sesquiterpene substrate.

In some embodiments, a subject nucleic acid comprises at least about 500, at least about 600, at least about 700, at least about 800, at least about 900, at least about 1000, at least about 1100, at least about 1200, at least about 1300, at least about 1400, or at least about 1450 contiguous nucleotides of the nucleotide sequence set forth in SEQ ID NO:5. In some embodiments, a subject nucleic acid comprises at least about 500, at least about 600, at least about 700, at least about 800, at least about 900, at least about 1000, at least about 1100, at least about 1200, at least about 1300, at least about 1400, or at least about 1450 contiguous nucleotides of the nucleotide sequence set forth in SEQ ID NO:5, and encodes a polypeptide that exhibits terpene hydroxylase and/or oxidase activity, e.g., sesquiterpene oxidase activity, sesquiterpene hydroxylase activity, etc.

In some embodiments, a subject nucleic acid comprises a nucleotide sequence that hybridizes under stringent hybridization conditions to a nucleic acid comprising the nucleotide sequence set forth in SEQ ID NO:5, or a complement thereof.

In some embodiments, a subject nucleic acid comprises a nucleotide sequence encoding a polypeptide comprising an amino acid sequence as depicted in FIG. 9 and as set forth in SEQ ID NO:6. In some embodiments, a subject nucleic acid comprises a nucleotide sequence encoding a polypeptide comprising an amino acid sequence having at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% amino acid sequence identity to the amino acid sequence set forth in SEQ ID NO:6. In some embodiments, a subject nucleic acid comprises a nucleotide sequence encoding a polypeptide comprising an amino acid sequence having at least about 45%, at least about 50%, at least about 55%, at least about 60%, at least about 65%, at least about 70%, at least about 75%, at least about 80%, at least about 85%, at least about 90%, at least about 95%, at least about 98%, or at least about 99% amino acid sequence identity to a stretch of at least about 50, at least about 75, at least about 100, at least about 150, at least about 200, at least about 250, at least about 300, at least about 350, at least about 400, at least about 450, or at least about 480 contiguous amino acids of the amino acid sequence as set forth in SEQ ID NO:6. In some embodiments, a subject nucleic acid comprises a nucleotide sequence encoding a polypeptide comprising an amino acid sequence having one, two, three, four, five, six, seven, eight, nine, ten, from about 10 to about 15, from about 15 to about 20, or from about 20 to about 25 conservative amino acid substitutions compared to the amino acid sequence set forth in SEQ ID NO:6. In some embodiments, the encoded polypeptide exhibits terpene hydroxylase and/or terpene oxidase activity. In some embodiments, the encoded polypeptide exhibits sesquiterpene oxidase activity. In some embodiments, the encoded polypeptide catalyzes the hydroxylation of a sesquiterpene substrate. In other embodiments, the encoded polypeptide exhibits sesquiterpene hydroxylase activity.

In some embodiments, a subject nucleic acid comprises a nucleotide sequence encoding a polypeptide comprising at least about 50, at least about 75, at least about 100, at least about 150, at least about 200, at least about 250, at least about 300, at least about 350, at least about 400, at least about 450, or at least about 480 contiguous amino acids of an amino acid sequence having at least about 50%, at least about 55%, at least about 60%, at least about 65%, at least about 70%, at least about 75%, at least about 80%, at least about 85%, at least about 90%, at least about 95%, at least about 98%, at least about 99%, or 100% amino acid sequence identity to the amino acid sequence set forth in SEQ ID NO:6. In some embodiments, the encoded polypeptide exhibits terpene hydroxylase and/or terpene oxidase activity. In some embodiments, the encoded polypeptide exhibits sesquiterpene oxidase activity. In some embodiments, the encoded polypeptide catalyzes the hydroxylation of a sesquiterpene substrate. In other embodiments, the encoded polypeptide exhibits sesquiterpene hydroxylase activity.

In some embodiments, a subject nucleic acid comprises a nucleotide sequence that encodes a variant of a polypeptide comprising an amino acid sequence set forth in SEQ ID NO:2 or SEQ ID NO:6. For example, in some embodiments, a subject nucleic acid comprises a nucleotide sequence encoding an enzyme that exhibits one or more of the following properties compared to an enzyme comprising an amino acid sequence set forth in SEQ ID NO:2 or SEQ ID NO:6: 1) increased enzymatic activity; 2) increased stability in vitro and/or in vivo; 3) increased product yield; 4) altered protein turnover rate; 5) altered substrate specificity (e.g., such that the variant enzyme modifies a selected substrate(s); 6) increased enzyme efficiency (e.g., increased efficiency of substrate conversion to generate product); and 7) increased solubility (e.g., solubility within the cytoplasm or cytosol).

Nucleic Acids Encoding Cytochrome P450 Reductases

The present invention provides an isolated nucleic acid comprising a nucleotide sequence encoding a cytochrome P450 reductase (CPR). In some embodiments, a subject CPR nucleic acid comprises a nucleotide sequence encoding a CPR that transfers electrons from NADPH to a cytochrome P450 oxidase encoded by a subject isoprenoid-modifying enzyme nucleic acid.

In some embodiments, a subject nucleic acid comprises the nucleotide sequence depicted in FIG. 3 and set forth in SEQ ID NO:3. In some embodiments, a subject nucleic acid comprises a nucleotide sequence having at least about 85%, at least about 90%, at least about 95%, at least about 98%, or at least about 99% nucleotide sequence identity to the nucleotide sequence set forth in SEQ ID NO:3.

In some embodiments, a subject nucleic acid comprises a nucleotide sequence that hybridizes under stringent hybridization conditions to a nucleic acid comprising the nucleotide sequence set forth in SEQ ID NO:3, or a complement thereof.

In some embodiments, a subject nucleic acid comprises a nucleotide sequence encoding a polypeptide comprising an amino acid sequence as depicted in FIG. 4 and as set forth in SEQ ID NO:4. In some embodiments, a subject nucleic acid comprises a nucleotide sequence encoding a polypeptide comprising an amino acid sequence having at least about 80%, at least about 85%, at least about 90%, at least about 95%, at least about 98%, or at least about 99% amino acid sequence identity to the amino acid sequence set forth in SEQ ID NO:4. In some embodiments, a subject nucleic acid comprises a nucleotide sequence encoding a polypeptide comprising an amino acid sequence having one, two, three, four, five, six, seven, eight, nine, ten, from about 10 to about 15, from about 15 to about 20, or from about 20 to about 25 conservative amino acid substitutions compared to the amino acid sequence set forth in SEQ ID NO:4.

In some embodiments, a subject nucleic acid comprises a nucleotide sequence encoding a polypeptide comprising at least about 50, at least about 75, at least about 100, at least about 150, at least about 200, at least about 250, at least about 300, at least about 350, at least about 400, at least about 450, at least about 500, at least about 550, at least about 600, at least about 650, or at least about 700 contiguous amino acids of an amino acid sequence having at least about 80%, at least about 85%, at least about 90%, at least about 95%, at least about 98%, at least about 99%, or 100% amino acid sequence identity to the amino acid sequence set forth in SEQ ID NO:4. In some embodiments, the encoded polypeptide transfers electrons from NADPH to a polypeptide (e.g., an isoprenoid-modifying enzyme) encoded by a subject isoprenoid-modifying enzyme nucleic acid.

In some embodiments, a subject nucleic acid comprises at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, or at least about 2100 contiguous nucleotides of the nucleotide sequence set forth in SEQ ID NO:3. In some embodiments, a subject nucleic acid comprises at least about 500, at least about 600, at least about 700, at least about 800, at least about 900, at least about 1000, at least about 1100, at least about 1200, at least about 1300, at least about 1400, at least about 1500, at least about 1600, at least about 1700, at least about 1800, at least about 1900, at least about 2000, or at least about 2100 contiguous nucleotides of the nucleotide sequence set forth in SEQ ID NO:3, and encodes a polypeptide that transfers electrons from NADPH to a cytochrome P450 oxidase encoded by a subject isoprenoid-modifying enzyme nucleic acid, e.g., the encoded polypeptide transfers electrons from NADPH to a polypeptide (e.g., an isoprenoid-modifying enzyme) encoded by a subject isoprenoid-modifying enzyme nucleic acid.

In some embodiments, a subject nucleic acid comprises a nucleotide sequence that encodes a variant of a polypeptide comprising an amino acid sequence set forth in SEQ ID NO:4. For example, in some embodiments, a subject nucleic acid comprises a nucleotide sequence encoding an enzyme that exhibits one or more of the following properties compared to an enzyme comprising an amino acid sequence set forth in SEQ ID NO:4: 1) increased enzymatic activity; 2) increased stability in vitro and/or in vivo; 3) increased product yield; 4) altered protein turnover rate; 5) altered substrate specificity (e.g., such that the variant enzyme modifies a selected substrate(s); 6) increased enzyme efficiency (e.g., increased efficiency of substrate conversion to generate product); and 7) increased solubility (e.g., solubility within the cytoplasm or cytosol).

In some embodiments, a subject nucleic acid comprises a nucleotide sequence encoding a fusion protein that comprises an amino acid sequence of an isoprenoid-modifying enzyme that exhibits terpene hydroxylase and/or terpene oxidase activity, as described above, fused to a heterologous polypeptide (a "fusion partner"), e.g., a polypeptide other than an isoprenoid-modifying enzyme as described above. In some embodiments, a subject nucleic acid comprises a nucleotide sequence encoding a fusion protein that comprises an amino acid sequence of a CPR, as described above, and a heterologous polypeptide, e.g. a polypeptide other than a CPR. Suitable fusion partners include, but are not limited to, polypeptides that enhance solubility of the isoprenoid-modifying enzyme or the CPR; polypeptides that provide for a detectable signal (e.g., a fluorescent protein; an enzyme that yields a detectable product, e.g., β-galactosidase, luciferase, horse radish peroxidase, and the like); polypeptides that provide for inclusion of the isoprenoid-modifying enzyme or the CPR in a particular cellular compartment (e.g., cytosol, cytoplasm, etc.); and the like.

In some embodiments, a subject nucleic acid comprises a nucleotide sequence encoding both an isoprenoid-modifying enzyme (e.g., a polypeptide that exhibits terpene hydroxylase and/or terpene oxidase activity) and a CPR. In some embodiments, a subject nucleic acid comprises a nucleotide sequence encoding a fusion protein that comprises an amino acid sequence of an isoprenoid-modifying enzyme that exhibits terpene hydroxylase and/or terpene oxidase activity, as described above, fused to a CPR polypeptide. In some embodiments, the encoded fusion protein is of the formula $NH_2$-A-X—B—COOH, where A is the isoprenoid-modifying enzyme that exhibits terpene hydroxylase and/or terpene oxidase activity, X is an optional linker, and B is the CPR polypeptide. In some embodiments, the encoded fusion protein is of the formula $NH_2$-A-X—B—COOH, where A is the CPR polypeptide, X is an optional linker, and B is the isoprenoid-modifying polypeptide that exhibits terpene hydroxylase and/or terpene oxidase activity.

The linker peptide may have any of a variety of amino acid sequences. Proteins can be joined by a spacer peptide, generally of a flexible nature, although other chemical linkages are not excluded. The linker may be a cleavable linker. Suitable linker sequences will generally be peptides of between about 5 and about 50 amino acids in length, or between about 6 and about 25 amino acids in length. Peptide linkers with a degree of flexibility will generally be used. The linking peptides may have virtually any amino acid sequence, bearing in mind that the preferred linkers will have a sequence that results in a generally flexible peptide. The use of small amino acids, such as glycine and alanine, are of use in creating a flexible peptide. The creation of such sequences is routine to those of skill in the art. A variety of different linkers are commercially available and are considered suitable for use according to the present invention.

Suitable linker peptides frequently include amino acid sequences rich in alanine and proline residues, which are known to impart flexibility to a protein structure. Exemplary linkers have a combination of glycine, alanine, proline and methionine residues, such as AAAGGM (SEQ ID NO: 8); AAAGGMPPAAAGGM (SEQ ID NO:9); AAAGGM (SEQ ID NO:10); and PPAAAGGM (SEQ ID NO:11). Other exemplary linker peptides include IEGR (SEQ ID NO:12; and GGKGGK (SEQ ID NO:13). However, any flexible linker generally between about 5 and about 50 amino acids in length may be used. Linkers may have virtually any sequence that results in a generally flexible peptide, including alanine-proline rich sequences of the type exemplified above.

Constructs

The present invention further provides recombinant vectors ("constructs") comprising a subject nucleic acid. In some embodiments, a subject recombinant vector provides for amplification of a subject nucleic acid. In some embodiments, a subject recombinant vector provides for production of an encoded isoprenoid-modifying enzyme, or an encoded CPR, in a eukaryotic cell, in a prokaryotic cell, or in a cell-free transcription/translation system. Suitable expression vectors include, but are not limited to, baculovirus vectors, bacteriophage vectors, plasmids, phagemids, cosmids, fosmids, bacterial artificial chromosomes, viral vectors (e.g. viral vectors based on vaccinia virus, poliovirus, adenovirus, adeno-associated virus, SV40, herpes simplex virus, and the like), P1-based artificial chromosomes, yeast plasmids, yeast artificial chromosomes, and any other vectors specific for specific hosts of interest (such as *E. coli*, yeast, and plant cells).

In some embodiments, a subject recombinant vector comprises a subject isoprenoid-modifying enzyme-encoding nucleic acid and a subject CPR-encoding nucleic acid. In some of these embodiments, a subject recombinant vector is an expression vector that provides for production of both the encoded isoprenoid-modifying enzyme and the encoded CPR in a eukaryotic cell, in a prokaryotic cell, or in a cell-free transcription/translation system.

Certain types of vectors allow the expression cassettes of the present invention to be amplified. Other types of vectors are necessary for efficient introduction of subject nucleic acid to cells and their stable expression once introduced. Any vector capable of accepting a subject nucleic acid is contemplated as a suitable recombinant vector for the purposes of the invention. The vector may be any circular or linear length of DNA that either integrates into the host genome or is maintained in episomal form. Vectors may require additional manipulation or particular conditions to be efficiently incorporated into a host cell (e.g., many expression plasmids), or can be part of a self-integrating, cell specific system (e.g., a recombinant virus). The vector is in some embodiments functional in a prokaryotic cell, where such vectors function to propagate the recombinant vector and/or provide for expression of a subject nucleic acid. The vector is in some embodiments functional in a eukaryotic cell, where the vector will in many embodiments be an expression vector.

Numerous suitable expression vectors are known to those of skill in the art, and many are commercially available. The following vectors are provided by way of example; for bacterial host cells: pBluescript (Stratagene, San Diego, Calif.), pQE vectors (Qiagen), pBluescript plasmids, pNH vectors, lambda-ZAP vectors (Stratagene); pTrc (Amann et al., Gene, 69:301-315 (1988)); pTrc99a, pKK223-3, pDR540, and pRIT2T (Pharmacia); for eukaryotic host cells: pXT1, pSG5 (Stratagene), pSVK3, pBPV, pMSG, and pSVLSV40 (Pharmacia). However, any other plasmid or other vector may be used so long as it is compatible with the host cell.

A subject recombinant vector will in many embodiments contain one or more selectable marker genes to provide a phenotypic trait for selection of transformed host cells. Suitable selectable markers include, but are not limited to, dihydrofolate reductase, neomycin resistance for eukaryotic cell culture; and tetracycline or ampicillin resistance in prokaryotic host cells such as E. coli.

In many embodiments, a subject nucleic acid comprises a nucleotide sequence encoding an isoprenoid-modifying enzyme, where the isoprenoid-modifying enzyme-encoding nucleotide sequence is operably linked to one or more transcriptional and/or translational control elements. In many embodiments, a subject nucleic acid comprises a nucleotide sequence encoding a CPR, where the CPR-encoding nucleotide sequence is operably linked to one or more transcriptional and/or translational control elements.

In some embodiments, as noted above, a subject recombinant vector comprises a subject isoprenoid-modifying enzyme-encoding nucleic acid and a subject CPR-encoding nucleic acid. In some of these embodiments, the isoprenoid-modifying enzyme-encoding nucleotide sequence and the CPR-encoding nucleotide sequence are operably linked to different transcriptional control elements. In other embodiments, the isoprenoid-modifying enzyme-encoding nucleotide sequence and the CPR-encoding nucleotide sequence are operably linked to the same transcriptional control element(s). In some embodiments, the isoprenoid-modifying enzyme-encoding nucleotide sequence and the CPR-encoding nucleotide sequence are both operably linked to the same inducible promoter. In some embodiments, the isoprenoid-modifying enzyme-encoding nucleotide sequence and the CPR-encoding nucleotide sequence are both operably linked to the same constitutive promoter.

Suitable promoters for use in prokaryotic host cells include, but are not limited to, a bacteriophage T7 RNA polymerase promoter; a trp promoter; a lac operon promoter; a hybrid promoter; e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, J. Bacteriol., 1991: 173(1): 86-93; Alpuche-Aranda et al., PNAS, 1992; 89(21): 10079-83), a nirB promoter (Harborne et al. (1992) Mol. Micro. 6:2805-2813), and the like (see, e.g., Dunstan et al. (1999) Infect. Immun. 67:5133-5141; McKelvie et al. (2004) Vaccine 22:3243-3255; and Chatfield et al. (1992) Biotechnol. 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spv promoter, and the like; a promoter derived from the pathogenicity island SPI-2 (see, e.g., WO96/17951); an actA promoter (see, e.g., Shetron-Rama et al. (2002) Infect. Immun. 70:1087-1096); an rpsM promoter (see, e.g., Valdivia and Falkow (1996). Mol. Microbiol. 22:367-378); a tet promoter (see, e.g., Hillen, W. and Wissmann, A. (1989) In Saenger, W. and Heinemann, U. (eds), Topics in Molecular and Structural Biology, Protein-Nucleic Acid Interaction. Macmillan, London, UK, Vol. 10, pp. 143-162); an SP6 promoter (see, e.g., Melton et al. (1984) Nucl. Acids Res. 12:7035-7056); and the like.

Non-limiting examples of suitable eukaryotic promoters include CMV immediate early, HSV thymidine kinase, early and late SV40, LTRs from retrovirus, and mouse metallothionein-I. In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PHO5 promoter, a CUP1 promoter, a GAL7 promoter, a MET25 promoter, a MET3 promoter, and the like. Selection of the appropriate vector and promoter is well within the level of ordinary skill in the art. The expression vector may also contain a ribosome binding site for translation initiation and a transcription terminator. The expression vector may also include appropriate sequences for amplifying expression.

In many embodiments, a nucleotide sequence encoding an isoprenoid modifying enzyme is operably linked to an inducible promoter. In many embodiments, a nucleotide sequence encoding a CPR is operably linked to an inducible promoter. Inducible promoters are well known in the art. Suitable inducible promoters include, but are not limited to, the pL of bacteriophage λ; Plac; Ptrp; Ptac (Ptrp-lac hybrid promoter); an isopropyl-beta-D-thiogalactopyranoside (IPTG)-inducible promoter, e.g., a lacZ promoter; a tetracycline-inducible promoter; an arabinose inducible promoter, e.g., $P_{BAD}$ (see, e.g., Guzman et al. (1995) J. Bacteria 177:4121-4130); a xylose-inducible promoter, e.g., Pxyl (see, e.g., Kim et al. (1996) Gene 181:71-76); a GAL1 promoter; a tryptophan promoter; a lac promoter; an alcohol-inducible promoter, e.g., a methanol-inducible promoter, an ethanol-inducible promoter; a raffinose-inducible promoter; a heat-inducible promoter, e.g., heat inducible lambda $P_L$ promoter, a promoter controlled by a heat-sensitive repressor (e.g., CI857-repressed lambda-based expression vectors; see, e.g., Hoffmann et al. (1999) FEMS Microbiol Lett. 177(2):327-34); and the like.

In yeast, a number of vectors containing constitutive or inducible promoters may be used. For a review see, Current Protocols in Molecular Biology, Vol. 2, 1988, Ed. Ausubel, et al., Greene Publish. Assoc. & Wiley Interscience, Ch. 13; Grant, et al., 1987, Expression and Secretion Vectors for Yeast, in Methods in Enzymology, Eds. Wu & Grossman, 31987, Acad. Press, N.Y., Vol. 153, pp. 516-544; Glover, 1986, DNA Cloning, Vol. II, IRL Press, Wash., D.C., Ch. 3; and Bitter, 1987, Heterologous Gene Expression in Yeast, Methods in Enzymology, Eds. Berger & Kimmel, Acad.

Press, N.Y., Vol. 152, pp. 673-684; and The Molecular Biology of the Yeast *Saccharomyces,* 1982, Eds. Strathern et al., Cold Spring Harbor Press, Vols. I and II. A constitutive yeast promoter such as ADH or LEU2 or an inducible promoter such as GAL may be used (Cloning in Yeast, Ch. 3, R. Rothstein In: DNA Cloning Vol. 11, A Practical Approach, Ed. DM Glover, 1986, IRL Press, Wash., D.C.). Alternatively, vectors may be used which promote integration of foreign DNA sequences into the yeast chromosome.

In some embodiments, a subject nucleic acid or a subject vector comprises a promoter or other regulatory element(s) for expression in a plant cell. Non-limiting examples of suitable constitutive promoters that are functional in a plant cell is the cauliflower mosaic virus 35S promoter, a tandem 35S promoter (Kay et al., *Science* 236:1299 (1987)), a cauliflower mosaic virus 19S promoter, a nopaline synthase gene promoter (Singer et al., *Plant Mol. Biol.* 14:433 (1990); An, *Plant Physiol.* 81:86 (1986), an octopine synthase gene promoter, and a ubiquitin promoter. Suitable inducible promoters that are functional in a plant cell include, but are not limited to, a phenylalanine ammonia-lyase gene promoter, a chalcone synthase gene promoter, a pathogenesis-related protein gene promoter, a copper-inducible regulatory element (Mett et al., *Proc. Natl. Acad. Sci. USA* 90:4567-4571 (1993); Furst et al., *Cell* 55:705-717 (1988)); tetracycline and chlor-tetracycline-inducible regulatory elements (Gatz et al., *Plant J.* 2:397-404 (1992); Röder et al., *Mol. Gen. Genet.* 243:32-38 (1994); Gatz, *Meth. Cell Biol.* 50:411-424 (1995)); ecdysone inducible regulatory elements (Christopherson et al., *Proc. Natl. Acad. Sci. USA* 89:6314-6318 (1992); Kreutzweiser et al., *Ecotoxicol. Environ. Safety* 28:14-24 (1994)); heat shock inducible regulatory elements (Takahashi et al., *Plant Physiol.* 99:383-390 (1992); Yabe et al., *Plant Cell Physiol.* 35:1207-1219 (1994); Ueda et al., *Mol. Gen. Genet.* 250:533-539 (1996)); and lac operon elements, which are used in combination with a constitutively expressed lac repressor to confer, for example, IPTG-inducible expression (Wilde et al., *EMBO J.* 11:1251-1259 (1992); a nitrate-inducible promoter derived from the spinach nitrite reductase gene (Back et al., *Plant Mol. Biol.* 17:9 (1991)); a light-inducible promoter, such as that associated with the small subunit of RuBP carboxylase or the LHCP gene families (Feinbaum et al., *Mol. Gen. Genet.* 226:449 (1991); Lam and Chua, *Science* 248:471 (1990)); a light-responsive regulatory element as described in U.S. Patent Publication No. 20040038400; a salicylic acid inducible regulatory elements (Uknes et al., *Plant Cell* 5:159-169 (1993); Bi et al., *Plant J.* 8:235-245 (1995)); plant hormone-inducible regulatory elements (Yamaguchi-Shinozaki et al., *Plant Mol. Biol.* 15:905 (1990); Kares et al., *Plant Mol. Biol.* 15:225 (1990)); and human hormone-inducible regulatory elements such as the human glucocorticoid response element (Schena et al., *Proc. Natl. Acad. Sci. USA* 88:10421 (1991).

Plant tissue-selective regulatory elements also can be included in a subject nucleic acid or a subject vector. Suitable tissue-selective regulatory elements, which can be used to ectopically express a nucleic acid in a single tissue or in a limited number of tissues, include, but are not limited to, a xylem-selective regulatory element, a tracheid-selective regulatory element, a fiber-selective regulatory element, a trichome-selective regulatory element (see, e.g., Wang et al. (2002) *J. Exp. Botany* 53:1891-1897), a glandular trichome-selective regulatory element, and the like.

Vectors that are suitable for use in plant cells are known in the art, and any such vector can be used to introduce a subject nucleic acid into a plant host cell. Suitable vectors include, e.g., a Ti plasmid of *Agrobacterium tumefaciens* or an $Ri_1$ plasmid of *A. rhizogenes*. The Ti or $Ri_1$ plasmid is transmitted to plant cells on infection by *Agrobacterium* and is stably integrated into the plant genome. J. Schell, *Science,* 237: 1176-83 (1987). Also suitable for use is a plant artificial chromosome, as described in, e.g., U.S. Pat. No. 6,900,012.

Compositions

The present invention further provides compositions comprising a subject nucleic acid. The present invention further provides compositions comprising a subject recombinant vector. Compositions comprising a subject nucleic acid or a subject expression vector will in many embodiments include one or more of: a salt, e.g., NaCl, MgCl, KCl, $MgSO_4$, etc.; a buffering agent, e.g., a Tris buffer, N-(2-Hydroxyethyl)piperazine-N'-(2-ethanesulfonic acid) (HEPES), 2-(N-Morpholino)ethanesulfonic acid (MES), 2-(N-Morpholino) ethanesulfonic acid sodium salt (MES), 3-(N-Morpholino) propanesulfonic acid (MOPS), N-tris[Hydroxymethyl] methyl-3-aminopropanesulfonic acid (TAPS), etc.; a solubilizing agent; a detergent, e.g., a non-ionic detergent such as Tween-20, etc.; a nuclease inhibitor; and the like. In some embodiments, a subject nucleic acid or a subject recombinant vector is lyophilized.

Host Cells

The present invention provides genetically modified host cells, e.g., host cells that have been genetically modified with a subject nucleic acid or a subject recombinant vector. In many embodiments, a subject genetically modified host cell is an in vitro host cell. In other embodiments, a subject genetically modified host cell is an in vivo host cell. In other embodiments, a subject genetically modified host cell is part of a multicellular organism.

Host cells are in many embodiments unicellular organisms, or are grown in culture as single cells. In some embodiments, the host cell is a eukaryotic cell. Suitable eukaryotic host cells include, but are not limited to, yeast cells, insect cells, plant cells, fungal cells, and algal cells. Suitable eukaryotic host cells include, but are not limited to, *Pichia pastoris, Pichia finlandica, Pichia trehalophila, Pichia koclamae, Pichia membranaefaciens, Pichia opuntiae, Pichia thermotolerans, Pichia salictaria, Pichia guercuum, Pichia pijperi, Pichia stiptis, Pichia methanolica, Pichia* sp., *Saccharomyces cerevisiae, Saccharomyces* sp., *Hansenula polymorpha, Kluyveromyces* sp., *Kluyveromyces lactis, Candida albicans, Aspergillus nidulans, Aspergillus niger, Aspergillus oryzae, Trichoderma reesei, Chrysosporium lucknowense, Fusarium* sp., *Fusarium gramineum, Fusarium venenatum, Neurospora crassa, Chlamydomonas reinhardtii,* and the like. In some embodiments, the host cell is a eukaryotic cell other than a plant cell.

In other embodiments, the host cell is a plant cell. Plant cells include cells of monocotyledons ("monocots") and dicotyledons ("dicots").

In other embodiments, the host cell is a prokaryotic cell. Suitable prokaryotic cells include, but are not limited to, any of a variety of laboratory strains of *Escherichia coli, Lactobacillus* sp., *Salmonella* sp., *Shigella* sp., and the like. See, e.g., Carrier et al. (1992) *J. Immunol.* 148:1176-1181; U.S. Pat. No. 6,447,784; and Sizemore et al. (1995) *Science* 270: 299-302. Examples of *Salmonella* strains which can be employed in the present invention include, but are not limited to, *Salmonella typhi* and *S. typhimurium*. Suitable *Shigella* strains include, but are not limited to, *Shigella flexneri, Shigella sonnei,* and *Shigella disenteriae*. Typically, the laboratory strain is one that is non-pathogenic. Non-limiting examples of other suitable bacteria include, but are not limited to, *Bacillus subtilis, Pseudomonas pudita, Pseudomonas aeruginosa, Pseudomonas mevalonii, Rhodobacter* sphaeroides, Rhodobacter capsulatus, Rhodospirillum rubrum, Rhodococcus sp., and the like. In some embodiments, the host cell is *Escherichia coli*.

To generate a subject genetically modified host cell, a subject nucleic acid comprising nucleotide sequences encoding an isoprenoid-modifying enzyme is introduced stably or transiently into a parent host cell, using established techniques, including, but not limited to, electroporation, calcium phosphate precipitation, DEAE-dextran mediated transfection, liposome-mediated transfection, and the like. For stable transformation, a nucleic acid will generally further include a selectable marker, e.g., any of several well-known selectable markers such as neomycin resistance, ampicillin resistance, tetracycline resistance, chloramphenicol resistance, kanamycin resistance, and the like.

In some embodiments, a subject genetically modified host cell is a plant cell. A subject genetically modified plant cell is useful for producing a selected isoprenoid compound in in vitro plant cell culture. Guidance with respect to plant tissue culture may be found in, for example: Plant Cell and Tissue Culture, 1994, Vasil and Thorpe Eds., Kluwer Academic Publishers; and in: Plant Cell Culture Protocols (Methods in Molecular Biology 111), 1999, Hall Eds, Humana Press.

Genetically Modified Host Cells

In some embodiments, a subject genetically modified host cell comprises a subject expression vector, where the subject expression vector comprises a nucleotide sequence encoding an isoprenoid-modifying enzyme. In some embodiments, a subject genetically modified host cell comprises a subject expression vector, where the subject expression vector comprises a nucleotide sequence encoding a polypeptide that exhibits terpene hydroxylase and/or terpene oxidase activity.

In some embodiments, a subject genetically modified host cell comprises a first subject expression vector, where the first subject expression vector comprises a subject nucleic acid comprising a nucleotide sequence encoding a polypeptide that exhibits terpene hydroxylase and/or terpene oxidase activity; and further comprises a second subject expression vector, where the second subject expression vector comprises a subject nucleic acid comprising a nucleotide sequence encoding a CPR. In other embodiments, a subject genetically modified host cell comprises a subject expression vector, wherein the subject expression vector comprises subject nucleic acid comprising a nucleotide sequence encoding an isoprenoid-modifying enzyme and a subject nucleic acid comprising a nucleotide sequence encoding a CPR. In other embodiments, a subject genetically modified host cell comprises a subject expression vector, where the subject expression vector comprises a subject nucleic acid comprising a nucleotide sequence encoding a fusion polypeptide (e.g. a polypeptide that includes an isoprenoid-modifying enzyme and a CPR).

Suitable CPR-encoding nucleic acids include nucleic acids encoding CPR found in plants. Suitable CPR-encoding nucleic acids include nucleic acids encoding CPR found in fungi. Examples of suitable CPR-encoding nucleic acids include: GenBank Accession No. AJ303373 (*Triticum aestivum* CPR); GenBank Accession No. AY959320 (*Taxus chinensis* CPR); GenBank Accession No. AY532374 (*Ammi majus* CPR); GenBank Accession No. AG211221 (*Oryza sativa* CPR); and GenBank Accession No. AF024635 (*Petroselinum crispum* CPR).

In some embodiments, a subject genetically modified host cell is a host cell that does not normally synthesize isopentenyl pyrophosphate (IPP) or mevalonate via a mevalonate pathway. The mevalonate pathway comprises: (a) condensing two molecules of acetyl-CoA to acetoacetyl-CoA; (b) condensing acetoacetyl-CoA with acetyl-CoA to form HMG-CoA; (c) converting HMG-CoA to mevalonate; (d) phosphorylating mevalonate to mevalonate 5-phosphate; (e) converting mevalonate 5-phosphate to mevalonate 5-pyrophosphate; and (f) converting mevalonate 5-pyrophosphate to isopentenyl pyrophosphate. The mevalonate pathway enzymes required for production of IPP vary, depending on the culture conditions.

As noted above, in some embodiments, a subject genetically modified host cell is a host cell that does not normally synthesize isopentenyl pyrophosphate (IPP) or mevalonate via a mevalonate pathway. In some of these embodiments, the host cell is genetically modified with a subject expression vector comprising a subject nucleic acid encoding an isoprenoid-modifying enzyme; and the host cell is genetically modified with one or more heterologous nucleic acids comprising nucleotide sequences encoding acetoacetyl-CoA thiolase, hydroxymethylglutaryl-CoA synthase (HMGS), hydroxymethylglutaryl-CoA reductase (HMGR), mevalonate kinase (MK), phosphomevalonate kinase (PMK), and mevalonate pyrophosphate decarboxylase (MPD) (and optionally also IPP isomerase). In many of these embodiments, the host cell is genetically modified with an expression vector comprising a nucleotide sequence encoding a CPR. In some of these embodiments, the host cell is genetically modified with a subject expression vector comprising a subject nucleic acid encoding an isoprenoid-modifying enzyme; and the host cell is genetically modified with one or more heterologous nucleic acids comprising nucleotide sequences encoding MK, PMK, MPD (and optionally also IPP isomerase). In many of these embodiments, the host cell is genetically modified with an expression vector comprising a nucleotide sequence encoding a CPR.

In some embodiments, a subject genetically modified host cell is a host cell that does not normally synthesize IPP or mevalonate via a mevalonate pathway; the host cell is genetically modified with a subject expression vector comprising a subject nucleic acid encoding an isoprenoid-modifying enzyme; and the host cell is genetically modified with one or more heterologous nucleic acids comprising nucleotide sequences encoding acetoacetyl-CoA thiolase, HMGS, HMGR, MK, PMK, MPD, IPP isomerase, and a prenyl transferase. In many of these embodiments, the host cell is genetically modified with an expression vector comprising a nucleotide sequence encoding a CPR. In some embodiments, a subject genetically modified host cell is a host cell that does not normally synthesize IPP or mevalonate via a mevalonate pathway; the host cell is genetically modified with a subject expression vector comprising a subject nucleic acid encoding an isoprenoid-modifying enzyme; and the host cell is genetically modified with one or more heterologous nucleic acids comprising nucleotide sequences encoding MK, PMK, MPD, IPP isomerase, and a prenyl transferase. In many of these embodiments, the host cell is genetically modified with an expression vector comprising a nucleotide sequence encoding a CPR.

In some embodiments, a subject genetically modified host cell is one that normally synthesizes IPP or mevalonate via a mevalonate pathway, e.g., the host cell is one that comprises an endogenous mevalonate pathway. In some of these embodiments, the host cell is a yeast cell. In some of these embodiments, the host cell is *Saccharomyces cerevisiae*.

In some embodiments, a subject genetically modified host cell is further genetically modified with one or more nucleic acids that comprise nucleotide sequences encoding a dehydrogenase or dehydrogenases, which dehydrogenase further modifies an isoprenoid compound. The encoded dehydrogenase may be one that is naturally found in a prokaryotic cell or a eukaryotic cell, or may be a variant of such a dehydrogenase. In some embodiments, the present invention provides isolated nucleic acids comprising nucleotide sequences encoding such dehydrogenases.

Mevalonate Pathway Nucleic Acids

Nucleotide sequences encoding MEV pathway gene products are known in the art, and any known MEV pathway gene product-encoding nucleotide sequence can used to generate a subject genetically modified host cell. For example, nucleotide sequences encoding acetoacetyl-CoA thiolase, HMGS, HMGR, MK, PMK, MPD, and IDI are known in the art. The following are non-limiting examples of known nucleotide sequences encoding MEV pathway gene products, with GenBank Accession numbers and organism following each MEV pathway enzyme, in parentheses: acetoacetyl-CoA thiolase: (NC_000913 REGION: 2324131 . . . 2325315; *E. coli*), (D49362; *Paracoccus denitrificans*), and (L20428; *Saccharomyces cerevisiae*); HMGS: (NC_001145. complement 19061 . . . 20536; *Saccharomyces cerevisiae*), (X96617; *Saccharomyces cerevisiae*), (X83882; *Arabidopsis thaliana*), (AB037907; *Kitasatospora griseola*), and (BT007302; *Homo sapiens*); HMGR: (NM_206548; *Drosophila melanogaster*), (NM_204485; *Gallus gallus*), (AB015627; *Streptomyces* sp. KO-3988), (AF542543; *Nicotiana attenuata*), (AB037907; *Kitasatospora griseola*), (AX128213, providing the sequence encoding a truncated HMGR; *Saccharomyces cerevisiae*), and (NC_001145: complement (115734 . . . 118898; *Saccharomyces cerevisiae*)); MK: (L77688; *Arabidopsis thaliana*), and (X55875; *Saccharomyces cerevisiae*); PMK: (AF429385; *Hevea brasiliensis*), (NM_006556; *Homo sapiens*), (NC_001145. complement 712315 . . . 713670; *Saccharomyces cerevisiae*); MPD: (X97557; *Saccharomyces cerevisiae*), (AF290095; *Enterococcus faecium*), and (U49260; *Homo sapiens*); and IDI: (NC_000913, 3031087 . . . 3031635; *E. coli*), and (AF082326; *Haematococcus pluvialis*).

In some embodiments, the HMGR coding region encodes a truncated form of HMGR ("tHMGR") that lacks the transmembrane domain of wild-type HMGR. The transmembrane domain of HMGR contains the regulatory portions of the enzyme and has no catalytic activity.

The coding sequence of any known MEV pathway enzyme may be altered in various ways known in the art to generate targeted changes in the amino acid sequence of the encoded enzyme. The amino acid of a variant MEV pathway enzyme will usually be substantially similar to the amino acid sequence of any known MEV pathway enzyme, i.e. will differ by at least one amino acid, and may differ by at least two, at least 5, at least 10, or at least 20 amino acids, but typically not more than about fifty amino acids. The sequence changes may be substitutions, insertions or deletions. For example, as described below, the nucleotide sequence can be altered for the codon bias of a particular host cell. In addition, one or more nucleotide sequence differences can be introduced that result in conservative amino acid changes in the encoded protein.

Prenyl Transferases

In some embodiments, a subject genetically modified host cell is genetically modified to include a nucleic acid comprising a nucleotide sequence encoding an isoprenoid-modifying enzyme; and in some embodiments is also genetically modified to include one or more nucleic acids comprising a nucleotide sequence(s) encoding one or more mevalonate pathway enzymes, as described above; and a nucleic acid comprising a nucleotide sequence that encodes a prenyl transferase.

Prenyltransferases constitute a broad group of enzymes catalyzing the consecutive condensation of IPP resulting in the formation of prenyl diphosphates of various chain lengths. Suitable prenyltransferases include enzymes that catalyze the condensation of IPP with allylic primer substrates to form isoprenoid compounds with from about 2 isoprene units to about 6000 isoprene units or more, e.g., 2 isoprene units (Geranyl Pyrophosphate synthase), 3 isoprene units (Farnesyl pyrophosphate synthase), 4 isoprene units (geranylgeranyl pyrophosphate synthase), 5 isoprene units, 6 isoprene units (hexadecylpyrophosphate synthase), 7 isoprene units, 8 isoprene units (phytoene synthase, octaprenyl pyrophosphate synthase), 9 isoprene units (nonaprenyl pyrophosphate synthase, 10 isoprene units (decaprenyl pyrophosphate synthase), from about 10 isoprene units to about 15 isoprene units, from about 15 isoprene units to about 20 isoprene units, from about 20 isoprene units to about 25 isoprene units, from about 25 isoprene units to about 30 isoprene units, from about 30 isoprene units to about 40 isoprene units, from about 40 isoprene units to about 50 isoprene units, from about 50 isoprene units to about 100 isoprene units, from about 100 isoprene units to about 250 isoprene units, from about 250 isoprene units to about 500 isoprene units, from about 500 isoprene units to about 1000 isoprene units, from about 1000 isoprene units to about 2000 isoprene units, from about 2000 isoprene units to about 3000 isoprene units, from about 3000 isoprene units to about 4000 isoprene units, from about 4000 isoprene units to about 5000 isoprene units, or from about 5000 isoprene units to about 6000 isoprene units or more.

Suitable prenyltransferases include, but are not limited to, an E-isoprenyl diphosphate synthase, including, but not limited to, geranyl diphosphate (GPP) synthase, farnesyl diphosphate (FPP) synthase, geranylgeranyl diphosphate (GGPP) synthase, hexaprenyl diphosphate (HexPP) synthase, heptaprenyl diphosphate (HepPP) synthase, octaprenyl (OPP) diphosphate synthase, solanesyl diphosphate (SPP) synthase, decaprenyl diphosphate (DPP) synthase, chicle synthase, and gutta-percha synthase; and a Z-isoprenyl diphosphate synthase, including, but not limited to, nonaprenyl diphosphate (NPP) synthase, undecaprenyl diphosphate (UPP) synthase, dehydrodolichyl diphosphate synthase, eicosaprenyl diphosphate synthase, natural rubber synthase, and other Z-isoprenyl diphosphate synthases.

The nucleotide sequences of a numerous prenyl transferases from a variety of species are known, and can be used or modified for use in generating a subject genetically modified host cell. Nucleotide sequences encoding prenyl transferases are known in the art. See, e.g., Human farnesyl pyrophosphate synthetase mRNA (GenBank Accession No. J05262; *Homo sapiens*); farnesyl diphosphate synthetase (FPP) gene (GenBank Accession No. J05091; *Saccharomyces cerevisiae*); isopentenyl diphosphate:dimethylallyl diphosphate isomerase gene (J05090; *Saccharomyces cerevisiae*); Wang and Ohnuma (2000) *Biochim. Biophys. Acta* 1529:33-48; U.S. Pat. No. 6,645,747; *Arabidopsis thaliana* farnesyl pyrophosphate synthetase 2 (FPS2)/FPP synthetase 2/farnesyl diphosphate synthase 2 (At4g17190) mRNA (GenBank Accession No. NM_202836); *Ginkgo biloba* geranylgeranyl diphosphate synthase (ggpps) mRNA (GenBank Accession No. AY371321); *Arabidopsis thaliana* geranylgeranyl pyrophosphate synthase (GGPS1)/GGPP synthetase/farnesyltranstransferase (At4g36810) mRNA (GenBank Accession No. NM_119845); *Synechococcus elongatus* gene for farnesyl, geranylgeranyl, geranylfarnesyl, hexaprenyl, heptaprenyl diphosphate synthase (SelF-HepPS) (GenBank Accession No. AB016095); etc.

Terpene Synthases

In some embodiments, a subject genetically modified host cell is genetically modified to include a nucleic acid comprising a nucleotide sequence encoding a terpene synthase. In some embodiments, the terpene synthase is one that modifies FPP to generate a sesquiterpene. In other embodiments, the terpene synthase is one that modifies GPP to generate a monoterpene. In other embodiments, the terpene synthase is one that modifies GGPP to generate a diterpene.

Nucleotide sequences encoding terpene synthases are known in the art, and any known terpene synthase-encoding nucleotide sequence can be used to genetically modify a host cell. For example, the following terpene synthase-encoding nucleotide sequences, followed by their GenBank accession numbers and the organisms in which they were identified, are known and can be used: (−)-germacrene D synthase mRNA (AY438099; *Populus balsamifera* subsp. *trichocarpa×Populus deltoids*); E,E-alpha-farnesene synthase mRNA (AY640154; *Cucumis sativus*); 1,8-cineole synthase mRNA (AY691947; *Arabidopsis thaliana*); terpene synthase 5 (TPS5) mRNA (AY518314; *Zea mays*); terpene synthase 4 (TPS4) mRNA (AY518312; *Zea mays*); myrcene/ocimene synthase (TPS10) (At2g24210) mRNA (NM_127982; *Arabidopsis thaliana*); geraniol synthase (GES) mRNA (AY362553; *Ocimum basilicum*); pinene synthase mRNA (AY237645; *Picea sitchensis*); myrcene synthase 1e20 mRNA (AY195609; *Antirrhinum majus*); (E)-β-ocimene synthase (0e23) mRNA (AY195607; *Antirrhinum majus*); E-β-ocimene synthase mRNA (AY151086; *Antirrhinum majus*); terpene synthase mRNA (AF497492; *Arabidopsis thaliana*); (−)-camphene synthase (AG6.5) mRNA (U87910; *Abies grandis*); (−)-4S-limonene synthase gene (e.g., genomic sequence) (AF326518; *Abies grandis*); delta-selinene synthase gene (AF326513; *Abies grandis*); amorpha-4,11-diene synthase mRNA (AJ251751; *Artemisia annua*); E-α-bisabolene synthase mRNA (AF006195; *Abies grandis*); gamma-humulene synthase mRNA (U92267; *Abies grandis*); δ-selinene synthase mRNA (U92266; *Abies grandis*); pinene synthase (AG3.18) mRNA (U87909; *Abies grandis*); myrcene synthase (AG2.2) mRNA (U87908; *Abies grandis*); etc.

Codon Usage

In some embodiments, a nucleotide sequence used to generate a subject genetically modified host cell is modified such that the nucleotide sequence reflects the codon preference for the particular host cell. For example, the nucleotide sequence will in some embodiments be modified for yeast codon preference. See, e.g., Bennetzen and Hall (1982). *J. Biol. Chem.* 257(6): 3026-3031. As another non-limiting example, the nucleotide sequence will in other embodiments be modified for *E. coli* codon preference. See, e.g., Gouy and Gautier (1982) *Nucleic Acids Res.* 10(22):7055-7074; Eyre-Walker (1996) *Mol. Biol. Evol.* 13(6):864-872. See also Nakamura et al. (2000) *Nucleic Acids Res.* 28(1):292.

Additional Genetic Modifications

In some embodiments, a subject genetically modified host cell is one that is genetically modified to include one or more nucleic acids comprising a nucleotide sequence(s) that encode an isoprenoid-modifying enzyme; and that is further genetically modified to achieve enhanced production of a terpene biosynthetic pathway intermediate, and/or that is further genetically modified such that an endogenous terpene biosynthetic pathway gene is functionally disabled. The term "functionally disabled," as used herein in the context of an endogenous terpene biosynthetic pathway gene, refers to a genetic modification of a terpene biosynthetic pathway gene, which modification results in production of a gene product encoded by the gene that is produced at below normal levels, and/or is non-functional.

Genetic modifications that enhance production of an endogenous terpene biosynthetic pathway intermediate include, but are not limited to, genetic modifications that result in a reduced level and/or activity of a phosphotransacetylase in the host cell. The intracellular concentration of a terpene biosynthetic pathway intermediate is enhanced by increasing the intracellular concentration of acetyl-CoA. *E. coli* secretes a significant fraction of intracellular acetyl-CoA in the form of acetate into the medium. Deleting the gene encoding phosphotransacetylase, pta, the first enzyme responsible for transforming acetyl-CoA into acetate, reduces acetate secretion. Genetic modifications that reduce the level and/or activity of phosphotransacetylase in a prokaryotic host cell are particularly useful where the genetically modified host cell is one that is genetically modified with a nucleic acid comprising nucleotide sequences encoding one or more MEV pathway gene products.

In some embodiments, a genetic modification that results in a reduced level of phosphotransacetylase in a prokaryotic host cell is a genetic mutation that functionally disables the prokaryotic host cell's endogenous pta gene encoding the phosphotransacetylase. The pta gene can be functionally disabled in any of a variety of ways, including insertion of a mobile genetic element (e.g., a transposon, etc.); deletion of all or part of the gene, such that the gene product is not made, or is truncated and is non-functional in converting acetyl-CoA to acetate; mutation of the gene such that the gene product is not made, or is truncated and is non-functional in converting acetyl-CoA to acetate; deletion or mutation of one or more control elements that control expression of the pta gene such that the gene product is not made; and the like.

In some embodiments, the endogenous pta gene of a genetically modified host cell is deleted. Any method for deleting a gene can be used. One non-limiting example of a method for deleting a pta gene is by use of the λRed recombination system. Datsenko and Wanner (2000) *Proc Natl Acad Sci USA* 97(12): p. 6640-5. The pta gene will in some embodiments be deleted from a host cell (e.g., *E. coli*) that is genetically modified with a nucleic acid comprising nucleotide sequences encoding MK, PMK, MPD, and IDI. The pta gene will in some embodiments be deleted from a host cell (e.g., *E. coli*) that is genetically modified with a nucleic acid comprising nucleotide sequences encoding MK, PMK, MPD, and IPP. The pta gene will in some embodiments be deleted from a host cell (e.g., *E. coli*) that is genetically modified with a nucleic acid comprising nucleotide sequences encoding MK, PMK, MPD, IPP, and a prenyl transferase.

In some embodiments, a subject genetically modified host cell is one that is genetically modified to include one or more nucleic acids comprising a nucleotide sequence(s) that encode MEV biosynthetic pathway gene product(s); and that is further genetically modified such that an endogenous DXP biosynthetic pathway gene is functionally disabled. In other embodiments, a subject genetically modified host cell is one that is genetically modified to include one or more nucleic acids comprising a nucleotide sequence(s) that encode DXP biosynthetic pathway gene product(s); and that is further genetically modified such that an endogenous MEV biosynthetic pathway gene is functionally disabled.

In some embodiments, where subject genetically modified host cell is a prokaryotic host cell that is genetically modified with nucleic acid(s) comprising nucleotide sequences encoding one or more MEV pathway gene products, the host cell will be further genetically modified such that one or more endogenous DXP pathway genes is functionally disabled. DXP pathway genes that can be functionally disabled include one or more of the genes encoding any of the following DXP gene products: 1-deoxy-D-xylulose-5-phosphate synthase, 1-deoxy-D-xylulose-5-phosphate reductoisomerase, 4-diphosphocytidyl-2-C-methyl-D-erythritol synthase, 4-diphosphocytidyl-2-C-methyl-D-erythritol kinase, 2C-methyl-D-erythritol 2,4-cyclodiphosphate synthase, and 1-hydroxy-2-methyl-2-(E)-butenyl 4-diphosphate synthase.

An endogenous DXP pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

In other embodiments, where subject genetically modified host cell is a prokaryotic host cell that is genetically modified with nucleic acid(s) comprising nucleotide sequences encoding one or more DXP pathway gene products, the host cell will be further genetically modified such that one or more endogenous MEV pathway genes is functionally disabled. Endogenous MEV pathway genes that can be functionally disabled include one or more of the genes encoding any of the following MEV gene products: HMGS, HMGR, MK, PMK, MPD, and IDI. An endogenous MEV pathway gene can be functionally disabled in any of a variety of ways, including insertion of a mobile genetic element (e.g., a transposon, etc.); deletion of all or part of the gene, such that the gene product is not made, or is truncated and is enzymatically inactive; mutation of the gene such that the gene product is not made, or is truncated and is enzymatically non-functional; deletion or mutation of one or more control elements that control expression of the gene such that the gene product is not made; and the like.

Compositions Comprising a Subject Genetically Modified Host Cell

The present invention further provides compositions comprising a subject genetically modified host cell. A subject composition comprises a subject genetically modified host cell, and will in some embodiments comprise one or more further components, which components are selected based in part on the intended use of the genetically modified host cell. Suitable components include, but are not limited to, salts; buffers; stabilizers; protease-inhibiting agents; nuclease-inhibiting agents; cell membrane- and/or cell wall-preserving compounds, e.g., glycerol, dimethylsulfoxide, etc.; nutritional media appropriate to the cell; and the like. In some embodiments, the cells are lyophilized.

Transgenic Plants

In some embodiments, a subject nucleic acid or a subject expression vector (e.g., a subject isoprenoid-modifying enzyme nucleic acid or a subject expression vector comprising an isoprenoid-modifying enzyme nucleic acid) is used as a transgene to generate a transgenic plant that produces the encoded isoprenoid-modifying enzyme. Thus, the present invention further provides a transgenic plant, which plant comprises a transgene comprising a subject nucleic acid comprising a nucleotide sequence encoding an enzyme that exhibits terpene hydroxylase and/or terpene oxidase activity, as described above. In some embodiments, the genome of the transgenic plant comprises a subject nucleic acid. In some embodiments, the transgenic plant is homozygous for the genetic modification. In some embodiments, the transgenic plant is heterozygous for the genetic modification.

In some embodiments, a subject transgenic plant produces a transgene-encoded polypeptide that exhibits terpene hydroxylase and/or oxidase activity in an amount that is at least about 50%, at least about 2-fold, at least about 5-fold, at least about 10-fold, at least about 25-fold, at least about 50-fold, or at least about 100-fold, or higher, than the amount of the polypeptide produced by a control plant, e.g., a non-transgenic plant (a plant that does not include the transgene encoding the polypeptide) of the same species.

In some embodiments, a subject transgenic plant is a transgenic version of a control, non-transgenic plant that normally produces an isoprenoid compound that is generated by, or is a downstream product of, a transgene-encoded polypeptide that exhibits terpene hydroxylase and/or oxidase activity; where the transgenic plant produces the isoprenoid compound in an amount that is at least about 50%, at least about 2-fold, at least about 5-fold, at least about 10-fold, at least about 25-fold, at least about 50-fold, or at least about 100-fold, or higher, than the amount of the isoprenoid compound produced by the control plant, e.g., a non-transgenic plant (a plant that does not include the transgene encoding the polypeptide) of the same species.

Methods of introducing exogenous nucleic acids into plant cells are well known in the art. Such plant cells are considered "transformed," as defined above. Suitable methods include viral infection (such as double stranded DNA viruses), transfection, conjugation, protoplast fusion, electroporation, particle gun technology, calcium phosphate precipitation, direct microinjection, silicon carbide whiskers technology, *Agrobacterium*-mediated transformation and the like. The choice of method is generally dependent on the type of cell being transformed and the circumstances under which the transformation is taking place (i.e. in vitro, ex vivo, or in vivo).

Transformation methods based upon the soil bacterium *Agrobacterium tumefaciens* are particularly useful for introducing an exogenous nucleic acid molecule into a vascular plant. The wild type form of *Agrobacterium* contains a Ti (tumor-inducing) plasmid that directs production of tumorigenic crown gall growth on host plants. Transfer of the tumor-inducing T-DNA region of the Ti plasmid to a plant genome requires the Ti plasmid-encoded virulence genes as well as T-DNA borders, which are a set of direct DNA repeats that delineate the region to be transferred. An *Agrobacterium*-based vector is a modified form of a Ti plasmid, in which the tumor inducing functions are replaced by the nucleic acid sequence of interest to be introduced into the plant host.

*Agrobacterium*-mediated transformation generally employs cointegrate vectors or, preferably, binary vector systems, in which the components of the Ti plasmid are divided between a helper vector, which resides permanently in the *Agrobacterium* host and carries the virulence genes, and a shuttle vector, which contains the gene of interest bounded by T-DNA sequences. A variety of binary vectors are well known in the art and are commercially available, for example, from Clontech (Palo Alto, Calif.). Methods of coculturing *Agrobacterium* with cultured plant cells or wounded tissue such as leaf tissue, root explants, hypocotyledons, stem pieces or tubers, for example, also are well known in the art. See., e.g., Glick and Thompson, (eds.), *Methods in Plant Molecular Biology and Biotechnology*, Boca Raton, Fla.: CRC Press (1993).

*Agrobacterium*-mediated transformation is useful for producing a variety of transgenic vascular plants (Wang et al., supra, 1995) including at least one species of *Eucalyptus* and forage legumes such as alfalfa (lucerne); birdsfoot trefoil, white clover, *Stylosanthes, Lotononis bainessii* and sainfoin.

Microprojectile-mediated transformation also can be used to produce a subject transgenic plant. This method, first described by Klein et al. (*Nature* 327:70-73 (1987)), relies on microprojectiles such as gold or tungsten that are coated with the desired nucleic acid molecule by precipitation with calcium chloride, spermidine or polyethylene glycol. The microprojectile particles are accelerated at high speed into an angiosperm tissue using a device such as the BIOLISTIC PD-1000 (Biorad; Hercules Calif.).

A subject nucleic acid may be introduced into a plant in a manner such that the nucleic acid is able to enter a plant cell(s), e.g., via an in vivo or ex vivo protocol. By "in vivo," it is meant in the nucleic acid is administered to a living body of a plant e.g. infiltration. By "ex vivo" it is meant that cells or explants are modified outside of the plant, and then such cells or organs are regenerated to a plant. A number of vectors suitable for stable transformation of plant cells or for the establishment of transgenic plants have been described, including those described in Weissbach and Weissbach, (1989) Methods for Plant Molecular Biology Academic Press, and Gelvin et al., (1990) Plant Molecular Biology Manual, Kluwer Academic Publishers. Specific examples include those derived from a Ti plasmid of *Agrobacterium tumefaciens*, as well as those disclosed by Herrera-Estrella et al. (1983) Nature 303: 209, Bevan (1984) Nucl Acid Res. 12: 8711-8721, Klee (1985) Bio/Technolo 3: 637-642. Alternatively, non-Ti vectors can be used to transfer the DNA into plants and cells by using free DNA delivery techniques. By using these methods transgenic plants such as wheat, rice (Christou (1991) Bio/Technology 9:957-962) and corn (Gordon-Kamm (1990) Plant Cell 2: 603-618) can be produced. An immature embryo can also be a good target tissue for monocots for direct DNA delivery techniques by using the particle gun (Weeks et al. (1993) Plant Physiol 102: 1077-1084; Vasil (1993) Bio/Technolo 10: 667-674; Wan and Lemeaux (1994) Plant Physiol 104: 37-48 and for *Agrobacterium*-mediated DNA transfer (Ishida et al. (1996) Nature Biotech 14: 745-750). Exemplary methods for introduction of DNA into chloroplasts are biolistic bombardment, polyethylene glycol transformation of protoplasts, and microinjection (Danieli et al Nat. Biotechnol 16:345-348, 1998; Staub et al Nat. Biotechnol 18: 333-338, 2000; O'Neill et al Plant J. 3:729-738, 1993; Knoblauch et al Nat. Biotechnol 17: 906-909; U.S. Pat. Nos. 5,451,513, 5,545,817, 5,545,818, and 5,576,198; in Intl. Application No. WO 95/16783; and in Boynton et al., Methods in Enzymology 217: 510-536 (1993), Svab et al., Proc. Natl. Acad. Sci. USA 90: 913-917 (1993), and McBride et al., Proc. Natl. Acad. Sci. USA 91: 7301-7305 (1994)). Any vector suitable for the methods of biolistic bombardment, polyethylene glycol transformation of protoplasts and microinjection will be suitable as a targeting vector for chloroplast transformation. Any double stranded DNA vector may be used as a transformation vector, especially when the method of introduction does not utilize *Agrobacterium*.

Plants which can be genetically modified include grains, forage crops, fruits, vegetables, oil seed crops, palms, forestry, and vines. Specific examples of plants which can be modified follow: maize, banana, peanut, field peas, sunflower, tomato, canola, tobacco, wheat, barley, oats, potato, soybeans, cotton, carnations, sorghum, lupin and rice. Other examples include *Artemisia annua*, or other plants known to produce isoprenoid compounds of interest.

Also provided by the subject invention are transformed plant cells, tissues, plants and products that contain the transformed plant cells. A feature of the subject transformed cells, and tissues and products that include the same is the presence of a subject nucleic acid integrated into the genome, and production by plant cells of a polypeptide that exhibits terpene hydroxylase and/or terpene oxidase activity, e.g., a sesquiterpene oxidase. Recombinant plant cells of the present invention are useful as populations of recombinant cells, or as a tissue, seed, whole plant, stem, fruit, leaf, root, flower, stem, tuber, grain, animal feed, a field of plants, and the like.

Also provided by the subject invention is reproductive material of a subject transgenic plant, where reproductive material includes seeds, progeny plants and clonal material.

Methods of Producing Isoprenoid Compounds

The present invention provides a method of producing an isoprenoid compound. In some embodiments, the methods generally involve culturing a genetically modified host cell in a suitable medium, wherein said host cell is genetically modified with a subject nucleic acid comprising a nucleotide sequence encoding an isoprenoid-modifying enzyme. In other embodiments, the methods generally involve maintaining a subject transgenic plant under conditions that favor production of the encoded isoprenoid-modifying enzyme. Production of the isoprenoid-modifying enzyme results in production of the isoprenoid compound. For example, in some embodiments, the methods generally involve culturing a genetically modified host cell in a suitable medium, wherein said host cell is genetically modified with a subject nucleic acid comprising a nucleotide sequence encoding a terpene oxidase. Production of the terpene oxidase results in production of the isoprenoid compound. Typically, the method is carried out in vitro, although in vivo production of an isoprenoid compound is also contemplated. In some of these embodiments, the host cell is a eukaryotic cell, e.g., a yeast cell. In other embodiments, the host cell is a prokaryotic cell. In some of these embodiments, the host cell is a plant cell. In some embodiments, the method is carried out in a subject transgenic plant.

Figure 13:
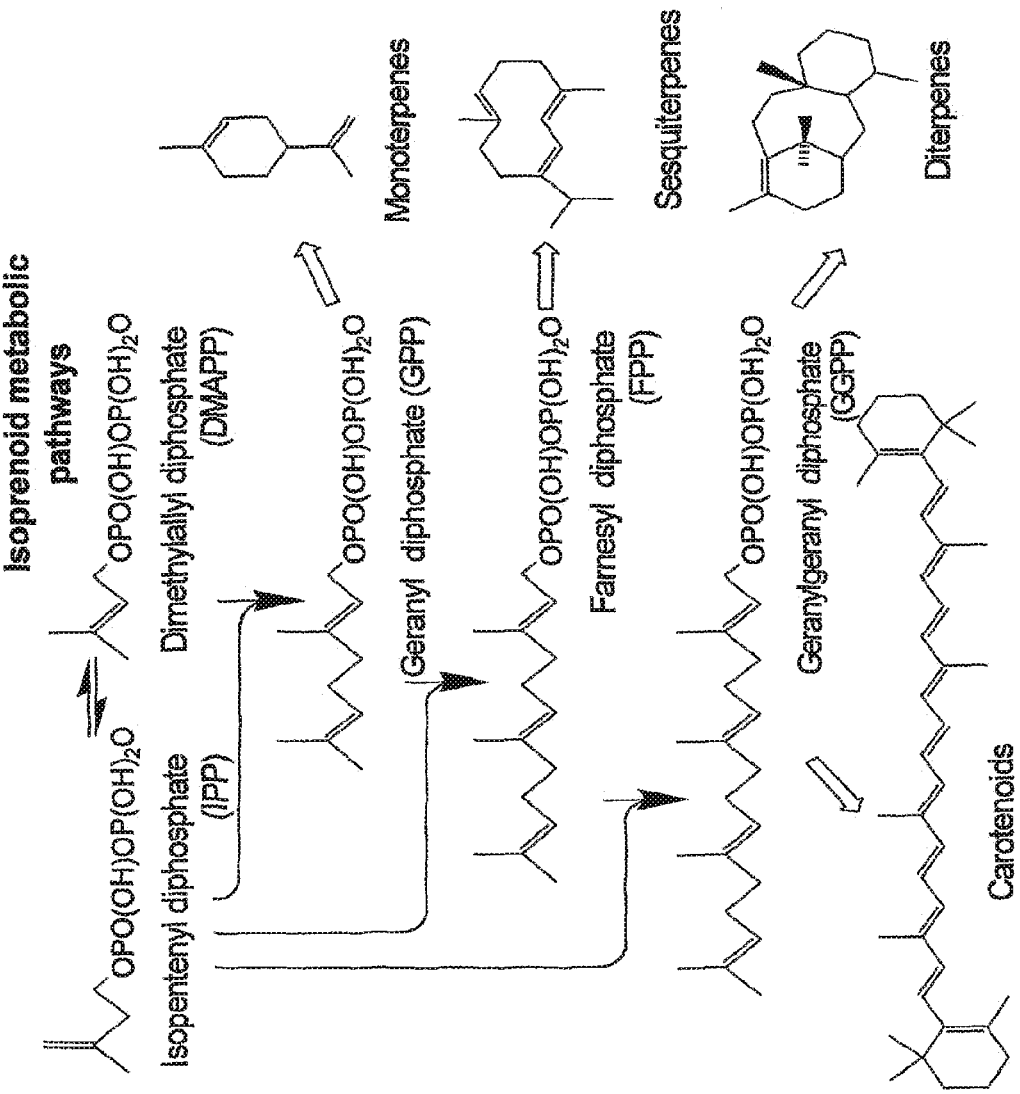
FIG. 13 is a schematic representation of isoprenoid metabolic pathways that result in the production of the isoprenoid biosynthetic pathway intermediates polyprenyl diphosphates geranyl diphosphate (GPP), farnesyl diphosphate (FPP), and geranylgeranyl diphosphate (GGPPP), from isopentenyl diphosphate (IPP) and dimethylallyl diphosphate (DMAPP).
Figure 14:
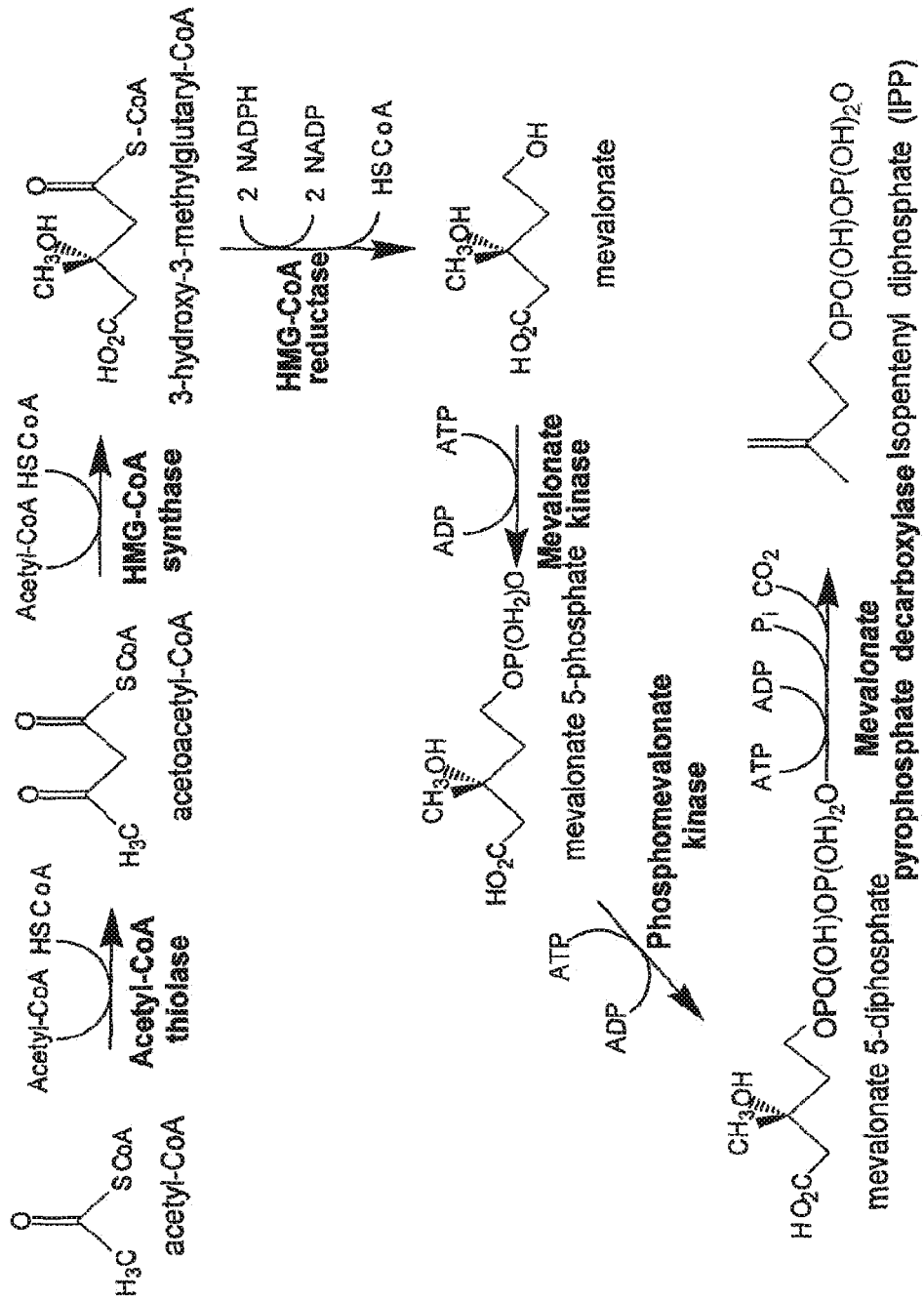
FIG. 14 is a schematic representation of the mevalonate (MEV) pathway for the production of IPP.

Cells typically use one of two pathways to generate isoprenoids or isoprenoid precursors (e.g., IPP, polyprenyl diphosphates, etc.). FIGS. 13-15 serve to illustrate the pathways used by cells to generate isoprenoid compounds, or precursors such as polyprenyl diphosphates.

FIG. 13 depicts isoprenoid pathways involving modification of isopentenyl diphosphate (IPP) and/or its isomer dimethylallyl diphosphate (DMAPP) by prenyl transferases to generate the polyprenyl diphosphates geranyl diphosphate (GPP), farnesyl diphosphate (FPP), and geranylgeranyl diphosphate (GGPP). GPP and FPP are further modified by terpene synthases to generate monoterpenes and sesquiterpenes, respectively; and GGPP is further modified by terpene synthases to generate diterpenes and carotenoids. IPP and DMAPP are generated by one of two pathways: the mevalonate (MEV) pathway and the 1-deoxy-D-xylulose-5-phosphate (DXP) pathway.

FIG. 14 depicts schematically the MEV pathway, where acetyl CoA is converted via a series of reactions to IPP.

FIG. 15 depicts schematically the DXP pathway, in which pyruvate and D-glyceraldehyde-3-phosphate are converted via a series of reactions to IPP and DMAPP. Eukaryotic cells other than plant cells use the MEV isoprenoid pathway exclusively to convert acetyl-coenzyme A (acetyl-CoA) to IPP, which is subsequently isomerized to DMAPP. Plants use both the MEV and the mevalonate-independent, or DXP pathways for isoprenoid synthesis. Prokaryotes, with some exceptions, use the DXP pathway to produce IPP and DMAPP separately through a branch point.

In some embodiments, a host cell is genetically modified with a subject nucleic acid comprising a nucleotide sequence encoding a sesquiterpene oxidase, and the host cell is cultured in medium that includes the sesquiterpene. The sesquiterpene enters the cell, where it is modified by the sesquiterpene oxidase. In many embodiments, the sesquiterpene is selected from amorphadiene, alloisolongifolene, (−)-α-trans-bergamotene, (−)-β-elemene, (+)-germacrene A, germacrene B, (+)-γ-gurjunene, (+)-ledene, neointermedeol, (+)-β-selinene, and (+)-valencene. In some embodiments, the sesquiterpene oxidase is an amorphadiene oxidase, and the host cell is cultured in a medium that includes amorpha-4,11-diene oxidase.

In other embodiments, the host cell is further genetically modified with a nucleic acid comprising a nucleotide sequence encoding a terpene synthase. Thus, e.g., the host cell is genetically modified with one or more nucleic acids comprising nucleotide sequences encoding a terpene synthase and an isoprenoid-modifying enzyme (e.g., a sesquiterpene oxidase). Culturing such a host cell in a suitable culture medium provides for production of the terpene synthase and the isoprenoid-modifying enzyme (e.g., a sesquiterpene oxidase). For example, the terpene synthase modifies a farnesyl pyrophosphate to generate a sesquiterpene substrate for said sesquiterpene oxidase.

Depending on the culture medium in which the host cell is cultured, and depending on whether the host cell synthesizes IPP via a DXP pathway or via a mevalonate pathway, the host cell will in some embodiments include further genetic modifications. For example, in some embodiments, the host cell is one that does not have an endogenous mevalonate pathway, e.g., the host cell is one that does not normally synthesize IPP or mevalonate via a mevalonate pathway. For example, in some embodiments, the host cell is one that does not normally synthesize IPP via a mevalonate pathway, and the host cell is genetically modified with one or more nucleic acids comprising nucleotide sequences encoding two or more enzymes in the mevalonate pathway, an IPP isomerase, a prenyltransferase, a terpene synthase, and an isoprenoid-modifying enzyme (e.g., an isoprenoid-modifying enzyme encoded by a subject nucleic acid). Culturing such a host cell provides for production of the mevalonate pathway enzymes, the IPP isomerase, the prenyltransferase, the terpene synthase, and the isoprenoid-modifying enzyme (e.g., a sesquiterpene oxidase). Production of the mevalonate pathway enzymes, the IPP isomerase, the prenyltransferase, the terpene synthase, and the isoprenoid-modifying enzyme (e.g., a sesquiterpene oxidase) results in production of an isoprenoid compound. In many embodiments, the prenyltransferase is an FPP synthase, which generates a sesquiterpene substrate for a sesquiterpene oxidase encoded by a subject nucleic acid; and production of the sesquiterpene oxidase results in oxidation of the sesquiterpene substrate in the host cell. Any nucleic acids encoding the mevalonate pathway enzymes, the IPP isomerase, the prenyltransferase, and the terpene synthase are suitable for use. For example, suitable nucleic acids are described in, e.g., Martin et al. (2003) supra.

In some of the above-described embodiments, where the host cell is genetically modified with one or more nucleic acids comprising nucleotide sequences encoding two or more mevalonate pathway enzymes, the two or more mevalonate pathway enzymes include MK, PMK, and MPD, and the host cell is cultured in medium that includes mevalonate. In other embodiments, the two or more mevalonate pathway enzymes include acetoacetyl CoA thiolase, HMGS, HMGR, MK, PMK, and MPD.

In some embodiments, the host cell is one that does not normally synthesize IPP via mevalonate pathway, the host cell is genetically modified as described above, and the host cell further comprises a functionally disabled DXP pathway.

In some embodiments, the host cell is genetically modified with a nucleic acid comprising a nucleotide sequence encoding a cytochrome P450 reductase (CPR). A wide variety of nucleotide sequences of CPR are known, and any known CPR-encoding nucleic acid can be used, as long as the encoded CPR exhibits activity in transferring electrons from NADPH. In some embodiments, the CPR-encoding nucleic acid encodes a CPR that transfers electrons from NADPH to an isoprenoid-modifying enzyme, e.g., a sesquiterpene oxidase, encoded by a subject isoprenoid-modifying enzyme-encoding nucleic acid. In some embodiments, the CPR-encoding nucleic acid is a subject CPR nucleic acid.

A subject method is useful for production of a variety of isoprenoid compounds, including, but not limited to, artemisinic acid (e.g., where the sesquiterpene substrate is amorpha-4,11-diene), alloisolongifolene alcohol (e.g., where the substrate is alloisolongifolene), (E)-trans-bergamota-2,12-dien-14-ol (e.g., where the substrate is (−)-α-trans-bergamotene), (−)-elema-1,3,11(13)-trien-12-ol (e.g., where the substrate is (−)-β-elemene), germacra-1(10),4,11(13)-trien-12-ol (e.g., where the substrate is (+)-germacrene A), germacrene B alcohol (e.g., where the substrate is germacrene B), 5,11(13)-guaiadiene-12-ol (e.g., where the substrate is (+)-γ-gurjunene), ledene alcohol (e.g., where the substrate is (+)-ledene), 4β-H-eudesm-11(13)-ene-4,12-diol (e.g., where the substrate is neointermedeol), (+)-β-costol (e.g., where the substrate is (+)-β-selinene, and the like; and further derivatives of any of the foregoing.

In some embodiments, a subject genetically modified host cell is cultured in a suitable medium (e.g., Luria-Bertoni broth, optionally supplemented with one or more additional agents, such as an inducer (e.g., where the isoprenoid-modifying enzyme-encoding nucleotide sequence is under the control of an inducible promoter), etc.); and the culture medium is overlaid with an organic solvent, e.g. dodecane, forming an organic layer. The isoprenoid compound produced by the genetically modified host cell partitions into the organic layer, from which it can be purified. In some embodiments, where the isoprenoid-modifying enzyme-encoding nucleotide sequence is operably linked to an inducible promoter, an inducer is added to the culture medium; and, after a suitable time, the isoprenoid compound is isolated from the organic layer overlaid on the culture medium.

In some embodiments, the isoprenoid compound will be separated from other products which may be present in the organic layer. Separation of the isoprenoid compound from other products that may be present in the organic layer is readily achieved using, e.g., standard chromatographic techniques.

In some embodiments, an isoprenoid compound synthesized by a subject method is further chemically modified in a cell-free reaction. For example, in some embodiments, artemisinic acid is isolated from culture medium and/or a cell lysate, and the artemisinic acid is further chemically modified in a cell-free reaction to generate artemisinin.

In some embodiments, the isoprenoid compound is pure, e.g., at least about 40% pure, at least about 50% pure, at least about 60% pure, at least about 70% pure, at least about 80% pure, at least about 90% pure, at least about 95% pure, at least about 98%, or more than 98% pure, where "pure" in the context of an isoprenoid compound refers to an isoprenoid compound that is free from other isoprenoid compounds, macromolecules, contaminants, etc.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

Example 1

Cloning and Sequencing of Isoprenoid Modifying Enzymes

Most enzymes known to hydroxylate a terpene are cytochrome P450s. All available amino acid sequences of terpene hydroxylases were aligned with the amino acid sequences of cytochrome P450s from sunflower and lettuce. These two plant species belong to the Asteraceae family, to which *Artemisia annua* also belongs. Isoprenoid-modifying enzymes, e.g., the CYP71D family, clustered together, suggesting a common ancestor. Degenerate polymerase chain reaction (PCR) primers were designed, which primers amplify genes of the Asteraceae CYP71D family.

Cloning of CYP71AV1 (Also Referred to as CYP71D-A4, or AMO) and CPR cDNA.

A cDNA pool was prepared by Super SMART PCR cDNA synthesis kit (BD Bioscience) using 50 ng of total RNA purified from *A. annua* trichome-enriched cells. Degenerate P450 primers were designed from a conserved amino acid motif of lettuce and sunflower CYP71 subfamily; primer 1 from [Y/Q]G[E/D][H/Y]WR (forward) and primer 2 from FIPERF (reverse) (Table I provides sequence information for the primers).

TABLE I

Primers used for construction of plasmids

| Primer number | Sequence (5' to 3') |
|---|---|
| 1 | TCCGACCA(C/T)ANGGNGAN(C/T)A(C/T)TGGAG; SEQ ID NO :14 |
| 2 | TCCGACCAAANC(G/T)(C/T)TCNGG(A/G/T)AT(A/G)AA; SEQ ID NO :15 |
| 3 | CCAGCACA(A/G)TA(C/T)GA(A/G)CA(C/T)TT(C/T)AA(C/T)AA(A/G)AT; SEQ ID NO :16 |
| 4 | CCAGCAGCCATNCC(C/T)TTNGC(A/G)TCNCC(A/G)CA; SEQ ID NO :17 |
| 5 | ACGTCTAGAATGAAGAGTATACTAAAAGCAATG; SEQ ID NO :18 |
| 6 | ACGTCTAGAGCGAAACTTGGAACGAGTAACAACT; SEQ ID NO :19 |
| 7 | ATGGATCCTATGCAATCAACAACTTCCGTTAAGTTAT; SEQ ID NO :20 |

TABLE I-continued

Primers used for construction of plasmids

| Primer number | Sequence (5' to 3') |
|---|---|
| 8 | TATGTCGACCCATACATCACGGAGATATCTTCCT; SEQ ID NO :21 |
| 9 | GGACTAGTAAAACAATGGCCCTGACCGAAGAG; SEQ ID NO :22 |
| 10 | CCAAGCTTTCAGATGGACATCGGGTAAAC; SEQ ID NO :23 |
| 11 | CTGCCGCGGGGCCGCAAATTAAAGCCTTC; SEQ ID NO :24 |
| 12 | CTGCCGCGGTAGTACGGATTAGAAGCCGC; SEQ ID NO :25 |
| 13 | CGGGATCCAAAACAATGGCTGCAGACCAATTGGTG; SEQ ID NO :26 |
| 14 | GCGTCGACTTAGGATTTAATGCAGGTGACG; SEQ ID NO :27 |
| 15 | CGGGATCCAAAACAATGAGCGAAGTCGGTATACAG; SEQ ID NO :28 |
| 16 | GCGTCGACTCATAACGAAAAATCAGAGAAATTTG; SEQ ID NO :29 |
| 17 | GGACTAGTAAAACAATGGCTTCAGAAAAAGAAATTAG; SEQ ID NO :30 |
| 18 | TCCCCCGGGCTATTTGCTTCTCTTGTAAAC; SEQ ID NO :31 |

Polymerase chain reaction (PCR) using these primers and *A. annua* cDNAs yielded a 1-kb DNA fragment. The PCR-program used was 7 cycles with 48° C. annealing temperature and additional 27 cycles with 55° C. annealing temperature. The deduced amino acids from the amplified gene fragment showed 85% and 88% amino acid identity to the sunflower (QH_CA_Contig1442) and lettuce (QG_CA_Contig7108) contigs, respectively. The Compositae EST-database can be found at cgpdb.ucdavis.edu. *A. annua* CPR fragment was isolated using a forward primer (primer 3), and a reverse primer (primer 4), designed from the conserved QYEHFNKI (SEQ ID NO:32) and CGDAKGMA (SEQ ID NO:33) motifs, respectively. The PCR-program used was 30 cycles with 50° C. annealing temperature. Both 5'- and 3'-end sequences for CYP71AV1 ("CYP71D-A4") and CPR were determined using an RLM-RACE kit (Ambion) followed by full-length cDNA recovery from *A. annua* leaf cDNAs. The open reading frames of CYP71AV1 and CPR were amplified by PCR and ligated into the SpeI and BamHI/SalI sites of pESC-URA (Stratagene) in FLAG and cMyc tagging, respectively. For PCR-amplification of CYP71AV1, primers 5 and 6 were used; for PCR-amplification of CPR, primers 7 and 8 were used. The PCR-program used was 35 cycles with 55° C. annealing temperature. All clones were sequenced to confirm sequences.

Plant Extract Analysis.

*A. annua* leaf (100 to 200 mg fresh weight) was vigorously shaken in 1 mL hexane spiked with 5.8 µM octadecane as an internal standard for 2 hours. The hexanolic extracts were concentrated to 200 and 1 µL sample was used for the GC-MS analysis using a DB-XLB column (0.25 mm i.d.×0.25 µm×30 m, J & W Scientific) to determine artemisinin content from 14 plant samples as described. Woerdenbag et al. (1991) *Phy-* tochem. Anal., 2, 215-219. GC oven program used was 100° C. to 250° C. in 5° C. min$^{-1}$ increment. The plant hexanolic extracts were derivatized by TMS-diazomethane to determine artemisinic acid content by the GC-FID equipped with DB5 column (n=8). The GC oven program used was 80° C. (hold 2 min), 20° C. min$^{-1}$ ramp to 140° C., product separation by 5° C. min$^{-1}$ increment up to 220° C. Authentic artemisinin standards were purchased from Sigma-Aldrich (St. Louis, Mo.).

Synthesis of Artemisinic Alcohol.

Artemisinic acid (100.0 mg, 0.43 mmol) was dissolved in THF (10.0 mL) and LiAlH$_4$ (17.0 mg, 0.45 mmol) was added. The heterogeneous mixture was held at reflux (70° C.) for 15 h. After cooling, the reaction was quenched with water (3.0 mL) and 15% aqueous NaOH (3.0 mL), stirred for 10 min and filtered through celite. The organic phase was separated, dried over MgSO$_4$, and concentrated using a rotary evaporator. The product was purified by column chromatography (2:1 hexanes/EtOAc) to give 61.0 mg (65% yield) of the alcohol as a colorless oil. A minor amount of artemisinic acid contaminant was further removed by column chromatography over neutral alumina (Brockman activity 1). Characterization data was consistent with literature values.

Synthesis of Artemisinic Aldehyde.

Artemisinic alcohol was oxidized to artemisinic aldehyde following a procedure reported in the literature. Sharpless et al. *Tetrahedron Letters* 17, 2503-2506 (1976). In a flame-dried 10-mL flask containing RuCl$_2$(PPh$_3$)$_3$ (17.0 mg, 0.018 mmol) and N-methyl morpholine N-oxide (60.0 mg, 0.51 mmol) under an atmosphere of argon was added acetone (4.0 mL). To the solution was added artemisinic alcohol (55.0 mg, 0.25 mmol) dissolved in acetone (1.0 mL) via syringe. The mixture was stirred at 23° C. for 2 h and concentrated in vacuo. The crude product was purified by column chromatography (4:1 hexanes/EtOAc) to give 32.0 mg (59% yield) of artemisinic aldehyde as a colorless oil. Characterization data was consistent with literature report.

EPY Strain Generation and Characterization

Chemicals.

Dodecane and caryophyllene were purchased from Sigma-Aldrich (St. Louis, Mo.). 5-fluoroortic acid (5-FOA) was purchased from Zymo Research (Orange, Calif.). Complete Supplement Mixtures for formulation of Synthetic Defined (SD) media were purchased from Qbiogene (Irvine, Calif.). All other media components were purchased from either Sigma-Aldrich or Becton, Dickinson (Franklin Lakes, N.J.).

Strains and Media.

*Escherichia coli* strains DH10B and DH5α were used for bacterial transformation and plasmid amplification in the construction of the expression plasmids used in this study. The strains were cultivated at 37° C. in Luria-Bertani medium with 100 mg L$^{-1}$ ampicillin with the exception of pδ-UB-based plasmids which were cultivated with 50 mg L$^{-1}$ ampicillin using DH5α.

*Saccharomyces cerevisiae* strain BY4742 (Brachmann et al. *Yeast* 14, 115-132 (1998)), a derivative of S288C, was used as the parent strain for all yeast strains. This strain was grown in rich YPD medium. Burke et al. *Methods in yeast genetics: a Cold Spring Harbor laboratory course manual* (Cold Spring Harbor Laboratory Press, Plainview, N.Y., 2000). Engineered yeast strains were grown in SD medium (Burke et al., supra) with leucine, uracil, histidine, and/or methionine dropped out where appropriate. For induction of genes expressed from the GAL1 promoter, *S. cerevisiae* strains were grown in 2% galactose as the sole carbon source.

Plasmid Construction.

To create plasmid pRS425ADS for expression of ADS with the GAL1 promoter, ADS was PCR amplified from pADS (Martin et al. *Nat. Biotechnol.* 21, 796-802 (2003)) using primer pair 9 and 10. (Table I). Using these primers, the nucleotide sequence 5'-AAAACA-3' was cloned immediately upstream of the start codon of ADS. This consensus sequence was used for efficient translation of ADS and the other galactose-inducible genes used in this study. The amplified product was cleaved with SpeI and HindIII and cloned into SpeI and HindIII digested pRS425GAL1 (Mumberg et al. *Nucleic Acids Research* 22, 5767-5768 (1994)).

For integration of an expression cassette for tHMGR, plasmid pδ-HMGR was constructed. First SacII restriction sites were introduced into pRS426GAL1 (Mumberg et al., supra) at the 5' end of the GAL1 promoter and 3' end of the CYC1 terminator. To achieve this, the promoter-multiple cloning site-terminator cassette of pRS426GAL1 was PCR amplified using primer pair 11 and 12. The amplified product was cloned directly into PvuII-digested pRS426GAL1 to construct vector pRS426-SacII. The catalytic domain of HMG1 was PCR amplified from plasmid pRH127-3 (Donald et al. *Appl. Environ. Microbiol.* 63, 3341-3344 (1997)) with primer pair 13 and 14. The amplified product was cleaved with BamHI and SalI and cloned into BamHI and XhoI digested pRS426-SacII. pRS-HMGR was cleaved with SacII and the expression cassette fragment was gel extracted and cloned into SacII digested pδ-UB (Lee et al. *Biotechnol. Prog.* 13, 368-373 (1997)).

The upc2-1 allele of UPC2 was PCR amplified from plasmid pBD33 using primer pair 15 and 16. The amplified product was cleaved with BamHI and SalI and cloned into BamHI and XhoI digested pRS426-SacII to create plasmid pRS-UPC2. For the integration of upc2-1, pδ-UPC2 was created in an identical manner by digesting pRS-UPC2 with SacII and moving the appropriate fragment to pδ-UB.

To replace the ERG9 promoter with the MET3 promoter, plasmid pRS-ERG9 was constructed. Plasmid pRH973 (Gardner et al. *J. Biol. Chem.* 274, 31671-31678 (1999)) contained a truncated 5' segment of ERG9 placed behind the MET3 promoter. pRH973 was cleaved with ApaI and ClaI and cloned into ApaI and ClaI digested pRS403 which has a HIS3 selection marker (Sikorski et al. *Genetics* 122, 19-27 (1989)).

For expression of ERG20, plasmid pδ-ERG20 was constructed. Plasmid pRS-SacII was first digested with SalI and XhoI which created compatible cohesive ends. The plasmid was then self-ligated, eliminating SalI and XhoI sites to create plasmid pRS-SacII-DX. ERG20 was PCR amplified from the genomic DNA of BY4742 using primer pair 17 and 18. The amplified product was cleaved with SpeI and SmaI and cloned into SpeI and SmaI digested pRS-SacII-DX. pRS-ERG20 was then cleaved with SacII and the expression cassette fragment was gel extracted and cloned into SacII digested pδ-UB.

Yeast Transformation and Strain Construction.

*S. cerevisiae* strain BY4742 (Brachmann et al., supra), a derivative of S288C was used as the parent strain for all *S. cerevisiae* strains. Transformation of all strains of *S. cerevisiae* was performed by the standard lithium acetate method. Gietz, R. D. & Woods, R. A. in *Guide to Yeast Genetics and Molecular and Cell Biology, Part B*, 87-96 (Academic Press Inc, San Diego, 2002). Three to ten colonies from each transformation were screened for the selection of the highest amorphadiene producing transformant. Strain EPY201 was constructed by the transformation of strain BY4742 with plasmid pRS425ADS and selection on SD-LEU plates. Plasmid pδ-HMGR was digested with XhoI before transformation of the DNA into strain EPY201. After initial selection on SD-LEU-URA plates, transformants were cultured and plated on SD-LEU plates containing 1 g L$^{-1}$ 5-FOA as a selection for the loss of the URA3 marker. The resulting uracil auxotroph, EPY208 was then transformed with XhoI-digested pδ-UPC2 plasmid DNA. After initial selection on SD-LEU-URA plates, transformants were cultured and plated on SD-LEU plates including 1 g L$^{-1}$ 5-FOA for the construction of EPY210. Plasmid pRS-ERG9 was cleaved with HindIII for the integration of the P$_{MET3}$-ERG9 fusion at the ERG9 loci of EPY208 and EPY210 for the construction of EPY213 and EPY225, respectively. These strains were selected for on SD-LEU-HIS-MET plates. EPY213 was then transformed with XhoI digested pδ-HMGR plasmid DNA. After initial selection on SD-LEU-URA-HIS-MET plates, transformants were cultured and plated on SD-LEU-HIS-MET plates containing 1 g L$^{-1}$ 5-FOA for the construction of EPY219. EPY219 was transformed with XhoI digested pδ-ERG20 plasmid DNA. After initial selection on SD-LEU-URA-HIS-MET plates, transformants were cultured and plated on SD-LEU-HIS-MET plates including 1 g L$^{-1}$ 5-FOA for the construction of EPY224.

Integration of pRS-ERG9 was verified by PCR analysis using two sets of primers. Each set contained one oligo to bind to the inserted DNA and one to bind to the genomic DNA surrounding the insertion. All other integrations were verified for full length insertion using a primer binding to the 5'-end of the GAL1 promoter and 3'-end of the fused gene.

Yeast Cultivation.

All optical densities at 600 nm (OD$_{600}$) measurements were taken using a Beckman DU-640 spectrophotometer. To measure amorphadiene production, culture tubes containing 5 mL of SD (2% galactose) medium (with appropriate amino acid omissions as described above) were inoculated with the strains of interest. These innocula were grown at 30° C. to OD$_{600}$ between 1 and 2. Unbaffled culture flasks (250 mL) containing 50 mL SD medium were inoculated to an OD$_{600}$ 0.05 with these seed cultures. Amorphadiene production was measured after 6 days of growth. 1 mM methionine was present in each culture for repression of the P$_{MET3}$-ERG9 fusion at the ERG9 loci. All flasks also contained 5 mL dodecane. This dodecane layer was sampled and diluted in ethyl acetate for determination of amorphadiene production by GC-MS.

Results

Artemisinin is produced in the glandular trichomes, specialized cells of plant. Glandular trichome cells were isolated from *A. annua*; and RNA was extracted from the cells. Using the degenerate primers, a partial cDNA of a novel gene that was named CYP71D-A4 was isolated. The full-length gene was recovered by performing rapid amplification of cDNA ends (RACE). The nucleotide sequence of the coding region of the cDNA is presented in FIG. 1 (SEQ ID NO:1); the translated amino acid sequence is provided in FIG. 2 (SEQ ID NO:2).

The full-length CYP71D-A4 cDNA was expressed in yeast cells. To assay for amorphadiene oxidase activity, CYP71D-A4 was placed under the transcriptional control of a Gal10 promoter in a pESC-URA (Stratagene) backbone plasmid in which the CPR gene from *A. annua* (AACPR; FIG. 3; amino acid sequence of encoded protein provided in FIG. 4) was expressed from a Gal1 promoter. The AACPR gene was obtained from *A. annua* glandular trichome mRNA using a degenerate primer PCR and RACE method as described above.

To perform an in vivo assay for amorpha-4,11-diene oxidase activity, this plasmid, (p71D-A4/CPR::pESC-URA) and a control plasmid, which lacked the CYP71D-A4 gene, were transformed into *S. cerevisiae* cells engineered to produce amorpha-4,11-diene. Briefly, these cells are strain BY4742 carrying an integrated gene encoding a truncated HMG CoA reductase, which is soluble in yeast. These cells carry pRS425ADS which has a codon-optimized ADS gene under control of the GAL1 promoter. Transformed cells were cultured in synthetic leucine and uracil dropout medium and induced by 2% galactose for 29 hours and the medium was extracted with ether. Extracts were concentrated and 1 μl was analyzed by gas chromatography-mass spectroscopy (GC-MS) equipped with an EXL column using temperature program 5° C. per minute increments from 50° C. to 250° C. Authentic artemisinic acid was used to synthesize artemisinic alcohol and artemisinic aldehyde, which were used as standards. By this method, two peaks were detected from the cells expressing CPR and CYP71D-A4 but not from control cells expressing only CPR. By comparing retention time and mass spectra to the authentic standards, it was determined that these peaks corresponded to artemisinic alcohol and artemisinic aldehyde. Artemisinic acid was not detected; it would not be expected to appear using a GC without being derivatized due its low volatility.

An in vivo feeding assay for amorpha-4,11-diene oxidase activity was carried out, in which the same two plasmids were individually transformed into a wild-type strain of *S. cerevisiae*, YPH499. Yeast cells were cultured in 50 mL 2% dextrose and uracil dropout medium and were induced by 2% galactose for 24 hours. Five mL of induced yeast cells were collected by centrifugation, and fresh medium containing 150 μM amorpha-4,11-diene, artemisinic alcohol, or artemisinic aldehyde were used to resuspend yeast cells. Yeast cells were then cultured at 30° C. for 5 hours. The medium was extracted by ether followed by derivatization using N-(tert-Butyldimethylsilyl)-N-methyltrifluoroacetamide to allow detection of any artemisinic acid using GC-MS. Authentic artemisinic alcohol and artemisinic acid standards were also derivatized similarly. One μL each of the derivatized controls and samples was analyzed by GC-MS. The temperature program used was 5° C. per minute increments from 50° C. to 250° C.

Figure 5:
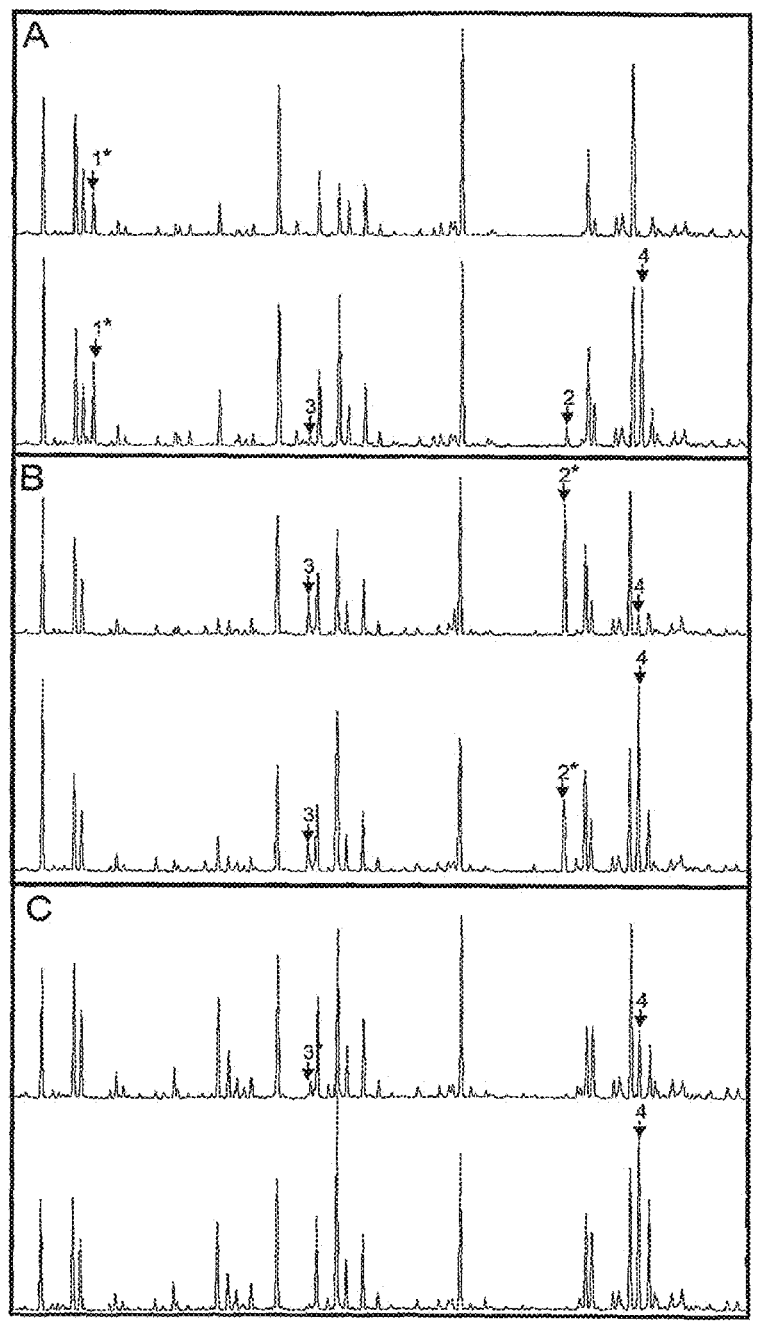
FIGS. 5A-C depicts the results of an in vivo substrate feeding experiment.

When the cells were fed amorpha-4,11-diene, significant accumulation of artemisinic acid along with small amount of artemisinic alcohol and aldehyde compounds were detected only from yeast cells expressing both CPR and CYP71D-A4 (FIG. 5A). When cells were fed artemisinic alcohol or artemisinic aldehyde, relative accumulation of artemisinic acid was higher in the culture medium of CPR/CYP71D-A4 transformed yeast cells than that of the control strain transformed with CPR alone (FIGS. 5B and 5C).

FIGS. 5A-C. Amorphadiene (FIG. 5A) and two other artemisinin intermediates—artemisinic alcohol (FIG. 5B) and artemisinic aldehyde (FIG. 5C)—were added to the medium at 150 μM in which yeast cells transformed with CPR alone (upper chromatograph) or with both CPR and CYP71D-A4 (lower chromatograph) were cultured and induced by 2% galactose. Amorphadiene (1), artemisinic alcohol (2), artemisinic aldehyde (3), and artemisinic acid (4) are indicated by arrows. Artemisinic alcohol (2) and artemisinic acid (4) were detected after derivatization by N-(tert-Butyldimethylsilyl)-N-methyltrifluoroacetamide. Asterisk indicates substrates added to the medium.

Figure 6A:
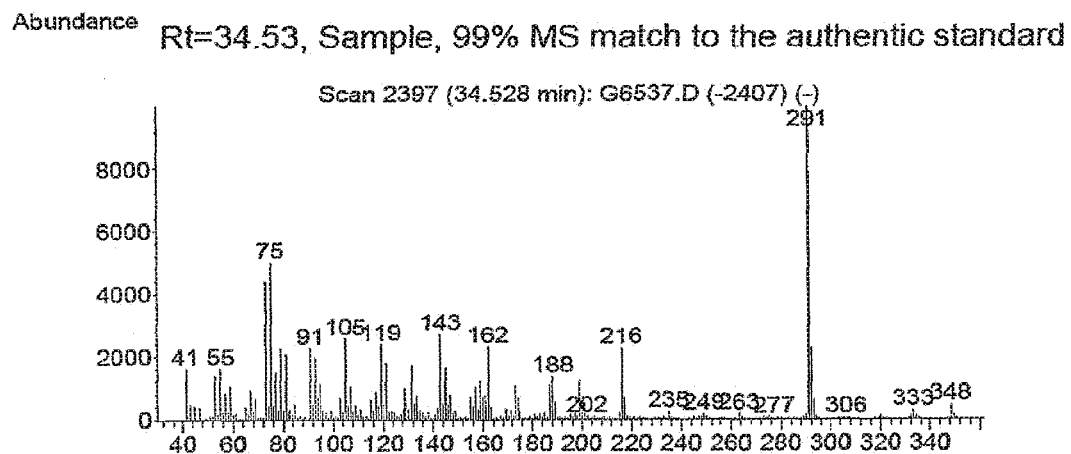
FIGS. 6A and 6B depict product confirmation by GC-MS.
Figure 6B:
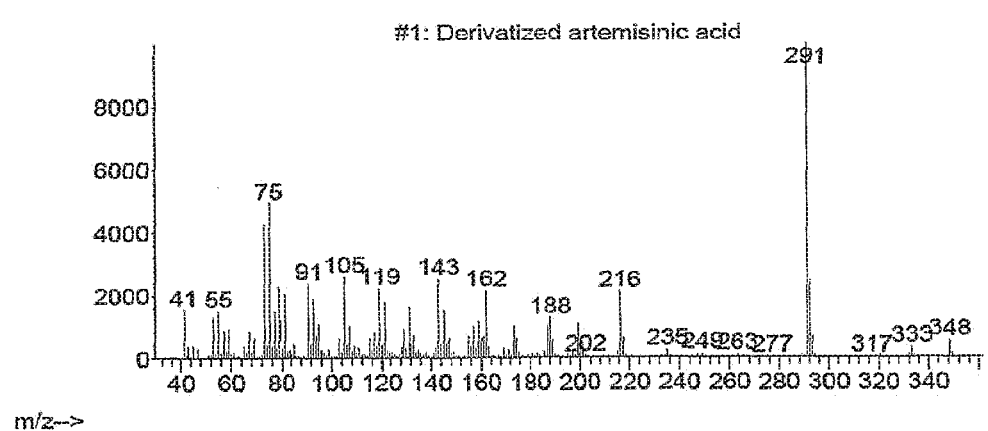

The authenticity of derivatized artemisinic acid in samples was confirmed by the authentic artemisinic acid standard (FIGS. 6A and 6B). These data indicated that the first hydroxylation is catalyzed by the cytochrome P450 enzyme encoded in CYP71D-A4 clone, and the subsequent oxidative conversion of artemisinic alcohol to artemisinic aldehyde and artemisinic aldehyde to artemisinic acid are highly likely to be catalyzed by the CYP71D-A4 recombinant enzyme, together with yeast endogenous oxidation activities.

FIGS. 6A and 6B. Mass spectrum and retention time of the novel compound produced after amorphadiene feeding to CPR/71D-A4 transformed yeast cells are shown in FIG. 6A, and those of the artemisinic acid authentic standard are shown in FIG. 6B. Both product and standard were detected by GC-MS after derivatization, which added 114 mass units to the base molecular weight.

De novo synthesis of artemisinic acid in engineered yeast from a simple sugar such as galactose was shown by genetically modifying EPY224 with pESC-URA harboring both CPR ("AACPR") and AMO ("CYP17D-A4") (pESC-URA::AACPR/AMO. A construct encoding truncated yeast HMG-CoA reductase was integrated twice into yeast strain BY4742. Transcription factor upc2-1 was overexpressed to elevate transcription level of several genes in ergosterol biosynthetic pathway. Squalene synthase gene (ERG9) was down-regulated by methionine repressible promoter, MET3. FPP synthase was overexpressed by Gall promoter, and ADS was also overexpressed by Gall promoter in pRS425 backbone. Yeast EPY224 strain harboring pESC-URA::AACPR/AMO was cultured in synthetic medium containing 1.8% galactose and 0.2% glucose for 5 days at 30° C. Yeast cells were pelleted, and the pellet was washed with alkaline buffer (Tris buffer pH 9). The buffer was acidified to pH 2 by adding HCl; and the acidified buffer was extracted with ethyl acetate. TMS-diazomethane and methanol were added to the ethyl acetate fraction to derivatize artemisinic acid. The methyl ester form of artmisinic acid was detected by GC-MS.

Figure 7:
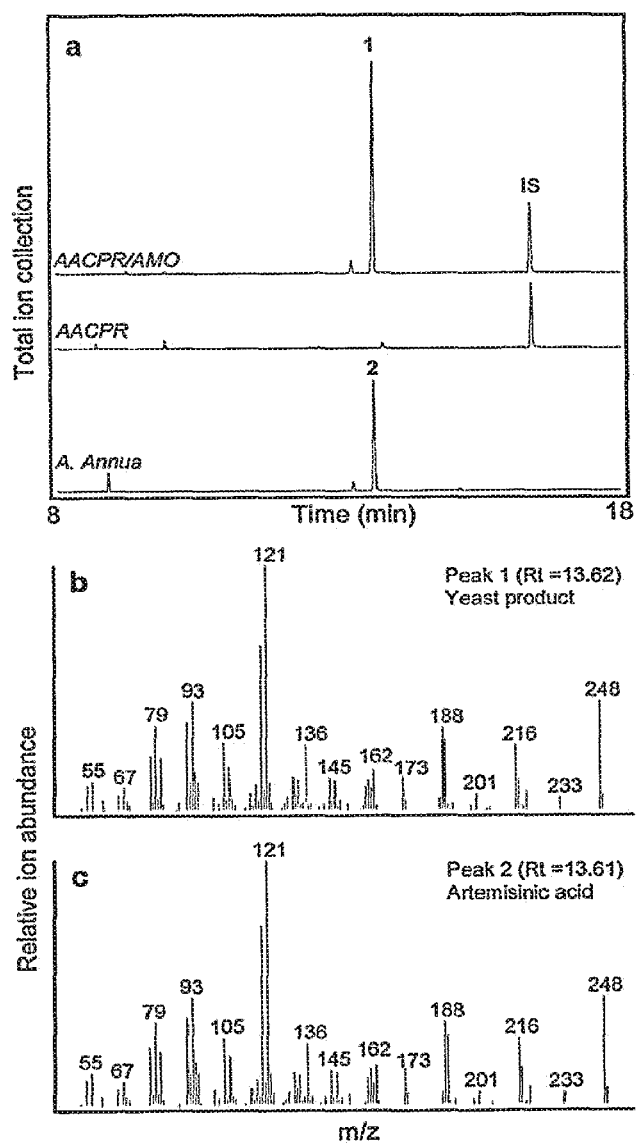
FIGS. 7A-C depict de novo production of artemisinic acid in yeast.

FIGS. 7A-7C depict de novo production of artemisinic acid in yeast, when AACPR and AMO are expressed. In contrast, no artemisinic acid was detected in a control yeast strain expressing AACPR alone. The novel peak at 13.62 min (FIG. 7A, peak 1) showed the same mass fragmentation patterns as the authentic artemisinic acid from plant, *Artemisia annua* (FIG. 7 B and C).

Figure 8:
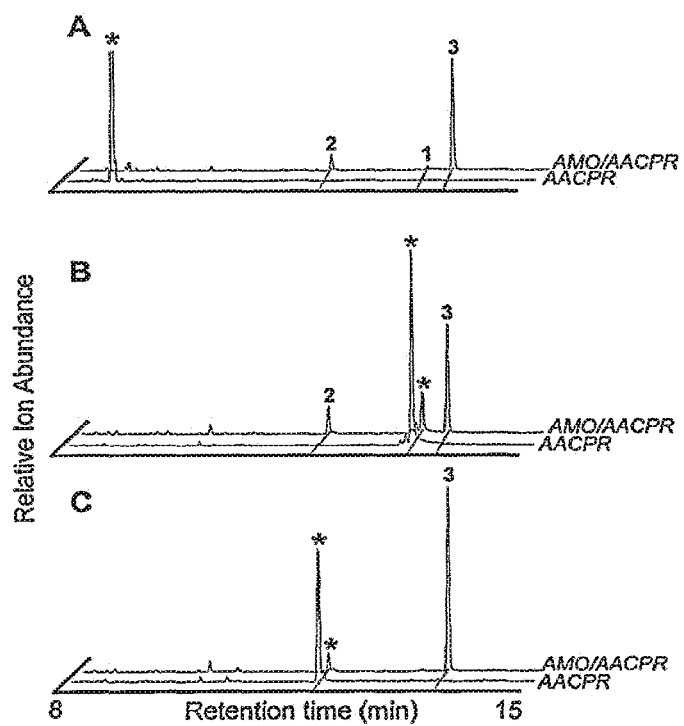
FIGS. 8A-C depict in vitro amorphadiene oxidase enzyme assays.

FIGS. 8A-8C depict in vitro AMO enzyme assays. Microsomes were isolated from *S. cerevisiae* YPH499 expressing AACPR or CPR/AMO. Chromatographic peaks for the substrates used are shown by asterisks. For each enzyme assay, 10 μM amorphadiene (a), 25 μM artemisinic alcohol (b), or 25 μM artemisinic aldehyde (c) was used. Ether-extractable fractions were derivatized and analyzed by GC-MS in the selective ion mode (m/z: 121, 189, 204, 218, 220, and 248). Enzymatic products are as indicated: 1, artemisinic alcohol [retention time (Rt)=13.20]; 2, artemisinic aldehyde (Rt=11.79); 3, artemisinic acid (Rt=13.58, detected as methyl ester).

FIG. 9 depicts the nucleotide sequence of a cDNA clone, designated 71D-B1 (also referred to as "AMH," for amorphadiene hydroxylase), that encodes a terpene hydroxylase.

FIG. 10 depicts the amino acid sequence of the protein encoded by 71D-B1 (AMH).

Figure 11:
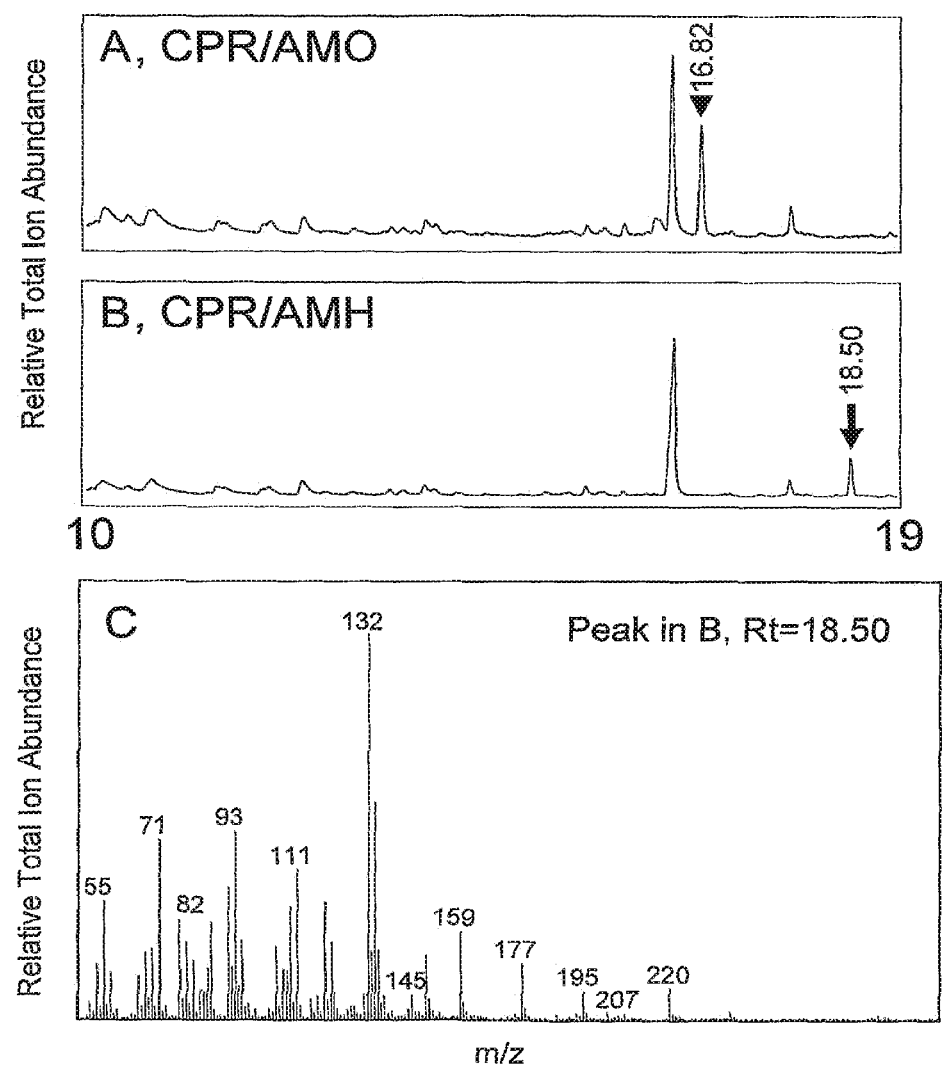
FIGS. 11A-C depict the hydroxylation activity of the enzyme 71D-B1.

FIGS. 11A-C depict the hydroxylation activity of recombinant enzyme encoded in AMH clone (71D-B1). The peak at 16.82 min in A is artemisinic acid when AMO was expressed in HMGCoA-overexpressing yeast, and the peak at 18.50 min in B is hydroxylated amorphadiene when AMH and AACPR was overexpressed in HMGCoA overexpressed yeast. The mass fragmentation patterns of hydroxylated amorphadiene were given in FIG. 11C. Peak for the parental ion (220) of hydroxylated amorphadiene is shown and other typical ion fragmentation patterns for sesquiterpenes and terpenes are also shown (e.g., 93, 119, 132, 145, 159, and 177).

FIG. 12 depicts the nucleotide sequence of a genomic DNA encoding a terpene hydroxylase/oxidase.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An isolated cDNA comprising:
a nucleotide sequence that encodes a cytochrome P450 reductase (CPR), wherein the CPR comprises an amino acid sequence having at least 85% amino acid sequence identity to the amino acid sequence set forth in SEQ ID NO:4, wherein the CPR transfers electrons from NADPH to an isoprenoid-modifying enzyme.

2. A recombinant vector comprising a polynucleotide comprising a nucleotide sequence that encodes a cytochrome P450 reductase (CPR), wherein the CPR comprises an amino acid sequence having at least 85% amino acid sequence identity to the amino acid sequence set forth in SEQ ID NO: 4, wherein the CPR transfers electrons from NADPH to an isoprenoid-modifying enzyme.

3. A host cell comprising the cDNA of claim 1.

4. A host cell comprising the recombinant vector of claim 2.

5. A transgenic plant comprising a nucleic acid comprising a nucleotide sequence encoding as isoprenoid-modifying enzyme having at least about 90% amino acid identity to the amino acid sequence set forth in SEQ ID NO:2, wherein the nucleic acid is expressed in a cell of the plant to produce the isoprenoid-modifying enzyme in the cell.

6. The transgenic plant of claim 5, wherein the plant is a monocot.

7. The transgenic plant of claim 5, wherein the plant is a dicot.

8. The transgenic plant of claim 5, wherein the plant is tobacco.

9. The transgenic plant of claim 5, wherein the isoprenoid-modifying enzyme-encoding nucleotide sequence is operably linked to a constitutive promoter.

10. The transgenic plant of claim 5, wherein the isoprenoid-modifying enzyme-encoding nucleotide sequence is operably linked to an inducible promoter.

11. The transgenic plant of claim 5, wherein the isoprenoid-modifying enzyme-encoding nucleotide sequence is operably linked to a tissue-specific promoter.

12. The transgenic plant of claim 11, wherein the tissue-specific promoter is a trichome-specific promoter.

13. The transgenic plant of claim 5, wherein the plant is *Artemisia annua*.

14. A method of producing an isoprenoid compound, the method comprising maintaining the transgenic plant of claim 5 under conditions that favor production of the isoprenoid-modifying enzyme, wherein production of the isoprenoid-modifying enzyme results in modification of a terpene substrate and production of an isoprenoid compound.

15. The cDNA of claim 1, wherein the CPR comprises an amino acid sequence having at least 90% amino acid sequence identity to the amino acid sequence set forth in SEQ ID NO:4.

16. The cDNA of claim 1, wherein the CPR comprises an amino acid sequence having at least 95% amino acid sequence identity to the amino acid sequence set forth in SEQ ID NO:4.

17. The recombinant vector of claim 2, wherein said nucleotide sequence is operably linked to a promoter.

18. The recombinant vector of claim 2, further comprising a nucleic acid encoding an isoprenoid-modifying enzyme having at least 90% amino acid sequence identity to the amino acid sequence set forth in SEQ ID NO:2.

19. The recombinant vector of claim 2, wherein the isoprenoid-modifying enzyme exhibits amorpha-4,11-diene oxidase activity.

20. The host cell of claim 4, wherein the host further comprises an expression vector encoding an amorpha-4,11-diene oxidase having at least 90% amino acid sequence identity to the amino acid sequence set forth in SEQ ID NO:2.

21. The host cell of claim 3, wherein the host cell is a prokaryotic cell, a yeast cell, or a plant cell.

22. The host cell of claim 4, wherein the host cell is a prokaryotic cell, a yeast cell, or a plant cell.

23. A transgenic plant genetically modified with a nucleic acid comprising a nucleotide sequence that encodes a cytochrome P450 reductase (CPR), wherein the CPR comprises an amino acid sequence having at least 85% amino acid sequence identity to the amino acid sequence set forth in SEQ ID NO:4, wherein the CPR transfers electrons from NADPH to an isoprenoid-modifying enzyme.

24. A transgenic plant according to claim 23, further comprising a polypeptide having at least 90% amino acid sequence identity to the amino acid sequence set forth in SEQ ID NO:2, wherein the polypeptide exhibits amorpha-4,11-diene oxidase activity.

25. The transgenic plant of claim 23, wherein the plant is tobacco or *Artemisia annua*.

26. The recombinant vector of claim 2, wherein the CPR comprises an amino acid sequence having at least 90% amino acid sequence identity to the amino acid sequence set forth in SEQ ID NO: 4.

27. The recombinant vector of claim 2, wherein the CPR comprises an amino acid sequence having at least 95% amino acid sequence identity to the amino acid sequence set forth in SEQ ID NO: 4.

* * * * *

SEQUENCE LISTING

```
<160> NUMBER OF SEQ ID NOS: 33

<210> SEQ ID NO 1
<211> LENGTH: 1488
<212> TYPE: DNA
<213> ORGANISM: Artemisia annua

<400> SEQUENCE: 1
atgaagagta tactaaaagc aatggcactc tcactgacca cttccattgc tcttgcaacg      60
atccttttgt tcgtttacaa gttcgctact cgttccaaat ccaccaaaaa aagccttcct     120
gagccatggc ggcttcccat tattggtcac atgcatcact tgattggtac aacgccacat     180
cgtggggtta gggatttagc cagaaagtat ggatctttga tgcatttaca gcttggtgaa     240
gttccaacaa tcgtggtgtc atctccgaaa tgggctaaag agattttgac aacgtacgac     300 attaccttttg ctaacaggcc cgagacttta actggtgaga ttgtttttata tcacaatacg     360 gatgttgttc ttgcacctta tggtgaatac tggaggcaat acgtaaaaat ttgcacattg     420
gagcttttga gtgttaagaa agtaaagtca tttcagtcac ttcgtgaaga ggagtgttgg     480
aatttggttc aagagattaa agcttcaggt tcagggagac cggttaacct ttcagagaat     540
```

```
gttttcaagt tgattgcaac gatacttagt agagccgcat ttgggaaagg gatcaaggac    600
cagaaagagt taacggagat tgtgaaagag atactgaggc aaactggtgg ttttgatgtg    660
gcagatatct ttccttcaaa gaaatttctt catcatcttt cgggcaagag agctcggtta    720
actagccttc gcaaaaagat cgataattta atcgataacc ttgtagctga gcatactgtt    780
aacacctcca gtaaaactaa cgagacactc ctcgatgttc ttttaaggct caaagacagt    840
gctgaattcc cattaacatc tgataacatt aaagccatca ttttggatat gtttggagca    900
ggcacagaca cttcctcatc cacaatcgaa tgggcgattt cggaactcat aaagtgtccg    960
aaagcaatgg agaagtaca agcggaattg aggaaagcat tgaacggaaa agaaaagatc   1020
catgaggaag acattcaaga actaagctac ttgaacatgg taatcaaaga aacattgagg   1080
ttgcaccctc cactacccct tggttctgcca agagagtgcc gccaaccagt caatttggct   1140
ggatacaaca tacccaataa gaccaaactt attgtcaacg tctttgcgat aaatagggac   1200
cctgaatatt ggaagacgc tgaagctttc atccctgaac gatttgaaaa tagttctgca   1260
actgtcatgg gtgcagaata cgagtatctt ccgtttggag ctgggagaag gatgtgtcct   1320
ggagccgcac ttggtttagc taacgtgcag ctcccgctcg ctaatatact atatcatttc   1380
aactggaaac tccccaatgg tgtgagctat gaccagatcg acatgaccga gagctctgga   1440
gccacgatgc aaagaaagac tgagttgtta ctcgttccaa gtttctag                1488
```

<210> SEQ ID NO 2
<211> LENGTH: 495
<212> TYPE: PRT
<213> ORGANISM: Artemisia annua

<400> SEQUENCE: 2

```
Met Lys Ser Ile Leu Lys Ala Met Ala Leu Ser Leu Thr Thr Ser Ile
  1               5                  10                  15

Ala Leu Ala Thr Ile Leu Leu Phe Val Tyr Lys Phe Ala Thr Arg Ser
             20                  25                  30

Lys Ser Thr Lys Lys Ser Leu Pro Glu Pro Trp Arg Leu Pro Ile Ile
         35                  40                  45

Gly His Met His His Leu Ile Gly Thr Thr Pro His Arg Gly Val Arg
     50                  55                  60

Asp Leu Ala Arg Lys Tyr Gly Ser Leu Met His Leu Gln Leu Gly Glu
 65                  70                  75                  80

Val Pro Thr Ile Val Val Ser Ser Pro Lys Trp Ala Lys Glu Ile Leu
                 85                  90                  95

Thr Thr Tyr Asp Ile Thr Phe Ala Asn Arg Pro Glu Thr Leu Thr Gly
            100                 105                 110

Glu Ile Val Leu Tyr His Asn Thr Asp Val Val Leu Ala Pro Tyr Gly
        115                 120                 125

Glu Tyr Trp Arg Gln Leu Arg Lys Ile Cys Thr Leu Glu Leu Leu Ser
    130                 135                 140

Val Lys Lys Val Lys Ser Phe Gln Ser Leu Arg Glu Glu Glu Cys Trp
145                 150                 155                 160

Asn Leu Val Gln Glu Ile Lys Ala Ser Gly Ser Gly Arg Pro Val Asn
                165                 170                 175

Leu Ser Glu Asn Val Phe Lys Leu Ile Ala Thr Ile Leu Ser Arg Ala
            180                 185                 190

Ala Phe Gly Lys Gly Ile Lys Asp Gln Lys Glu Leu Thr Glu Ile Val
        195                 200                 205

Lys Glu Ile Leu Arg Gln Thr Gly Gly Phe Asp Val Ala Asp Ile Phe
```

```
                 210                 215                 220
Pro Ser Lys Lys Phe Leu His His Leu Ser Gly Lys Arg Ala Arg Leu
225                 230                 235                 240

Thr Ser Leu Arg Lys Lys Ile Asp Asn Leu Ile Asp Asn Leu Val Ala
                245                 250                 255

Glu His Thr Val Asn Thr Ser Ser Lys Thr Asn Glu Thr Leu Leu Asp
                    260                 265                 270

Val Leu Leu Arg Leu Lys Asp Ser Ala Glu Phe Pro Leu Thr Ser Asp
                275                 280                 285

Asn Ile Lys Ala Ile Ile Leu Asp Met Phe Gly Ala Gly Thr Asp Thr
290                 295                 300

Ser Ser Ser Thr Ile Glu Trp Ala Ile Ser Glu Leu Ile Lys Cys Pro
305                 310                 315                 320

Lys Ala Met Glu Lys Val Gln Ala Glu Leu Arg Lys Ala Leu Asn Gly
                325                 330                 335

Lys Glu Lys Ile His Glu Glu Asp Ile Gln Glu Leu Ser Tyr Leu Asn
                340                 345                 350

Met Val Ile Lys Glu Thr Leu Arg Leu His Pro Pro Leu Pro Leu Val
                355                 360                 365

Leu Pro Arg Glu Cys Arg Gln Pro Val Asn Leu Ala Gly Tyr Asn Ile
370                 375                 380

Pro Asn Lys Thr Lys Leu Ile Val Asn Val Phe Ala Ile Asn Arg Asp
385                 390                 395                 400

Pro Glu Tyr Trp Lys Asp Ala Glu Ala Phe Ile Pro Glu Arg Phe Glu
                405                 410                 415

Asn Ser Ser Ala Thr Val Met Gly Ala Glu Tyr Glu Tyr Leu Pro Phe
                420                 425                 430

Gly Ala Gly Arg Arg Met Cys Pro Gly Ala Ala Leu Gly Leu Ala Asn
                435                 440                 445

Val Gln Leu Pro Leu Ala Asn Ile Leu Tyr His Phe Asn Trp Lys Leu
                450                 455                 460

Pro Asn Gly Val Ser Tyr Asp Gln Ile Asp Met Thr Glu Ser Ser Gly
465                 470                 475                 480

Ala Thr Met Gln Arg Lys Thr Glu Leu Leu Leu Val Pro Ser Phe
                485                 490                 495

<210> SEQ ID NO 3
<211> LENGTH: 2157
<212> TYPE: DNA
<213> ORGANISM: Artemisia annua

<400> SEQUENCE: 3
atgcaatcaa caacttccgt taagttatct cccttcgatc taatgacggc gttacttaac      60
ggcaaggtat cgttcgacac atcaaacaca tcggatacga atattccgtt agcggtgttt     120
atggagaatc gtgagctttt gatgatttta actacttcgg ttgcggtgtt gatcggatgc     180
gttgtggtgc ttgtgtggag acggtcgtcg tcggcggcga agaaagcggc ggagtcgccg     240
gtgattgttg tgccgaagaa agtgacggag gatgaggttg atgacggacg aagaaaagtt     300
actgtgtttt ttggaactca gactggtact gctgaaggtt tgctaaggc gcttgttgaa      360 gaagctaaag cgcgatatga aaaggcgtg tttaaagtga ttgatttgga tgattatgct      420
gctgaagatg atgagtatga ggagaagtta agaaagaat ctcttgcttt tttcttttta      480
gctacgtatg gagatggtga ccgacagat aatgctgcta gattctataa atggtttacc      540
gagggtgaag agaaaggtga atggcttgac aagcttcaat acgcagtgtt tggacttggt     600
```

-continued

```
aacagacagt atgagcattt caacaagatt gcgaaggtgg tcgatgaaaa acttgtggag      660
cagggtgcaa agcgccttgt tcctgttggc atgggagacg atgatcaatg tatcgaagac      720
gacttcactg catggaaaga gttggtgtgg cctgagttgg atcaattact tcgtgatgag      780
gatgatacat ctgttgccac tccatacaca gctgctgttg gagaataccg tgttgtgttc      840
catgacaaac cagagacata tgatcaggat caactgacaa atggccatgc tgttcatgat      900
gctcaacatc catgcagatc caatgtcgct gtcaaaaagg agctccattc ccctctatct      960
gaccggtctt gcactcattt ggaatttgat atctctaata ctggattatc gtatgaaact     1020
ggggaccatg ttggagtcta cgttgagaat ctaagtgaag ttgtggacga agctgaaaaa     1080
ttaataggtt taccgccgca cacttatttc tcagtacata ctgataacga agacgggaca     1140
ccacttggtg gagcctcttt gccacctcct ttccctccat gcactttaag aaaagcattg     1200
gcttcctatg ccgatgtttt gagctctcct aaaaagtcag ctttgcttgc tttagctgct     1260
catgctactg attctactga agctgataga ctgaaatttt ttgcgtctcc tgctggaaag     1320
gatgaatatg ctcagtggat agttgcaagc cacagaagtc tccttgaggt catggaggcc     1380
ttcccatcag ctaagcctcc gcttggtgtt tttttgcat ctgtcgcccc acgtttgcag      1440
ccgagatact attccatttc ttcttcccca agtttgcgc caaataggat tcatgtaact      1500
tgtgcattag tgtatgagca acaccatca ggccgcgttc acaagggagt ctgttcaaca      1560
tggatgaaga atgccgtgcc tatgacagaa agccaggatt gcagttgggc cccaatttat     1620
gttagaacat ccaatttcag acttccttct gatcctaagg tcccagttat catgattggc     1680
ccaggcactg gattggctcc atttagaggt ttccttcagg aaaggttagc tcagaaggaa     1740
gctgggactg agctcggaac agccatctta ttcttcggat gcaggaatcg caaagtggat     1800
ttcatatatg aggacgagct taataatttc gtggagacgg gggctctttc cgagcttgtt     1860
acggccttct ctcgtgaagg tgccactaag gagtacgtgc aacacaagat gactcagaag     1920
gcttcggata tctggaattt actctctgag ggagcatatt tgtatgtttg cggtgatgcc     1980
aaaggcatgg ccaaagatgt acatcggact ctgcacacta ttgtgcaaga cagggatct    2040
ctagactcct caaaggcgga gctctacgtg aagaatctac aaatggcagg aagatatctc     2100
cgtgatgtat gggtcgacat ggaacagaag ttgatttccg aagaagacct cgagtaa        2157
```

<210> SEQ ID NO 4
<211> LENGTH: 718
<212> TYPE: PRT
<213> ORGANISM: Artemisia annua

<400> SEQUENCE: 4

```
Met Gln Ser Thr Thr Ser Val Lys Leu Ser Pro Phe Asp Leu Met Thr
 1               5                  10                  15

Ala Leu Leu Asn Gly Lys Val Ser Phe Asp Thr Ser Asn Thr Ser Asp
             20                  25                  30

Thr Asn Ile Pro Leu Ala Val Phe Met Glu Asn Arg Glu Leu Leu Met
         35                  40                  45

Ile Leu Thr Thr Ser Val Ala Val Leu Ile Gly Cys Val Val Val Leu
     50                  55                  60

Val Trp Arg Arg Ser Ser Ala Ala Lys Lys Ala Glu Ser Pro
 65                  70                  75                  80

Val Ile Val Val Pro Lys Lys Val Thr Glu Asp Glu Val Asp Asp Gly
                 85                  90                  95

Arg Lys Lys Val Thr Val Phe Phe Gly Thr Gln Thr Gly Thr Ala Glu
```

```
                          100                 105                 110
Gly Phe Ala Lys Ala Leu Val Glu Glu Ala Lys Ala Arg Tyr Glu Lys
                115                 120                 125

Ala Val Phe Lys Val Ile Asp Leu Asp Asp Tyr Ala Ala Glu Asp Asp
130                 135                 140

Glu Tyr Glu Glu Lys Leu Lys Lys Glu Ser Leu Ala Phe Phe Phe Leu
145                 150                 155                 160

Ala Thr Tyr Gly Asp Gly Glu Pro Thr Asp Asn Ala Ala Arg Phe Tyr
                165                 170                 175

Lys Trp Phe Thr Glu Gly Glu Lys Gly Glu Trp Leu Asp Lys Leu
                180                 185                 190

Gln Tyr Ala Val Phe Gly Leu Gly Asn Arg Gln Tyr Glu His Phe Asn
                195                 200                 205

Lys Ile Ala Lys Val Val Asp Glu Lys Leu Val Glu Gln Gly Ala Lys
                210                 215                 220

Arg Leu Val Pro Val Gly Met Gly Asp Asp Gln Cys Ile Glu Asp
225                 230                 235                 240

Asp Phe Thr Ala Trp Lys Glu Leu Val Trp Pro Glu Leu Asp Gln Leu
                245                 250                 255

Leu Arg Asp Glu Asp Asp Thr Ser Val Ala Thr Pro Tyr Thr Ala Ala
                260                 265                 270

Val Gly Glu Tyr Arg Val Val Phe His Asp Lys Pro Glu Thr Tyr Asp
                275                 280                 285

Gln Asp Gln Leu Thr Asn Gly His Ala Val His Asp Ala Gln His Pro
                290                 295                 300

Cys Arg Ser Asn Val Ala Val Lys Lys Glu Leu His Ser Pro Leu Ser
305                 310                 315                 320

Asp Arg Ser Cys Thr His Leu Glu Phe Asp Ile Ser Asn Thr Gly Leu
                325                 330                 335

Ser Tyr Glu Thr Gly Asp His Val Gly Val Tyr Val Glu Asn Leu Ser
                340                 345                 350

Glu Val Val Asp Glu Ala Glu Lys Leu Ile Gly Leu Pro Pro His Thr
                355                 360                 365

Tyr Phe Ser Val His Thr Asp Asn Glu Asp Gly Thr Pro Leu Gly Gly
                370                 375                 380

Ala Ser Leu Pro Pro Pro Phe Pro Pro Cys Thr Leu Arg Lys Ala Leu
385                 390                 395                 400

Ala Ser Tyr Ala Asp Val Leu Ser Ser Pro Lys Lys Ser Ala Leu Leu
                405                 410                 415

Ala Leu Ala Ala His Ala Thr Asp Ser Thr Glu Ala Asp Arg Leu Lys
                420                 425                 430

Phe Phe Ala Ser Pro Ala Gly Lys Asp Glu Tyr Ala Gln Trp Ile Val
                435                 440                 445

Ala Ser His Arg Ser Leu Leu Glu Val Met Glu Ala Phe Pro Ser Ala
                450                 455                 460

Lys Pro Pro Leu Gly Val Phe Phe Ala Ser Val Ala Pro Arg Leu Gln
465                 470                 475                 480

Pro Arg Tyr Tyr Ser Ile Ser Ser Ser Pro Lys Phe Ala Pro Asn Arg
                485                 490                 495

Ile His Val Thr Cys Ala Leu Val Tyr Glu Gln Thr Pro Ser Gly Arg
                500                 505                 510

Val His Lys Gly Val Cys Ser Thr Trp Met Lys Asn Ala Val Pro Met
                515                 520                 525
```

-continued

```
Thr Glu Ser Gln Asp Cys Ser Trp Ala Pro Ile Tyr Val Arg Thr Ser
        530                 535                 540
Asn Phe Arg Leu Pro Ser Asp Pro Lys Val Pro Val Ile Met Ile Gly
545                 550                 555                 560
Pro Gly Thr Gly Leu Ala Pro Phe Arg Gly Phe Leu Gln Glu Arg Leu
                565                 570                 575
Ala Gln Lys Glu Ala Gly Thr Glu Leu Gly Thr Ala Ile Leu Phe Phe
            580                 585                 590
Gly Cys Arg Asn Arg Lys Val Asp Phe Ile Tyr Glu Asp Glu Leu Asn
        595                 600                 605
Asn Phe Val Glu Thr Gly Ala Leu Ser Glu Leu Val Thr Ala Phe Ser
    610                 615                 620
Arg Glu Gly Ala Thr Lys Glu Tyr Val Gln His Lys Met Thr Gln Lys
625                 630                 635                 640
Ala Ser Asp Ile Trp Asn Leu Leu Ser Glu Gly Ala Tyr Leu Tyr Val
                645                 650                 655
Cys Gly Asp Ala Lys Gly Met Ala Lys Asp Val His Arg Thr Leu His
            660                 665                 670
Thr Ile Val Gln Glu Gln Gly Ser Leu Asp Ser Ser Lys Ala Glu Leu
        675                 680                 685
Tyr Val Lys Asn Leu Gln Met Ala Gly Arg Tyr Leu Arg Asp Val Trp
    690                 695                 700
Val Asp Met Glu Gln Lys Leu Ile Ser Glu Glu Asp Leu Glu
705                 710                 715

<210> SEQ ID NO 5
<211> LENGTH: 1467
<212> TYPE: DNA
<213> ORGANISM: Artemisia annua

<400> SEQUENCE: 5
atggcacttt cactgaccac ctccattgct cttgccacga tccttttctt cgtaatttac      60
aagttcgcta ctcgttccaa atccacaaaa aacagccttc ctgagccatg gcgacttccc     120
attattggtc acatgcatca cttgattggt acaataccac atcgtgggct tatggattta     180
gccagaaagt atggatcttt aatgcattta cagcttggtg aagtttcaac aatcgtggtg     240
tcatctccga aatgggctaa agagattttg acaacgtacg acattgcctt tgctaacagg     300
ccctggactt tggctggtga gattgttgta tatcgcaata caaatattgc tgctgcacct     360
tatggtgaat actggaggcg attacgtaaa ctttgcacat cggagcttat gagtgttaag     420
aaagtaaagt catatcagtc gcttcgtgaa gaggagtgtt ggaatttggt tcaagagatt     480
aaagcttcag gttcagggat accggttaac ctttcagaga cattttcaa gttgattgca     540 acgatacttt gtagagccgc gtttggaaaa ggagtcaagg accagaagga gtgtacggag     600
attatgaaag atgttgag ggaagttggt ggttttgatg tggcagatat ctttccttcg     660
aagaaatttc ttcatcatct ttcaggcaag agagccaggt taactagcat tcataagaag     720
ctcgataatt ttatcaataa ccttgttgct gagcatactt tcaaaacttc aagtaaaact     780
gaggagacac ttcttgatgt tcttctaagg ctcaaagata gcgctgaatt cccattaaca     840
gctgacaatg ttaaagccat cattttggat atatttgcag cagggacaga cacttcatca     900
accacaatcg aatgggcgat tcggaactc ataaagtgtc cgagagcgat ggagaaagta     960
caagcagaac tgaggaaagc acttaacgga aaagaaaaga tccatgagga agatattcaa    1020
ggactaagct acttaaactt ggtaatcaaa gaaacattaa ggttgcaccc tccactaccc    1080
```

-continued

```
ttgttgccaa gagagtgccg tgaaccagtc aatttggctg gatacgacat acccaataag    1140
acaagactta ttgtcaacgt ctttgcgata aatagggacc cagaatactg gaaagacgct    1200
gaaattttca tccccgaacg atttgaaaat agttctacaa ctctcatggg tgcagaatat    1260
gagtatcttc cgtttggagc tgggagaagg atgtgtcctg agccgcact  tggtttagcc    1320 aacgtgcagc taccgctcgc taatatacta tatcatttca actggaaact ccccaacggt    1380
gcgagctatg atcagatcga catgaccgag aggtttggaa tctcggttga aagaaagact    1440
cagttgttac tcgtaccaag tttctag                                        1467
```

<210> SEQ ID NO 6
<211> LENGTH: 488
<212> TYPE: PRT
<213> ORGANISM: Artemisia annua

<400> SEQUENCE: 6

```
Met Ala Leu Ser Leu Thr Thr Ser Ile Ala Leu Ala Thr Ile Leu Phe
 1               5                  10                  15

Phe Val Ile Tyr Lys Phe Ala Thr Arg Ser Lys Ser Thr Lys Asn Ser
                20                  25                  30

Leu Pro Glu Pro Trp Arg Leu Pro Ile Ile Gly His Met His His Leu
            35                  40                  45

Ile Gly Thr Ile Pro His Arg Gly Leu Met Asp Leu Ala Arg Lys Tyr
        50                  55                  60

Gly Ser Leu Met His Leu Gln Leu Gly Glu Val Ser Thr Ile Val Val
 65                  70                  75                  80

Ser Ser Pro Lys Trp Ala Lys Glu Ile Leu Thr Thr Tyr Asp Ile Ala
                85                  90                  95

Phe Ala Asn Arg Pro Trp Thr Leu Ala Gly Glu Ile Val Val Tyr Arg
            100                 105                 110

Asn Thr Asn Ile Ala Ala Ala Pro Tyr Gly Glu Tyr Trp Arg Arg Leu
        115                 120                 125

Arg Lys Leu Cys Thr Ser Glu Leu Met Ser Val Lys Lys Val Lys Ser
130                 135                 140

Tyr Gln Ser Leu Arg Glu Glu Glu Cys Trp Asn Leu Val Gln Glu Ile
145                 150                 155                 160

Lys Ala Ser Gly Ser Gly Ile Pro Val Asn Leu Ser Glu Asn Ile Phe
                165                 170                 175

Lys Leu Ile Ala Thr Ile Leu Cys Arg Ala Ala Phe Gly Lys Gly Val
            180                 185                 190

Lys Asp Gln Lys Glu Cys Thr Glu Ile Met Lys Glu Met Leu Arg Glu
        195                 200                 205

Val Gly Gly Phe Asp Val Ala Asp Ile Phe Pro Ser Lys Lys Phe Leu
    210                 215                 220

His His Leu Ser Gly Lys Arg Ala Arg Leu Thr Ser Ile His Lys Lys
225                 230                 235                 240

Leu Asp Asn Phe Ile Asn Asn Leu Val Ala Glu His Thr Phe Lys Thr
                245                 250                 255

Ser Ser Lys Thr Glu Glu Thr Leu Leu Asp Val Leu Leu Arg Leu Lys
            260                 265                 270

Asp Ser Ala Glu Phe Pro Leu Thr Ala Asp Asn Val Lys Ala Ile Ile
        275                 280                 285

Leu Asp Ile Phe Ala Ala Gly Thr Asp Thr Ser Ser Thr Thr Ile Glu
    290                 295                 300

Trp Ala Ile Ser Glu Leu Ile Lys Cys Pro Arg Ala Met Glu Lys Val
```

```
                    305                 310                 315                 320
Gln Ala Glu Leu Arg Lys Ala Leu Asn Gly Lys Glu Lys Ile His Glu
                325                 330                 335

Glu Asp Ile Gln Gly Leu Ser Tyr Leu Asn Leu Val Ile Lys Glu Thr
            340                 345                 350

Leu Arg Leu His Pro Pro Leu Pro Leu Leu Pro Arg Glu Cys Arg Glu
        355                 360                 365

Pro Val Asn Leu Ala Gly Tyr Asp Ile Pro Asn Lys Thr Arg Leu Ile
    370                 375                 380

Val Asn Val Phe Ala Ile Asn Arg Asp Pro Glu Tyr Trp Lys Asp Ala
385                 390                 395                 400

Glu Ile Phe Ile Pro Glu Arg Phe Glu Asn Ser Ser Thr Thr Leu Met
                405                 410                 415

Gly Ala Glu Tyr Glu Tyr Leu Pro Phe Gly Ala Gly Arg Arg Met Cys
            420                 425                 430

Pro Gly Ala Ala Leu Gly Leu Ala Asn Val Gln Leu Pro Leu Ala Asn
        435                 440                 445

Ile Leu Tyr His Phe Asn Trp Lys Leu Pro Asn Gly Ala Ser Tyr Asp
    450                 455                 460

Gln Ile Asp Met Thr Glu Arg Phe Gly Ile Ser Val Glu Arg Lys Thr
465                 470                 475                 480

Gln Leu Leu Leu Val Pro Ser Phe
                485

<210> SEQ ID NO 7
<211> LENGTH: 1038
<212> TYPE: DNA
<213> ORGANISM: Artemisia annua

<400> SEQUENCE: 7
gcccttcgag ccgtatgggg attactggcg gcaattacgt aaactttgca cattggagct      60
tttgagtgct aagaaagtag agtcatatca gtcgcttcgt gaagaggagt gttggaattt     120
agttcaagag attaaagctt caggttcagg gataccggtt aacctttcag agaatattta     180
caagttggtt gcaatgatac ttagtagagc tgcgtttggg aaaagaatca aggaccataa     240
ggagtttacg gagcttgtgg aacagatgtt gagggaactt ggtggttttg atgtggcaga     300
tatctttcct tcgcagaaat ttctacatca tatttcgggc aagagatcta ggttaactag     360
cattcacaaa aagctcgata atttaatcaa taaccttgtt gctgagcata ttgttgaagc     420
ctcaagtaaa actaaggaga cgctccttga tgttcttcta aggcacaaag atagccttga     480
attcccattg acagctgata acgttaaagc catcattttg gtatgaatta atccaatata     540 ttttttttt caaaaggcca taatagtgtt aaacaagctt gaaattttt ataactaagt       600 acatgcacta actttagtac tcgtgaaaat ataatgagtc atcataggg ttccatgaaa      660 tatacaggac atgtttacag caggcacaga cacttcgtca accacaatcg aatgggtgat     720
ttcggaactc ataagtgtc cgagagctat ggagaaaata caagcggaac tgaggaaagc      780
acttaacgga aaagaaaaga tccacgagga agacatccaa gaactaagct acttaaactt     840
ggtaatcaaa gaacattaa ggttgcaccc tccactaccc ttggttttgc cacgagagtg      900
ccgtcaacca gtcaatttgg ctggatatga catacccaat aagaccaaac ttattgtcaa     960
cgtctttgcg ataaataggg accctgaata ctggaaagac gctgaatctt tcatcccaga    1020
gcgcttctta actctggt                                                   1038
```

```
<210> SEQ ID NO 8
<211> LENGTH: 6
<212> TYPE: PRT
<213> ORGANISM: Artificial Sequence
<220> FEATURE:
<223> OTHER INFORMATION: linker peptide

<400> SEQUENCE: 8

Ala Ala Ala Gly Gly Met
 1               5

<210> SEQ ID NO 9
<211> LENGTH: 14
<212> TYPE: PRT
<213> ORGANISM: Artificial Sequence
<220> FEATURE:
<223> OTHER INFORMATION: linker peptide

<400> SEQUENCE: 9

Ala Ala Ala Gly Gly Met Pro Pro Ala Ala Ala Gly Gly Met
 1               5                  10

<210> SEQ ID NO 10
<211> LENGTH: 6
<212> TYPE: PRT
<213> ORGANISM: Artificial Sequence
<220> FEATURE:
<223> OTHER INFORMATION: linker peptide

<400> SEQUENCE: 10

Ala Ala Ala Gly Gly Met
 1               5

<210> SEQ ID NO 11
<211> LENGTH: 8
<212> TYPE: PRT
<213> ORGANISM: Artificial Sequence
<220> FEATURE:
<223> OTHER INFORMATION: linker peptide

<400> SEQUENCE: 11

Pro Pro Ala Ala Ala Gly Gly Met
 1               5

<210> SEQ ID NO 12
<211> LENGTH: 4
<212> TYPE: PRT
<213> ORGANISM: Artificial Sequence
<220> FEATURE:
<223> OTHER INFORMATION: linker peptide

<400> SEQUENCE: 12

Ile Glu Gly Arg
 1

<210> SEQ ID NO 13
<211> LENGTH: 6
<212> TYPE: PRT
<213> ORGANISM: Artificial Sequence
<220> FEATURE:
<223> OTHER INFORMATION: linker peptide

<400> SEQUENCE: 13

Gly Gly Lys Gly Gly Lys
 1               5

<210> SEQ ID NO 14
<211> LENGTH: 25
```

<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: 9, 18, 20
<223> OTHER INFORMATION: N = C or T
<220> FEATURE:
<221> NAME/KEY: misc_feature
<222> LOCATION: 11, 14, 17
<223> OTHER INFORMATION: n = A,T,C or G

<400> SEQUENCE: 14
tccgaccana nggngannan tggag                               25

<210> SEQ ID NO 15
<211> LENGTH: 25
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (13)...(13)
<223> OTHER INFORMATION: N = G or T
<220> FEATURE:
<221> NAME/KEY: misc_feature
<222> LOCATION: (14)...(14)
<223> OTHER INFORMATION: N = C or T
<220> FEATURE:
<221> NAME/KEY: misc_feature
<222> LOCATION: (20)...(20)
<223> OTHER INFORMATION: N = A, G or T
<220> FEATURE:
<221> NAME/KEY: misc_feature
<222> LOCATION: (23)...(23)
<223> OTHER INFORMATION: N = A or G
<220> FEATURE:
<221> NAME/KEY: misc_feature
<222> LOCATION: 11,17
<223> OTHER INFORMATION: n = A,T,C or G

<400> SEQUENCE: 15
tccgaccaaa ncnntcnggn atnaa                               25

<210> SEQ ID NO 16
<211> LENGTH: 29
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (9)...(9)
<223> OTHER INFORMATION: N = A or G
<220> FEATURE:
<221> NAME/KEY: misc_feature
<222> LOCATION: (12)...(12)
<223> OTHER INFORMATION: N = C or T
<220> FEATURE:
<221> NAME/KEY: misc_feature
<222> LOCATION: (15)...(15)
<223> OTHER INFORMATION: N = A or G
<220> FEATURE:
<221> NAME/KEY: misc_feature
<222> LOCATION: (18)...(18)
<223> OTHER INFORMATION: N = C or T
<220> FEATURE:
<221> NAME/KEY: misc_feature
<222> LOCATION: (21)...(21)
<223> OTHER INFORMATION: N = C or T
<220> FEATURE:
<221> NAME/KEY: misc_feature
<222> LOCATION: (24)...(24)
<223> OTHER INFORMATION: N = C or T

```
<220> FEATURE:
<221> NAME/KEY: misc_feature
<222> LOCATION: (27)...(27)
<223> OTHER INFORMATION: N = A or G

<400> SEQUENCE: 16
ccagcacant angancantt naanaanat                                  29

<210> SEQ ID NO 17
<211> LENGTH: 29
<212> TYPE: DNA
<213> ORGANISM: Artificial Sequence
<220> FEATURE:
<223> OTHER INFORMATION: synthetic primer
<220> FEATURE:
<221> NAME/KEY: misc_feature
<222> LOCATION: (15)...(15)
<223> OTHER INFORMATION: N = C or T
<220> FEATURE:
<221> NAME/KEY: misc_feature
<222> LOCATION: (21)...(21)
<223> OTHER INFORMATION: N = A or G
<220> FEATURE:
<221> NAME/KEY: misc_feature
<222> LOCATION: (27)...(27)
<223> OTHER INFORMATION: N = A or G
<220> FEATURE:
<221> NAME/KEY: misc_feature
<222> LOCATION: 12, 18, 24
<223> OTHER INFORMATION: n = A,T,C or G

<400> SEQUENCE: 17
ccagcagcca tnccnttngc ntcnccnca                                  29

<210> SEQ ID NO 18
<211> LENGTH: 33
<212> TYPE: DNA
<213> ORGANISM: Artificial Sequence
<220> FEATURE:
<223> OTHER INFORMATION: synthetic primer

<400> SEQUENCE: 18
acgtctagaa tgaagagtat actaaaagca atg                             33

<210> SEQ ID NO 19
<211> LENGTH: 34
<212> TYPE: DNA
<213> ORGANISM: Artificial Sequence
<220> FEATURE:
<223> OTHER INFORMATION: synthetic primer

<400> SEQUENCE: 19
acgtctagag cgaaacttgg aacgagtaac aact                            34

<210> SEQ ID NO 20
<211> LENGTH: 37
<212> TYPE: DNA
<213> ORGANISM: Artificial Sequence
<220> FEATURE:
<223> OTHER INFORMATION: synthetic primer

<400> SEQUENCE: 20
atggatccta tgcaatcaac aacttccgtt aagttat                         37

<210> SEQ ID NO 21
<211> LENGTH: 34
<212> TYPE: DNA
<213> ORGANISM: Artificial Sequence
<220> FEATURE:
<223> OTHER INFORMATION: synthetic primer
```

<400> SEQUENCE: 21
tatgtcgacc catacatcac ggagatatct tcct                                 34

<210> SEQ ID NO 22
<211> LENGTH: 32
<212> TYPE: DNA
<213> ORGANISM: Artificial Sequence
<220> FEATURE:
<223> OTHER INFORMATION: synthetic primer

<400> SEQUENCE: 22
ggactagtaa aacaatggcc ctgaccgaag ag                                   32

<210> SEQ ID NO 23
<211> LENGTH: 29
<212> TYPE: DNA
<213> ORGANISM: Artificial Sequence
<220> FEATURE:
<223> OTHER INFORMATION: synthetic primer

<400> SEQUENCE: 23
ccaagctttc agatggacat cgggtaaac                                       29

<210> SEQ ID NO 24
<211> LENGTH: 29
<212> TYPE: DNA
<213> ORGANISM: Artificial Sequence
<220> FEATURE:
<223> OTHER INFORMATION: synthetic primer

<400> SEQUENCE: 24
ctgccgcggg gccgcaaatt aaagccttc                                       29

<210> SEQ ID NO 25
<211> LENGTH: 29
<212> TYPE: DNA
<213> ORGANISM: Artificial Sequence
<220> FEATURE:
<223> OTHER INFORMATION: synthetic primer

<400> SEQUENCE: 25
ctgccgcggt agtacggatt agaagccgc                                       29

<210> SEQ ID NO 26
<211> LENGTH: 35
<212> TYPE: DNA
<213> ORGANISM: Artificial Sequence
<220> FEATURE:
<223> OTHER INFORMATION: synthetic primer

<400> SEQUENCE: 26
cgggatccaa aacaatggct gcagaccaat tggtg                                35

<210> SEQ ID NO 27
<211> LENGTH: 30
<212> TYPE: DNA
<213> ORGANISM: Artificial Sequence
<220> FEATURE:
<223> OTHER INFORMATION: synthetic primer

<400> SEQUENCE: 27
gcgtcgactt aggatttaat gcaggtgacg                                      30

<210> SEQ ID NO 28
<211> LENGTH: 35

```
<212> TYPE: DNA
<213> ORGANISM: Artificial Sequence
<220> FEATURE:
<223> OTHER INFORMATION: synthetic primer

<400> SEQUENCE: 28
cgggatccaa aacaatgagc gaagtcggta tacag                                35

<210> SEQ ID NO 29
<211> LENGTH: 34
<212> TYPE: DNA
<213> ORGANISM: Artificial Sequence
<220> FEATURE:
<223> OTHER INFORMATION: synthetic primer

<400> SEQUENCE: 29
gcgtcgactc ataacgaaaa atcagagaaa tttg                                 34

<210> SEQ ID NO 30
<211> LENGTH: 37
<212> TYPE: DNA
<213> ORGANISM: Artificial Sequence
<220> FEATURE:
<223> OTHER INFORMATION: synthetic primer

<400> SEQUENCE: 30
ggactagtaa aacaatggct tcagaaaaag aaattag                              37

<210> SEQ ID NO 31
<211> LENGTH: 30
<212> TYPE: DNA
<213> ORGANISM: Artificial Sequence
<220> FEATURE:
<223> OTHER INFORMATION: synthetic primer

<400> SEQUENCE: 31
tcccccgggc tatttgcttc tcttgtaaac                                      30

<210> SEQ ID NO 32
<211> LENGTH: 8
<212> TYPE: PRT
<213> ORGANISM: Artificial Sequence
<220> FEATURE:
<223> OTHER INFORMATION: motif

<400> SEQUENCE: 32

Gln Tyr Glu His Phe Asn Lys Ile
 1               5

<210> SEQ ID NO 33
<211> LENGTH: 8
<212> TYPE: PRT
<213> ORGANISM: Artificial Sequence
<220> FEATURE:
<223> OTHER INFORMATION: motif

<400> SEQUENCE: 33

Cys Gly Asp Ala Lys Gly Met Ala
 1               5
```